(12) United States Patent
Mangiardi

(10) Patent No.: US 11,596,532 B2
(45) Date of Patent: Mar. 7, 2023

(54) STENT

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 116 days.

(21) Appl. No.: 16/996,268

(22) Filed: Aug. 18, 2020

(65) Prior Publication Data

US 2020/0390572 A1 Dec. 17, 2020

Related U.S. Application Data

(63) Continuation of application No. 16/045,320, filed on Jul. 25, 2018, now Pat. No. 10,779,966, which is a (Continued)

(51) Int. Cl.
*A61F 2/915* (2013.01)
*A61F 2/04* (2013.01)
(Continued)

(52) U.S. Cl.
CPC .......... *A61F 2/844* (2013.01); *A61B 17/7233* (2013.01); *A61B 17/7258* (2013.01); *A61B 17/7283* (2013.01); *A61F 2/0095* (2013.01); *A61F 2/04* (2013.01); *A61F 2/82* (2013.01); *A61B 17/7266* (2013.01); *A61B 17/7291* (2013.01); *A61F 2002/041* (2013.01); *A61F 2002/048* (2013.01); *A61F 2002/068* (2013.01); *A61F 2002/30289* (2013.01); *A61F 2210/0004* (2013.01); *A61F 2210/0061* (2013.01); *A61F 2230/005* (2013.01); *A61F 2230/0054* (2013.01); *A61F 2230/0091* (2013.01); *A61F 2250/0067* (2013.01)

(58) Field of Classification Search
None
See application file for complete search history.

(56) References Cited

U.S. PATENT DOCUMENTS 4,531,933 A * 7/1985 Norton ................... A61B 90/39
604/8
4,642,104 A 2/1987 Sakamoto et al.
(Continued)

FOREIGN PATENT DOCUMENTS

| JP | 2015-522377 | 8/2015 |
|---|---|---|
| JP | 2016-52602 | 4/2016 |
| WO | 2014014748 | 1/2014 |

OTHER PUBLICATIONS

U.S. Appl. No. 16/045,320, filed Jul. 25, 2018.
(Continued)

*Primary Examiner* — Ann Schillinger
(74) *Attorney, Agent, or Firm* — Ping Wang; Rimon Law

(57) ABSTRACT

A stent is disclosed that has an elongated body composed of a bioabsorbable polymer having a proximal end, a distal end, two open spiral channels formed on the exterior surface of the body to provide fluid communication between the proximal end and the distal end. The stent also has a central lumen open at the proximal and distal ends of the stent for the passage of a guide wire. A method for using the stent and a kit containing the stent are also disclosed.

15 Claims, 45 Drawing Sheets

Related U.S. Application Data continuation of application No. 15/363,829, filed on Nov. 29, 2016, now Pat. No. 10,245,165, which is a continuation-in-part of application No. 15/173,312, filed on Jun. 3, 2016, now Pat. No. 10,117,760, which is a continuation-in-part of application No. 14/841,196, filed on Aug. 31, 2015, now Pat. No. 10,201,440, which is a continuation of application No. 12/539,314, filed on Aug. 11, 2009, now abandoned, which is a continuation-in-part of application No. 12/417,122, filed on Apr. 2, 2009, now Pat. No. 8,246,691.

(51) Int. Cl.

| | |
|---|---|
| A61F 11/00 | (2022.01) |
| B23K 26/38 | (2014.01) |
| A61B 17/72 | (2006.01) |
| A61F 2/844 | (2013.01) |
| A61F 2/00 | (2006.01) |
| A61F 2/82 | (2013.01) |
| A61F 2/06 | (2013.01) |
| A61F 2/30 | (2006.01) |

(56) References Cited

U.S. PATENT DOCUMENTS

| | | | | |
|---|---|---|---|---|
| 5,129,910 | A | * | 7/1992 | Phan ................... A61F 2/94 606/127 |
| 5,258,042 | A | * | 11/1993 | Mehta ................... A61L 31/048 623/921 |
| 5,486,191 | A | * | 1/1996 | Pasricha ................... A61F 2/94 128/897 |
| 5,520,664 | A | | 5/1996 | Bricault, Jr. et al. |
| 5,522,881 | A | | 6/1996 | Lents |
| 5,599,291 | A | | 2/1997 | Balbierz et al. |
| 5,653,745 | A | * | 8/1997 | Trescony ................... A61F 2/06 623/1.29 |
| 5,827,321 | A | | 10/1998 | Roubin et al. |
| 5,843,172 | A | | 12/1998 | Yan |
| 5,993,483 | A | * | 11/1999 | Gianotti ................... A61F 2/90 623/1.22 |
| 6,214,037 | B1 | | 4/2001 | Mitchell et al. |
| 6,752,829 | B2 | | 6/2004 | Kocur et al. |
| 7,131,992 | B2 | | 11/2006 | Iwasaka et al. |
| 7,214,229 | B2 | | 5/2007 | Mitchell et al. |
| 7,338,530 | B2 | * | 3/2008 | Carter ................... A61F 2/07 623/23.66 |
| 7,875,069 | B2 | | 1/2011 | Heaney et al. |
| 7,988,716 | B2 | * | 8/2011 | Schwartz ................... A61F 2/02 623/1.15 |
| 10,350,093 | B2 | | 7/2019 | Yan et al. |
| 2002/0082679 | A1 | | 6/2002 | Sirhan et al. |
| 2002/0116044 | A1 | * | 8/2002 | Cottone, Jr. ........... A61F 2/915 623/1.22 |
| 2002/0179166 | A1 | * | 12/2002 | Houston ................. F15D 1/065 138/123 |
| 2003/0018306 | A1 | | 1/2003 | Bucay-Couto et al. |
| 2003/0040754 | A1 | * | 2/2003 | Mitchell .............. A61B 17/221 606/106 |
| 2004/0034403 | A1 | * | 2/2004 | Schmitt ................... A61F 2/07 623/1.22 |
| 2004/0037986 | A1 | * | 2/2004 | Houston ................... A61F 2/90 428/36.9 |
| 2005/0038501 | A1 | | 2/2005 | Moore et al. |
| 2005/0080478 | A1 | | 4/2005 | Barongan |
| 2005/0085891 | A1 | | 4/2005 | Goto et al. |
| 2005/0090888 | A1 | | 4/2005 | Hines et al. |
| 2005/0119730 | A1 | | 6/2005 | Howat et al. |
| 2006/0047334 | A1 | * | 3/2006 | Houston ................. F15D 1/065 623/1.1 |
| 2006/0100689 | A1 | | 5/2006 | Pryor |
| 2006/0136051 | A1 | * | 6/2006 | Furst ....................... A61F 2/915 623/1.42 |
| 2006/0265051 | A1 | * | 11/2006 | Caro ........................ F16L 9/00 623/1.17 |
| 2006/0265054 | A1 | | 11/2006 | Greenhalgh et al. |
| 2007/0032880 | A1 | | 2/2007 | Maeda |
| 2007/0129787 | A1 | | 6/2007 | Bezwada |
| 2007/0270939 | A1 | | 11/2007 | Hood et al. |
| 2007/0293963 | A1 | | 12/2007 | Jung et al. |
| 2008/0140176 | A1 | | 6/2008 | Krause et al. |
| 2008/0200976 | A1 | | 8/2008 | Asgari |
| 2008/0319536 | A1 | | 12/2008 | Houston et al. |
| 2009/0024204 | A1 | | 1/2009 | Greenhalgh et al. |
| 2009/0187240 | A1 | | 7/2009 | Clerc et al. |
| 2009/0204082 | A1 | | 8/2009 | Wesselmann et al. |
| 2010/0036478 | A1 | * | 2/2010 | Wang ................... B29C 51/002 623/1.49 |
| 2010/0256729 | A1 | | 10/2010 | Mangiardi |
| 2010/0256731 | A1 | | 10/2010 | Mangiardi |
| 2011/0004320 | A1 | | 1/2011 | Priplata |
| 2015/0209167 | A1 | | 7/2015 | Mangiardi |
| 2015/0366681 | A1 | | 12/2015 | Mangiardi |
| 2016/0310299 | A1 | | 10/2016 | Mangirardi |

OTHER PUBLICATIONS

U.S. Appl. No. 15/363,829, filed Nov. 29, 2016.
U.S. Appl. No. 15/173,312, filed Jun. 3, 2016.
U.S. Appl. No. 14/841,196, filed Aug. 31, 2015.
U.S. Appl. No. 12/539,314, filed Aug. 11, 2009.
U.S. Appl. No. 12/417,122, filed Apr. 2, 2009.
Yuan, X., et al., "Characterization of Poly(L-lactic acid) Fibers Produced by Melt Spinning", Journal of Applied Polymer Science, vol. 81, pp. 251-260 (2001).
Carlson, R.P., et al., "Anti-biofilm Properties of Chitosan-coated Surfaces", J. Biomater. Sci. Polymer Edn., vol. 19, No. 8, pp. 1035-1046 (2008).
Van De Velde, K., et al. "Biopolymers: Overview of Several Properties and Consequences on Their Applications", Polymer Testing, vol. 21, pp. 433-442 (2002).
Donelli, G., et al., "Plastic Biliary Stent Occlusion: Factors Involved and Possible Preventive Approaches", Clin Med Res., vol. 5, No. 1, pp. 53-60 (2007).
Somogyi, L., et al. "Biliary and Pancreatic Stent", Gastrointestinal Endoscopy, vol. 63, No. 7, pp. 910-919 (2006).
File History of U.S. Appl. No. 12/539,314, filed Aug. 11, 2009.
File History of U.S. Appl. No. 14/841,196, filed Aug. 31, 2015.
File History of U.S. Appl. No. 12/417,122, filed Apr. 2, 2009.
File History of U.S. Appl. No. 15/173,312, filed Jun. 3, 2016.
File History of U.S. Appl. No. 15/363,829, filed Nov. 29, 2016.
File History of U.S. Appl. No. 16/045,320, filed Jul. 25, 2018.

\* cited by examiner

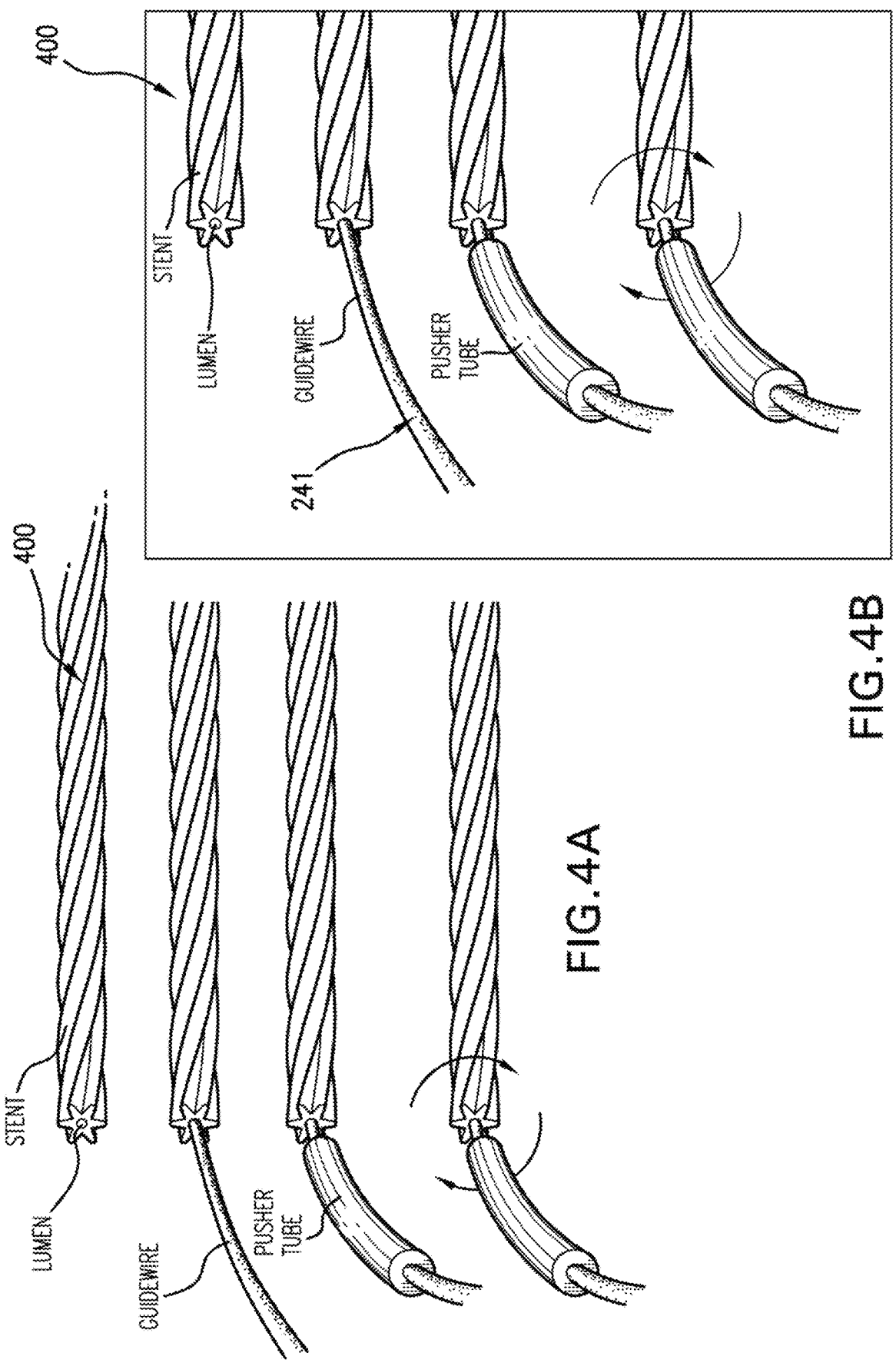

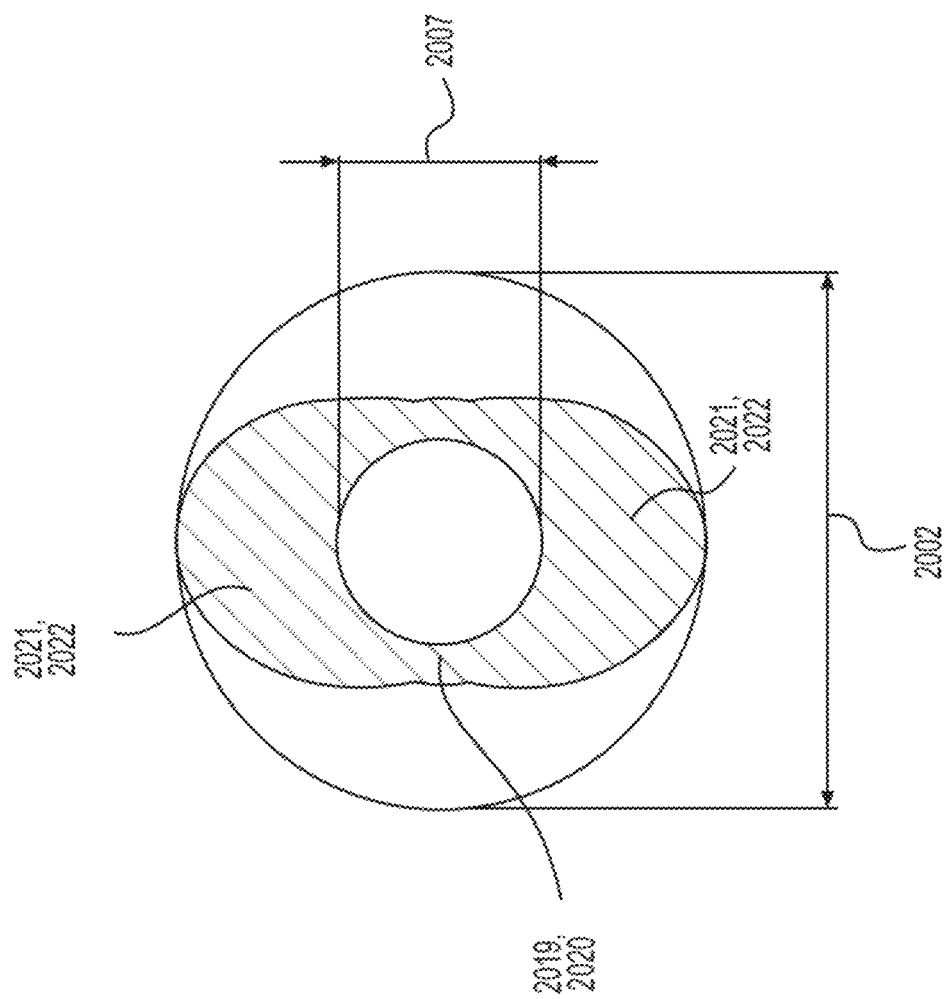

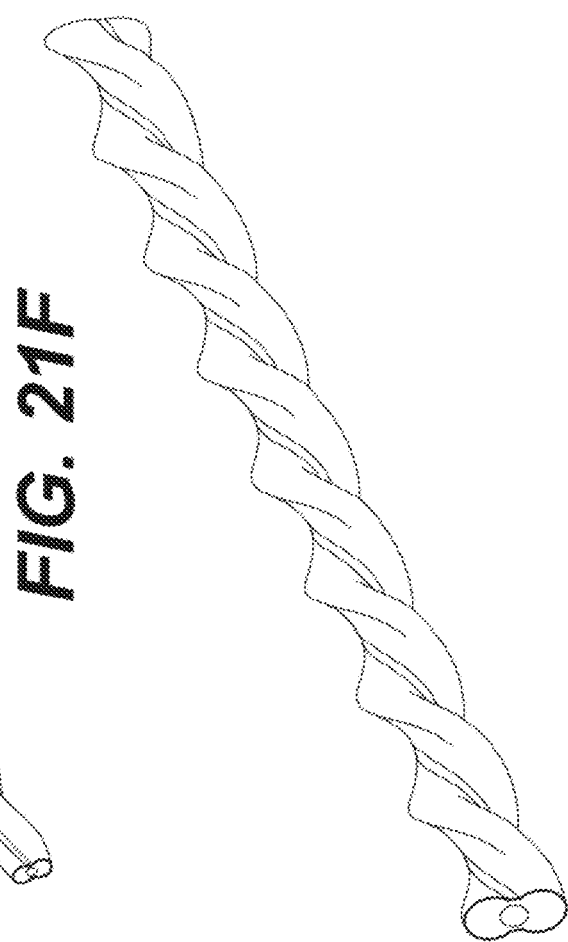
FIG. 21F
FIG. 21H
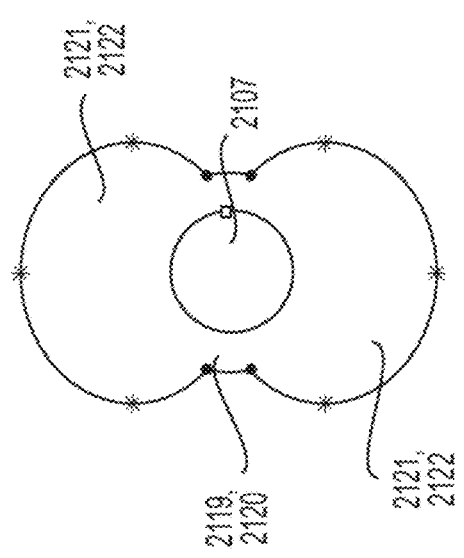
FIG. 21E
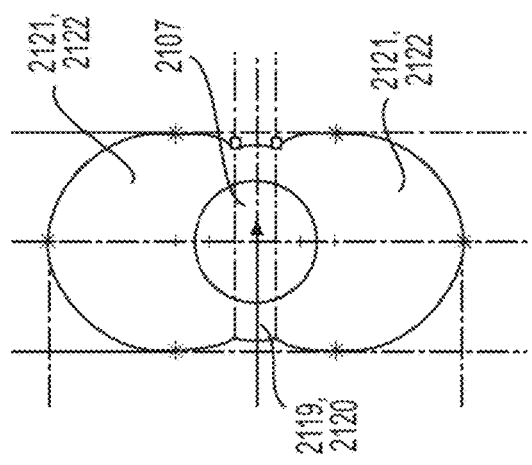
FIG. 21G

STENT

This application is a Continuation of U.S. application Ser. No. 16/045,320, filed Jul. 25, 2018, which is a Continuation of U.S. application Ser. No. 15/363,829, filed Nov. 29, 2016, now U.S. Pat. No. 10,245,165, which is a Continuation-In-Part of U.S. application Ser. No. 15/173,312, filed Jun. 3, 2016, now U.S. Pat. No. 10,117,760, which is a Continuation-In-Part of U.S. application Ser. No. 14/841,196, filed Aug. 31, 2015, now U.S. Pat. No. 10,201,440, which is a Continuation of U.S. application Ser. No. 12/539,314, filed Aug. 11, 2009, which is a Continuation-In-Part of U.S. application Ser. No. 12/417,122, filed on Apr. 2, 2009, now U.S. Pat. No. 8,246,691. The entirety of the aforementioned applications is incorporated herein by reference.

FIELD

The present application generally relates to medical devices and, in particular, to a stent with one or more open channels formed on its exterior surface.

BACKGROUND

In medical terms, a stent is a man-made "tube" inserted into a natural passage or conduit in the body to prevent, or counteract, a disease-induced, localized flow constriction. The term may also refer to a tube used to temporarily hold such a natural conduit open to allow access for surgery. Stents include vascular and non-vascular stents. Vascular stents are designed for applications in the vascular system, such as arteries and veins. Non-vascular stents are used in other body lumens such as biliary, colorectal, esophageal, ureteral and urethral tract, and upper airway.

Stents are available in permanent and temporary varieties. Stent duration is heavily influenced by the construction material. For example, metal stents typically have a much longer use life than plastic stents. The stent body typically has a central lumen that allows blood or other body fluid to flow through the stent. A common problem with the current stents is that they routinely migrate and clog, thus requiring additional procedures for extraction and/or replacement. There exists a need for improved stents that are easy to make and safe to use.

In chronic pancreatitis, a fibrotic duct stricture is a common complication and a therapeutic challenge. Drainage of an obstructed duct becomes mandatory because the intraductal pressure created by the stricture causes severe pain. At present, these fibrotic strictures are endoscopically treated by the sequential placement of multiple plastic stents for a period of six to twelve months with stent exchanges approximately every three months. These procedures are expensive and can increase risks for patients suffering from comorbidities.

The present application provides a biodegradable stent device, particularly for biliary or pancreatic placements, having superior properties for supporting a vessel, duct or lumen and optimizing the flow of bodily fluids through the use of two external longitudinal channels that spiral around the device.

SUMMARY

One aspect of the present application relates to a stent comprising an elongated body composed of a biodegradable material having a proximal end, a distal end, two open spiral channels formed on the exterior surface of said body to provide fluid communication between said proximal end and said distal end, and a central lumen open at the proximal and distal ends of the stent for the passage of a guide wire.

Another aspect of the present application relates to a stent comprising an elongated body composed of a bioabsorbable polymer and having a proximal end, a distal end, two open spiral channels formed on the exterior surface of said body to provide fluid communication between said proximal end and said distal end, wherein at least one open spiral channel has a rotation rate of at least 1 twist per inch, and a central lumen open at the proximal and distal ends of the stent for the passage of a guide wire.

Still another aspect of the present application relates to a stent comprising an elongated body composed of a bioabsorbable polymer and having a proximal end, a distal end, two open spiral channels formed on the exterior surface of said body to provide fluid communication between said proximal end and said distal end, wherein at least one open spiral channel has a rotation rate of between about 1.5 and 3.5 twists per inch, and a central lumen open at the proximal and distal ends of the stent for the passage of a guide wire.

Yet another aspect of the present application relates to a stent comprising an elongated body composed of a bioabsorbable polymer and having a proximal end, a distal end, a pair of open spiral channels formed on the exterior surface of said body to provide fluid communication between said proximal end and said distal end, wherein said spiral channels have a rotation rate of at least about 1 twist per inch, and a central lumen open at the proximal and distal ends of the stent for the passage of a guide wire.

Another aspect of the present application relates to a method of emplacing a stent in a subject in need thereof, comprising: establishing an entry portal into a vessel, duct or lumen contiguous with a target site for stent placement, advancing a guide wire through the entry portal and said vessel, duct or lumen contiguous to said target site, and advancing the stent along said guide wire to the target site. The stent comprises an elongated body composed of a bioabsorbable polymer and having a proximal end, a distal end, two open spiral channels formed on the exterior surface of said body to provide fluid communication between said proximal end and said distal end and a central lumen open at the proximal and distal ends of the stent for the passage of a guide wire. The method further comprises the step of withdrawing the guide wire.

Still another aspect of the present application relates to a kit for stent placement. The kit comprises a stent comprising an elongated body composed of a bioabsorbable polymer and having a proximal end, a distal end, two open spiral channels formed on the exterior surface of said body to provide fluid communication between said proximal end and said distal end and a central lumen open at the proximal and distal ends of the stent for the passage of a guide wire. The kit also comprises a guide wire.

BRIEF DESCRIPTION OF THE DRAWINGS

The present application can be better understood by reference to the following drawings, wherein like references numerals represent like elements. The drawings are merely exemplary to illustrate certain features that may be used singularly or in combination with other features and the present application should not be limited to the embodiments shown.

FIGS. 4A and 4B are diagrams showing two engagement mechanisms among the stent, the guide wire and the pusher tube.

FIGS. 20A-D show another embodiment of a stent of the present application.

FIGS. 21A-H show another embodiment of a stent of the present application.

DETAILED DESCRIPTION

Figure 1A:
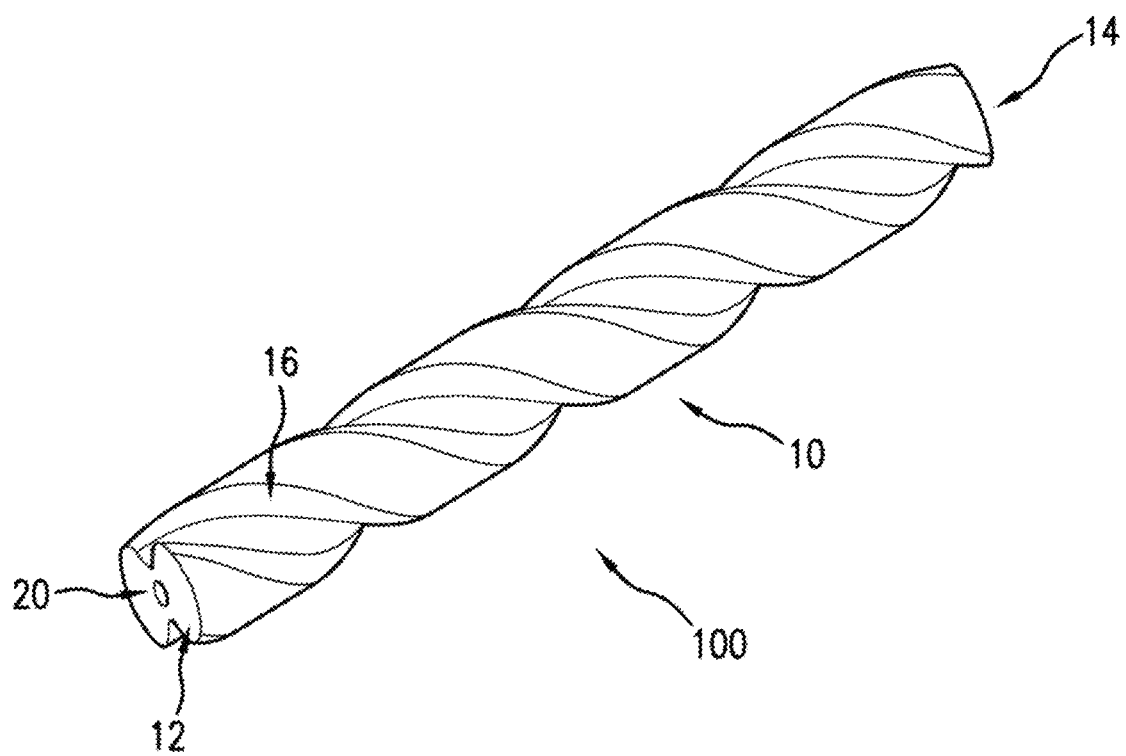
FIG. 1A is a diagram showing an embodiment of the stent of the present application.

The practice of the subject matter of the present application will employ, unless otherwise indicated, conventional medical devices and methods within the skill of the art. Such techniques are explained fully in the literature. All publications, patents and patent applications cited herein, whether supra or infra, are hereby incorporated by reference in their entirety.

One aspect of the present application relates to a stent that contains an elongated stent body having a proximal end, a distal end, and two open spiral channels formed on the exterior surface of the elongated stent body to provide fluid communication from the proximal end to the distal end of the stent.

As used herein, the term "stent" refers to a device which is implanted within a bodily lumen to hold open the lumen or to reinforce a small segment of the lumen. Stents can be used for treating obstructed vessels, biliary ducts, pancreatic ducts, ureters, or other obstructed lumens, fractured canals, bones with hollow centers and/or for delivering various drugs through controlled release to the particular lumen of interest.

In some embodiments, the stent of the present application is comprises, or composed of, a biodegradable material. The term "biodegradable" refers to materials that are capable of being completely degraded and/or eroded when exposed to bodily fluids such as blood and can be gradually resorbed, absorbed and/or eliminated by the body. "Biodegradable" is intended to broadly include biologically erodable, bioabsorbable, and bioresorbable materials such as alloys and polymers that are broken down and/or eliminated by the body. In some embodiments, at least a portion of the surface of the stent of the present application is polymeric. In some embodiments, the stents of the present application are fabricated partially or completely from a biodegradable, bioabsorbable, or biostable polymer. In some embodiments, a polymer-fabricated stent may serve as a substrate for a polymer-based coating. The polymer-based coating may contain, for example, an active agent or drug for local administration at a diseased site. In some embodiments, an active agent or a drug is incorporated into a body of a polymer-fabricated stent.

The open channel should be large enough to allow unobstructed or normal flow of various body fluids such as blood, bile or urine or other luminal material/liquids on the outer aspect of the stent. The open channel may have a cross section area that is of any shape or depth. The channel could be V shapes, U shaped, or with a rising or falling pitch, of an even depth or one that is of varying widths, depths, varying and circumferential rotations changing at various points over the length of the device. The channel can be a straight channel or a spiral channel. Multiple channels may be formed on the exterior surface or the inner surface of the elongated stent body. The channel(s) may also be designed with a geometry that would help the stent to remain in place. A double-channel helical twist design refers to a stent with two open spiral channels on the exterior surface of the stent body to provide fluid communication between the opposing ends of the stent body (proximal end and distal end). The stent of the present application in a preferred embodiment has a double-channel helical twist design.

The shape, length and diameter of the stent body are application dependent. The elongated stent body can be straight or curved or in the shape of multiply connected and angulated curves. Each type of stent is designed to fit within a specific part of the anatomy. Therefore, the shape, length, and diameter of stents differ by type to accommodate and support different sized lumens and different clinical needs. For example, each major stent application, such as vascular, pancreatic, ureteral, or metacarpal canal, other hollow bone structures and other stent, requires a different diameter and shape to enable placement, to remain in place after placement, to stabilize and support the anatomy it is placed in, and to allow conformance to the normal anatomy. As used herein, the diameter of a stent refers to the width across the shaft of the stent body, which is also referred to as the "major diameter." In one embodiment, the stent has a uniform diameter. In another embodiment, the stent has a variable diameter. In one embodiment, the diameter at the distal end is smaller than the diameter at the proximal end. In another embodiment, the diameter at the proximal end is smaller than the diameter at the distal end. In yet another embodiment, the diameters at the distal end and the proximal end are both smaller than the diameter at the middle section of the stent.

The stent body may further include a center lumen to accommodate a guide wire. This center lumen may provide additionally flow throughput after the removal of guide wire.

One aspect of the present application relates to a stent comprising an elongated body having a proximal end, a distal end, at least one open spiral channel formed on the exterior surface of said body to provide fluid communication between said proximal end and said distal end, and a central lumen open at the proximal and distal ends of the stent for the passage of a guide wire.

In some embodiments, the body is composed of a bioabsorbable polymer.

In other embodiments, the at least one open spiral channel has a rotation rate of between about 1.5 and 2.5 twists per inch.

In still other embodiments, the at least one open spiral channel has a rotation rate of at least about 2 twists per inch.

In some embodiments, the stent comprises two open spiral channels formed on the exterior surface of said body. In some further embodiments, the channels are on opposite sides on the exterior surface of said body.

In some embodiments, the body further comprises an anti-migration device.

In other embodiments, the body further comprises a biological agent. In some further embodiments, the biological agent is selected from the group consisting of chemotherapeutic agents, antimicrobial agents and gene transfer agents.

In particular embodiments, the stent has a pre-implantation diameter $D_{pre}$ and is in situ expandable upon absorption of a body fluid to a post-implantation diameter $D_{post}$, wherein $D_{post}$ is greater than $D_{pre}$.

In some embodiments, the stent comprises a radio-opaque substance.

Another aspect of the present application relates to a stent comprising an elongated body composed of a bioabsorbable polymer and having a proximal end, a distal end, at least one open spiral channel formed on the exterior surface of said body to provide fluid communication between said proximal end and said distal end, wherein said at least one open spiral channel has a rotation rate of at least 1 twist per inch, and a central lumen open at the proximal and distal ends of the stent for the passage of a guide wire.

In some embodiments, the bioabsorbable polymer comprises PEG and p-dioxanone.

In other embodiments, the bioabsorbable polymer comprises PPDO.

In still other embodiments, the bioabsorbable polymer comprises PLA, trimethylene carbonate and caprolactone.

In some embodiments, the at least one open spiral channel has a rotation rate of at least about 2 twists per inch.

In particular embodiments, the stent comprises two open spiral channels formed on the exterior surface of said body. In some further embodiments, the channels are on opposite sides on the exterior surface of said body.

Still another aspect of the present application relates to a stent comprising an elongated body having a proximal end, a distal end, at least one open spiral channel formed on the exterior surface of said body to provide fluid communication between said proximal end and said distal end, wherein said at least one open spiral channel has a rotation rate of between about 1.5 and 3.5 twists per inch, and a central lumen open at the proximal and distal ends of the stent for the passage of a guide wire.

In some embodiments, the stent comprises two open spiral channels formed on the exterior surface of said body. In some further embodiments, the channels are on opposite sides on the exterior surface of said body.

Yet another aspect of the present application relates to a stent comprising an elongated body composed of a bioabsorbable polymer and having a proximal end, a distal end, a pair of open spiral channels formed on the exterior surface of said body to provide fluid communication between said proximal end and said distal end, wherein said spiral channels have a rotation rate of at least about 1 twist per inch, and a central lumen open at the proximal and distal ends of the stent for the passage of a guide wire.

In some embodiments, the channels are on opposite sides on the exterior surface of said body.

Another aspect of the present application relates to a method of emplacing a stent in a subject in need thereof, comprising: establishing an entry portal into a vessel, duct or lumen contiguous with a target site for stent placement, advancing a guide wire through the entry portal and said vessel, duct or lumen contiguous to said target site, and advancing the stent along said guide wire to the target site. The stent comprises an elongated body having a proximal end, a distal end, two open spiral channels formed on the exterior surface of said body to provide fluid communication between said proximal end and said distal end and a central lumen open at the proximal and distal ends of the stent for the passage of a guide wire. The method further comprises the step of withdrawing the guide wire.

Still another aspect of the present application relates to a kit for stent placement. The kit comprises a stent comprising an elongated body having a proximal end, a distal end, two open spiral channels formed on the exterior surface of said body to provide fluid communication between said proximal end and said distal end and a central lumen open at the proximal and distal ends of the stent for the passage of a guide wire. The kit also comprises a guide wire.

In one embodiment, the stent is naturally formed by braiding multiple filaments together. In another embodiment, the stent is made with a center rod/hub/cam having one or more sinusoidal channels running through the exterior surface of the center rod, similar to that of a drill bit.

The stent of the present application can be expandable. In one embodiment, the stent is of two different diametrical dimensions due to radial deformation of its elastic elements. Before being positioned at the place of reconstruction, the stent is deformed/compressed/folded so as to minimize its diametrical dimension. Then the stent is placed, in the deformed state, inside a transporting means by arranging it on a special setting bulb. Once the stent has been transported to the place of reconstruction, the setting bulb is expanded so that the stent diameter is maximized. In another embodiment, the stent has a plurality of flexible or foldable channel walls or leaflets extending from the center rod/hub/cam. The channel walls or leaflets are kept in a folded position during the delivery process and are released only at the treatment site.

In one embodiment, the stent is delivered to the treatment site in a body lumen with a pusher rod that pushes the stent through a body channel into place. The pusher rod travels over a guide wire. The pusher rod is designed in such a way to attach to the ends of the stent to assist with directing the delivery. In one embodiment, the pusher rod interlocks with the proximal end of the stent in a male/female fashion, much the same way a wrench fits over a nut.

The stent of the present application can replace plastic and biliary and/or pancreatic stents with the additional benefit of being biodegradable, which eliminates the use of endoscopic retrograde cholangiopancreatography (ERCP) for subsequent stent removal. In particular embodiments, the stent of the present application may have one of three or more degradation profiles, including a fast degradation profile (minimal strength retention of 12 days), a medium degradation profile (minimal strength retention of 25 days) and a slow degrading profile (minimal strength retention of 12 weeks). The strength retention is defined by the presence of at least 10% of the initial strength parameter (e.g. the stent remains intact with no breaks, tested in a simulated degradation model).

In some embodiments, the stent with a fast degradation profile contains a polymer of 20% PEG and 80% p-dioxanone and is impregnated with $BaSO_4$. In one embodiment, the stent with a fast degradation profile contains by weight 16.8% PEG, 67.2% p-dioxanone (in the form of a 20%/80% PEG/p-dioxanone copolymer) and 16% BaSO4 (barium sulfate), In some embodiments, the stent with a medium degradation profile contains a polymer of 100% poly(para-dioxanone) and is impregnated with $BaSO_4$. In one embodiment, the stent with a medium degradation profile contains by weight 84% Poly(para-dioxanone) and 16% BaSO4. In some embodiments, the stent with a slow degradation profile contains a copolymer of 74% lactide, 15% trimethylene carbonate, 11% caprolactone and is impregnated with $BaSO_4$. In one embodiment, the stent with a slow degradation profile contains by weight 62.16% lactide, 12.6% trimethylene carbonate, 9.24% caprolactone (in the form of a 74%/15%/11% copolymer) and 16% BaSO4.

In some embodiments, the stent of the present application experiences initial surface degradation upon implantation, which allows for bile cleansing (one of ordinary skill will understand that certain polymers will degrade by surface erosion before bulk degradation, no special coating or composition is required). The stent of the present application also uses a double-channel helical twist design to allow bile flow on the outside of the stent. In comparison to other stents, the stent of the present application provides better simulated flow rates, better simulated migration resistance and better crush resistance.

Figure 1B:
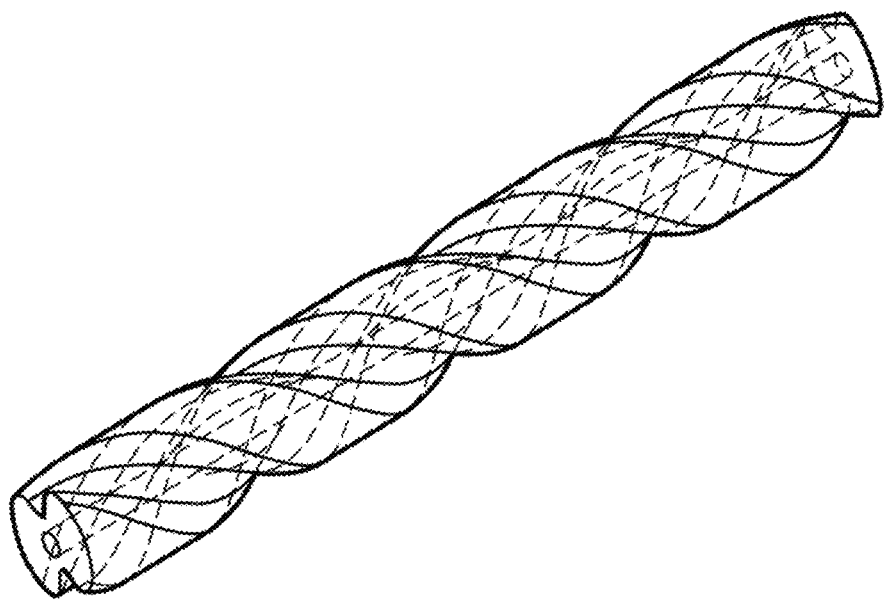
FIG. 1B is a see-through illustration of FIG. 1A.

FIG. 1A is a diagram showing an embodiment of the stent of the present application. In this embodiment, stent 100 has an elongated body 10 with a proximal end 12 and a distal end 14. Two sinusoidal channels 16 are formed on the exterior surface of the elongated body 10, extending from the proximal end 12 to the distal end 14 in a fashion similar to the grooves on a drill head. The channels may have beveled edges to facilitate fluid flow inside the channels. The channels can be of varying depths and lengths. The ends of the stent body can be of various shapes including conical shape. FIG. 1B is a see through drawing of FIG. 1A. The two-channel design allows for two channels on the exterior surface of the stent to run in parallel from one end to the other or to criss-cross to allow for increased fluid flow as well as the ability to increase side branch flow of the main stented channel.

A center lumen 20 allows the stent 100 to slide into the place of implantation through a guide wire.

Figure 2:
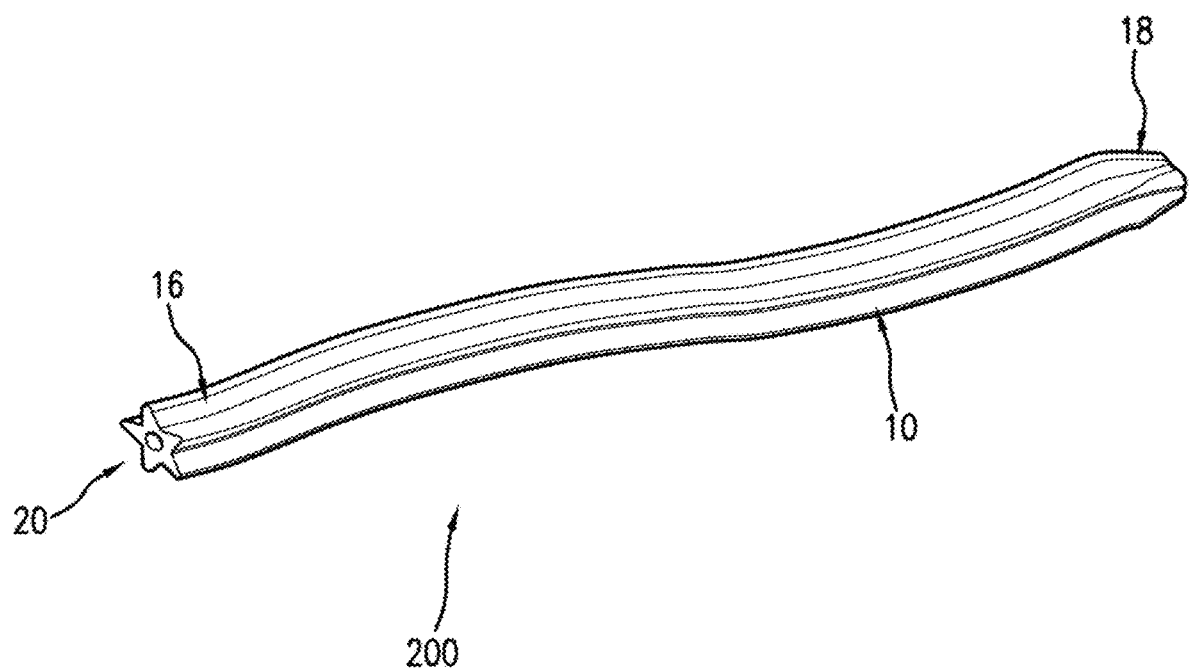
FIG. 2 is a diagram showing a stent with a sinusoidal shaped stent body.

FIG. 2 shows another embodiment of the stent of the present application. In this embodiment, stent 200 has a modified sinusoidial body shape to improve flexibility, allow for varying flow dynamics, and facilitate contour and wall adherence to the lumens. The multiple V shaped channels 16 allow for the flow of various body fluids. The diameter of the internal lumen 20 and the outer diameter of the stent body can be changed based on the need for various luminal dimensions, shapes, flows, and biomechanics. The tapered tip 18 facilitates advancement of the stent inside a body lumen.

Figure 13:
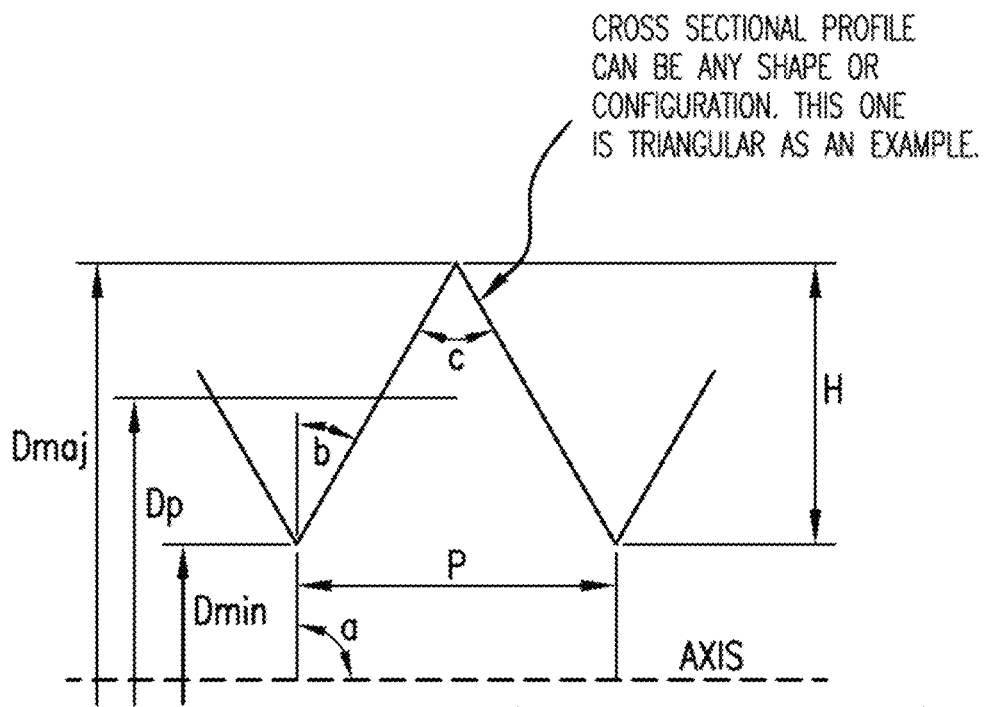
FIG. 13 shows the cross section of an embodiment of a stent of the present application.
Figure 14:
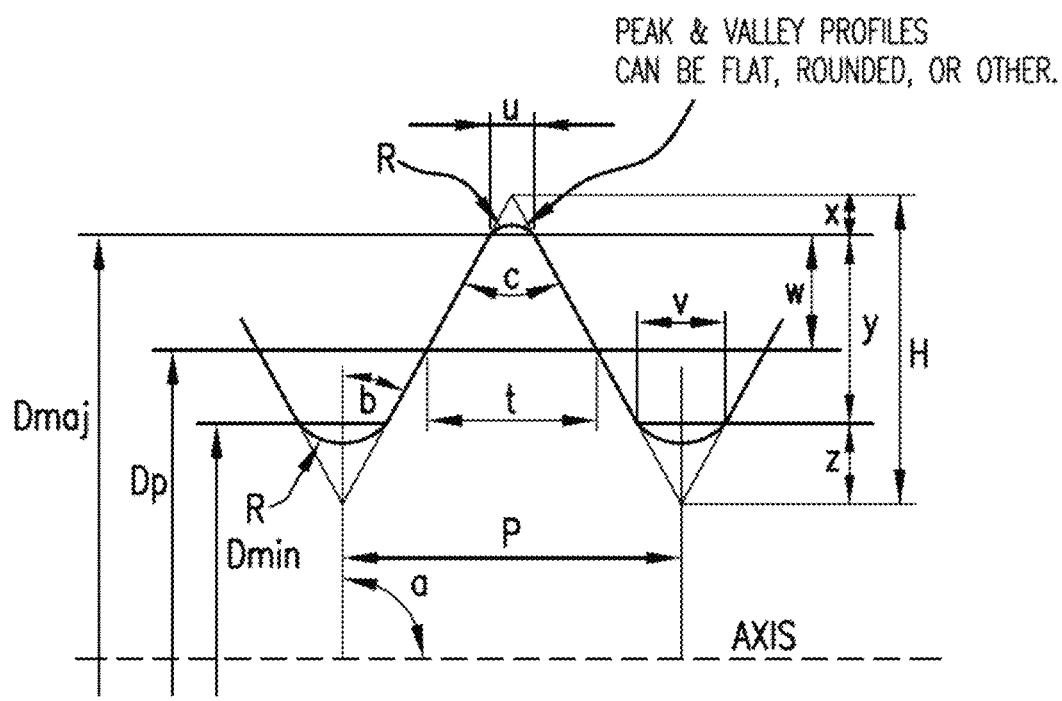
FIG. 14 shows the cross section of another embodiment of a stent of the present application.

FIGS. 13 and 14 show cross-sections of V-shaped channel and channel walls. The channels can be of varying depths and varying widths to change the volume and speed of fluid flow. The bottom of the channel can be rounded or tapered or formed by a direct angle.

Figure 3:
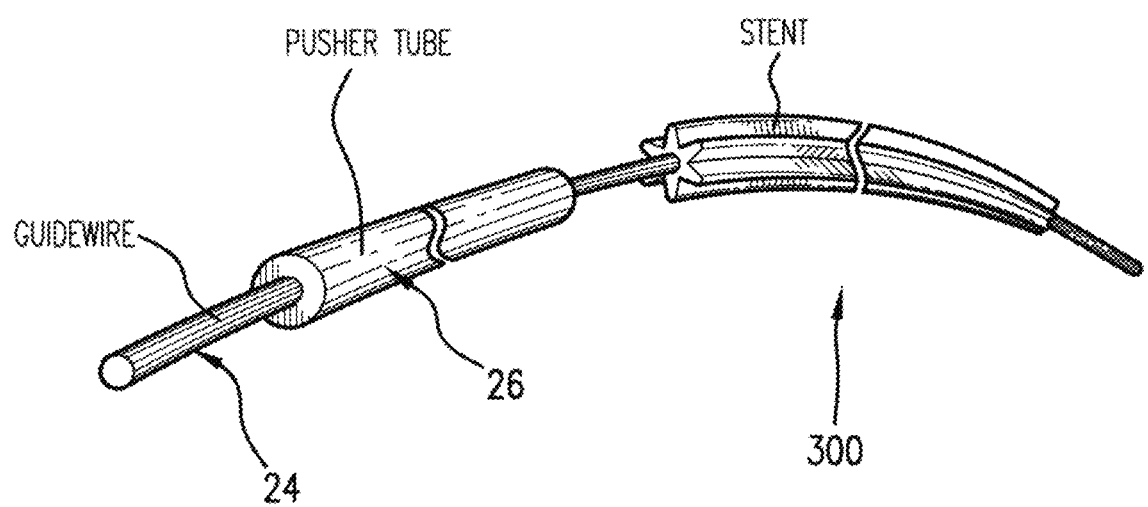
FIG. 3 is a diagram showing an assembly of a stent with a guide wire and a pusher tube.

The stent of the present application may be implanted with procedures well known to a person of ordinary skill in the art. Examples of such procedures include, but are not limited to, standard percutaneous approach using a guide wire, endoscopic retrograde cholangiopancreatography (ERCP) placement procedures, and other radiographic/angiographic procedures. FIG. 3 shows an assembly of a stent 200 with a guide wire 24 and a pusher tube 26. FIG. 4 shows several engagement mechanisms among the stent 300, the guide wire 24 and the pusher 26. In FIG. 4A, the pusher tube has several fingers to hold the stent 300 like a hand or clamp. In FIG. 4B, the pusher 26 interlocks with the stent 300 in a male/female fashion to ensure security of positioning and delivery of the stent 300. The interlocking mechanism may involve a male to female interconnect of various shapes, sizes, or dimensions.

Figure 5A:
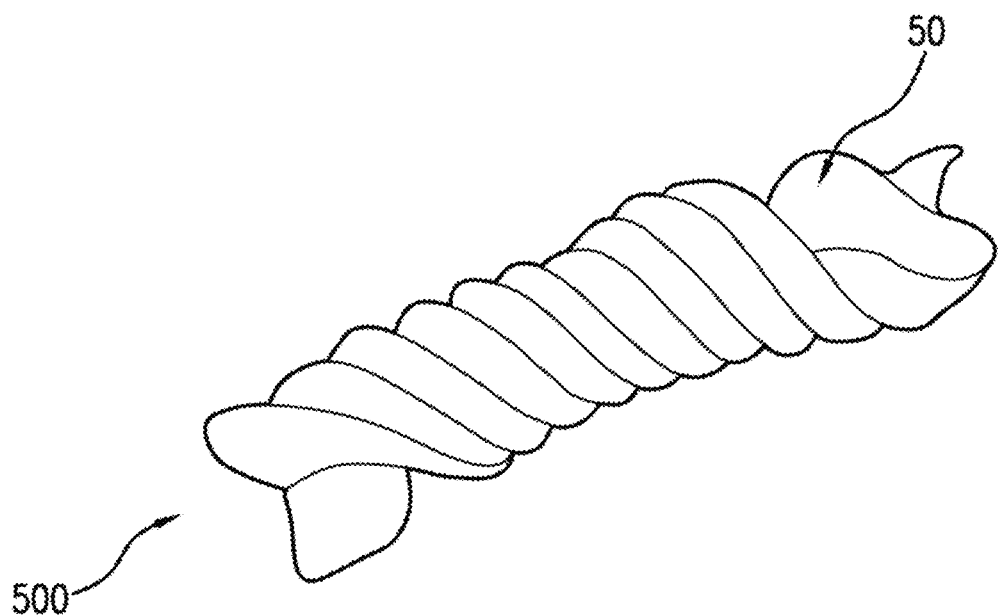
FIGS. 5A and 5B show an embodiment of an expandable stent.
Figure 5B:
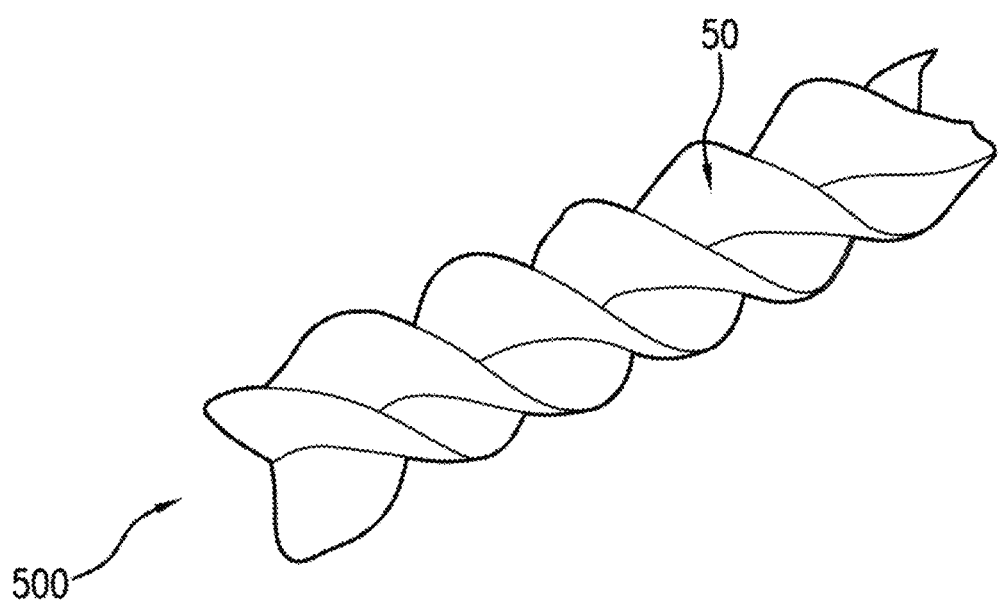

FIGS. 5A and 5B show an embodiment of an expandable stent 500 with compressible channel walls 50. In a closed state (FIG. 5A), the channel walls 50 are compressed or twisted against each other to reduce stent diameter. Once the stent has been transported to the treatment site, the channel walls are restored to their natural shape (FIG. 5B).

Figure 6A:
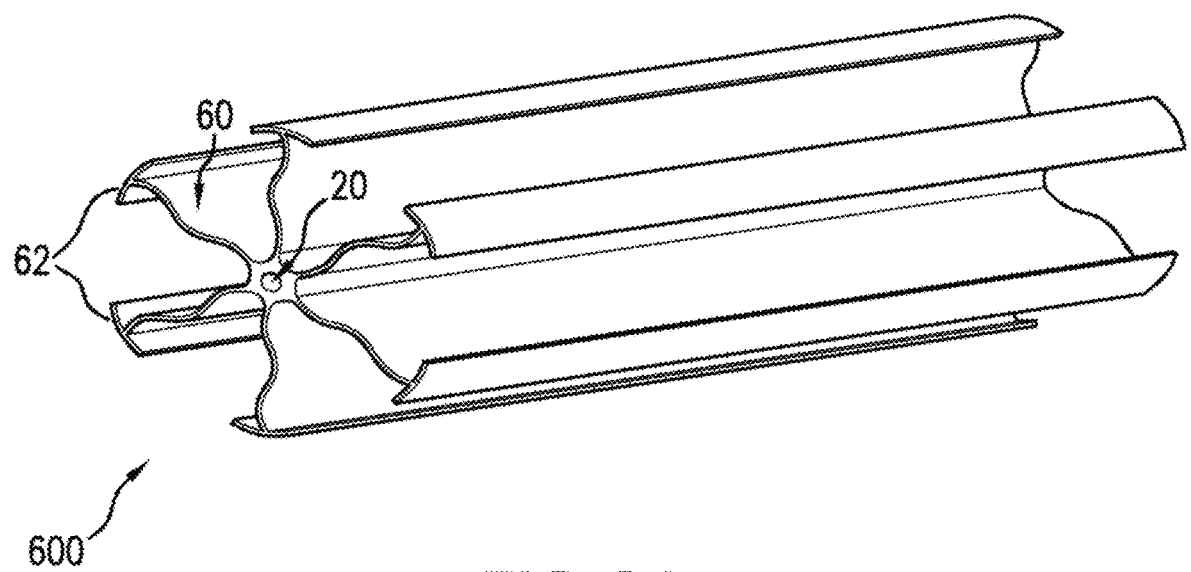
FIGS. 6A and 6B show another embodiment of an expandable stent.
Figure 6B:
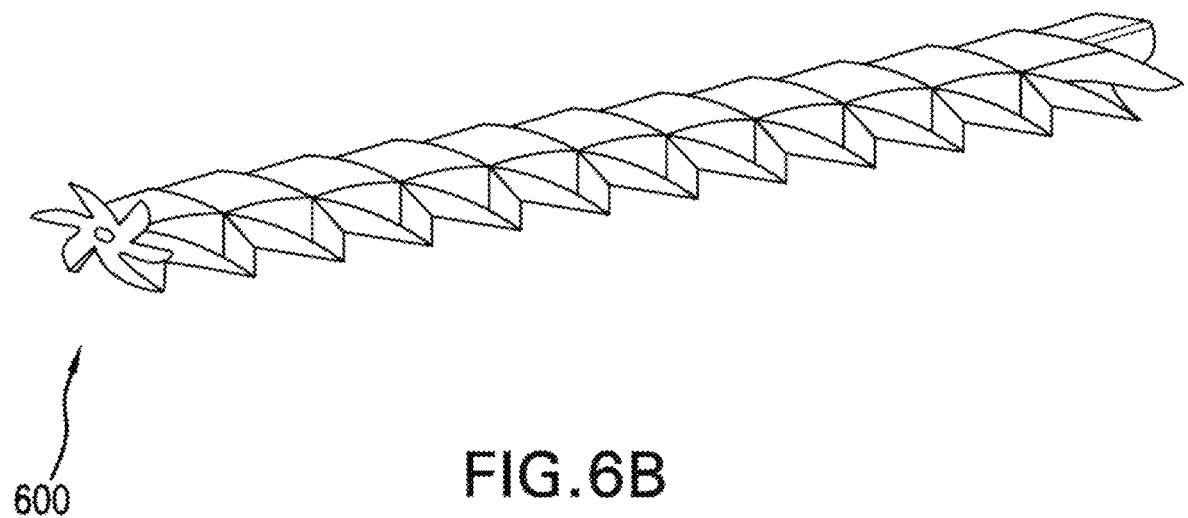

FIGS. 6A and 6B show another embodiment of an expandable stent 600 with foldable leaflets 60. In an extended state, the thin leaflets 60 allow for unobstructed flow of body fluid (FIG. 6A). In one embodiment, the leaflets 60 are contoured and aligned in a way to increase the flow speed of the body fluid or to provide minimal drag. The impedance of the flow volumes and the velocity can be modulated by changing the angles and contour of the leaflets. Additionally the interconnecting supports can be thicker at the cam to provide different levels of stability and rigidity for the bracing arms 62, which help support the structure they are placed in. The bracing arms 62 can be connected at anywhere along their diameter and the change in connection points will have an impact in the rigidity of the support of the lumen, the ability of the device to flex with the normal body movement of the lumen, and will change the minimal diameter the device can be collapsed in. The stent 600 may further contain a center lumen 20.

As shown in FIG. 6B, the leaflets 60 may be rotated pivotally (e.g., clockwise) to collapse into each other to reduce the size of the stent to facilitate implantation. Once in place, the stent may be rotated in an opposite direction (e.g., counter clockwise) to restore to its extended state. The tip of the stent 600 can be titled or coned or shaped into various configurations to allow for access to different body lumens. The opened leaflets 60 further have the benefit to prevent migration of the stent 600.

Figure 7A:
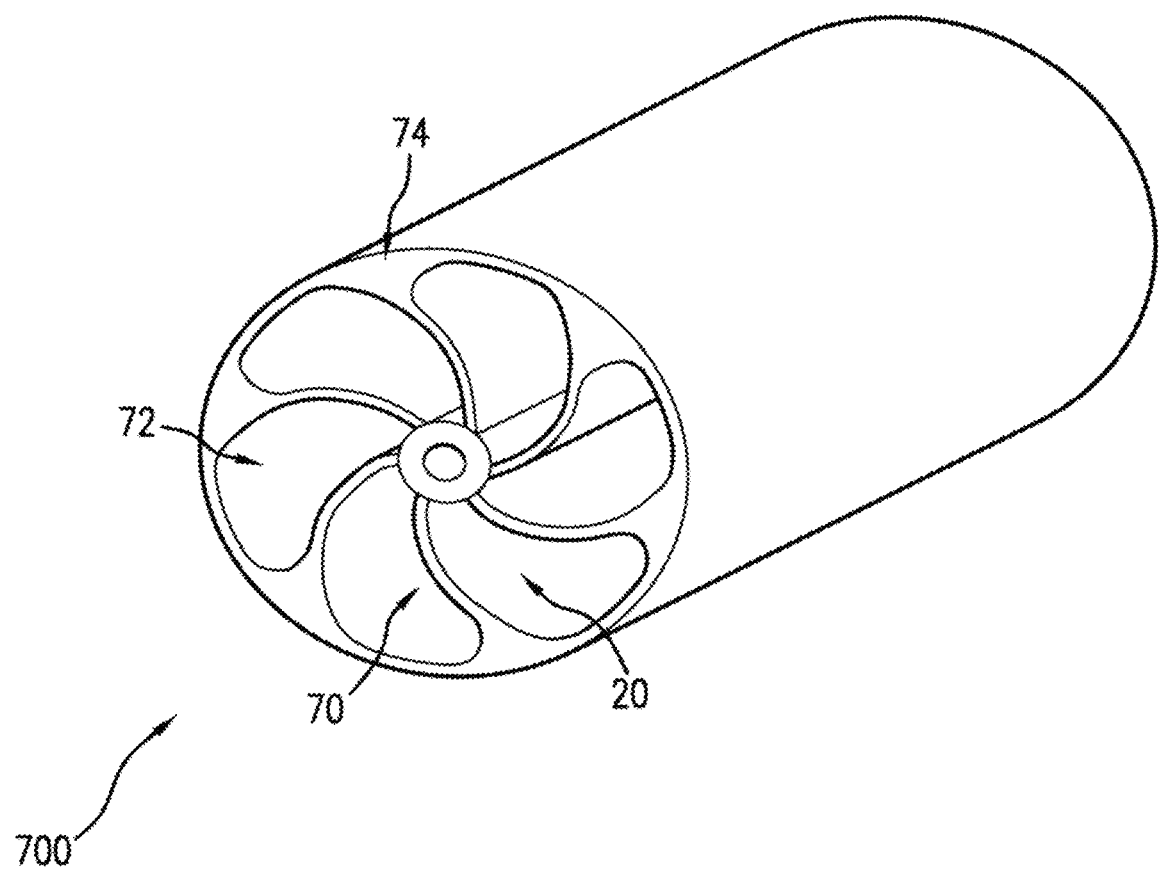
FIGS. 7A and 7B show another embodiment of an expandable stent.
Figure 7B:
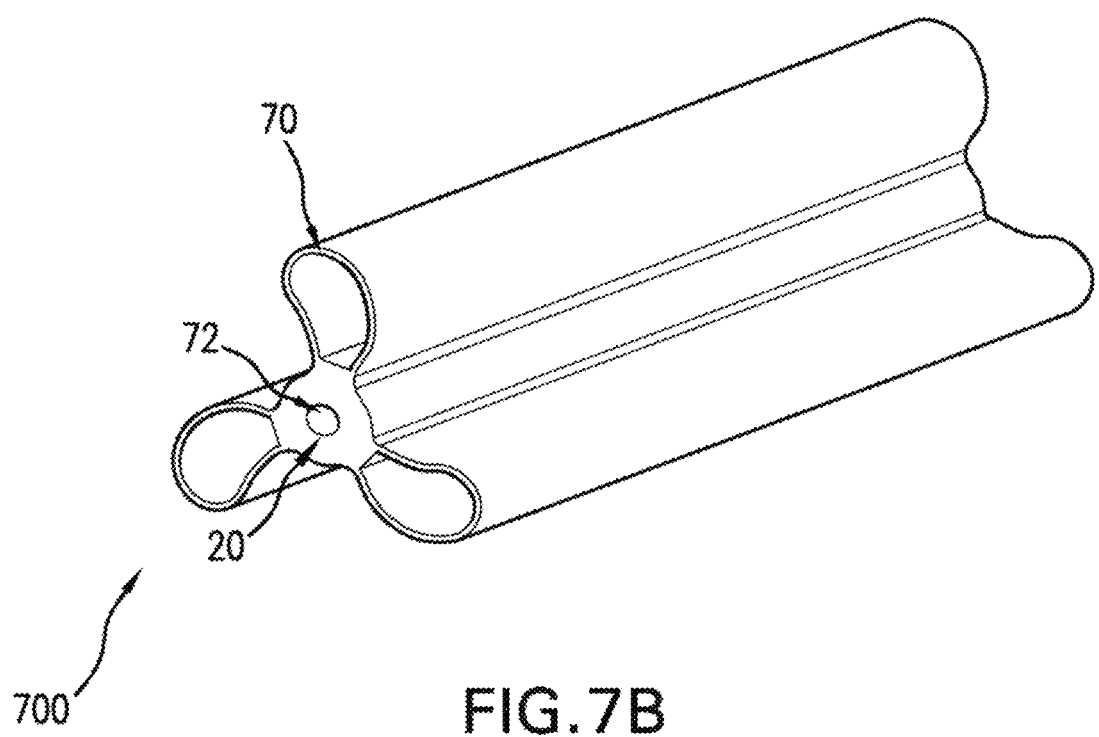

FIGS. 7A and 7B show another embodiment. In this embodiment, the expandable stent 700 has closed connections around each alternating leaflet 70 to allow for changes in flexibility, radial force, compression resistance, and absorption. The leaflets 70 have a sinusoidal pattern and can be thicker at the attachment to inner cam 72 to allow for variations of rigidity. The outer cam 74 prevents tissue growth inside the stent body and increases contact area between the stent 700 and inner wall of the body lumen. The thickness of outer cam 74 is application dependent. The outer cam 74 may also be beveled. The stent 700 may have a removal grip attached to the end of center lumen 20 to allow for easy removal of the stent 700.

FIG. 7B shows another embodiment of the stent 700. In this embodiment, the leaflets 70 are connected to the cam 72 and can be compress down towards the cam 74. The leaflets may have a hollow interior so that fluid may flow through and around the leaflets 70.

Figure 8A:
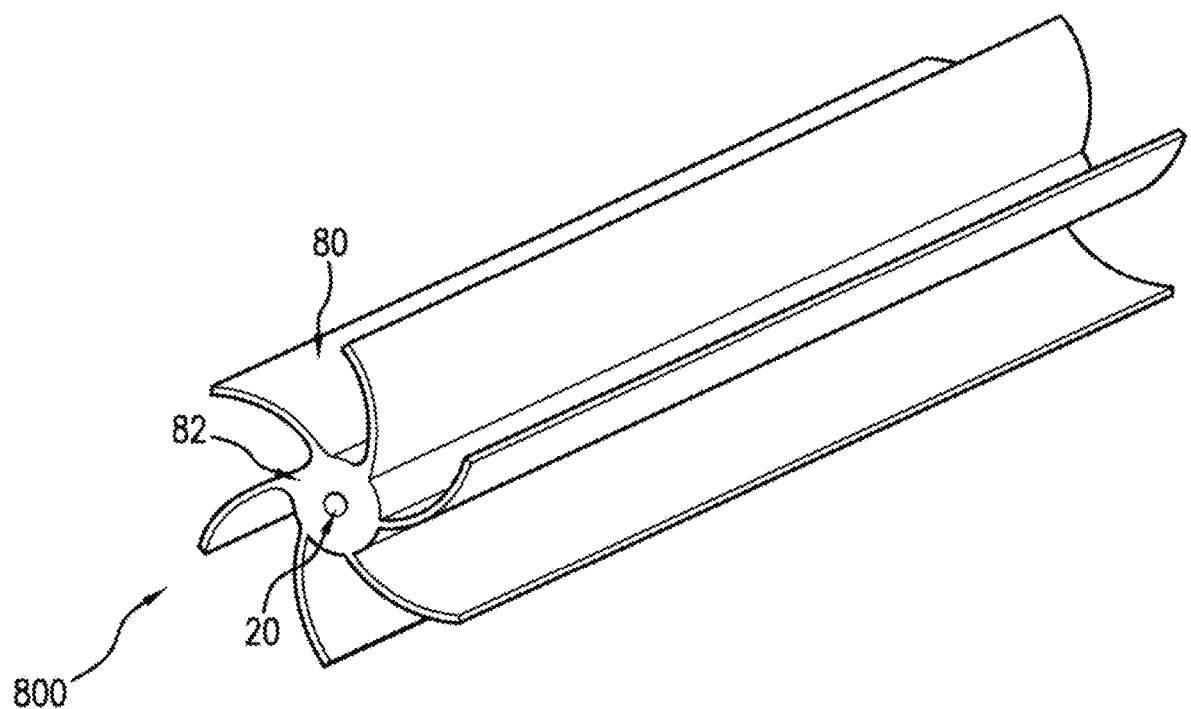
FIGS. 8A-8F show various embodiments of an expandable stent.

In another embodiment, stent 800 contains propeller-like leaflets 80 that are thicker at the base where they are attached to the cam or rod portion 82 of the stent 800. The leaflets 80 become thinner at the tip (FIG. 8A). The stent 800 may also have a sinusoidal shape to conform to a body lumen.

Figure 8B:
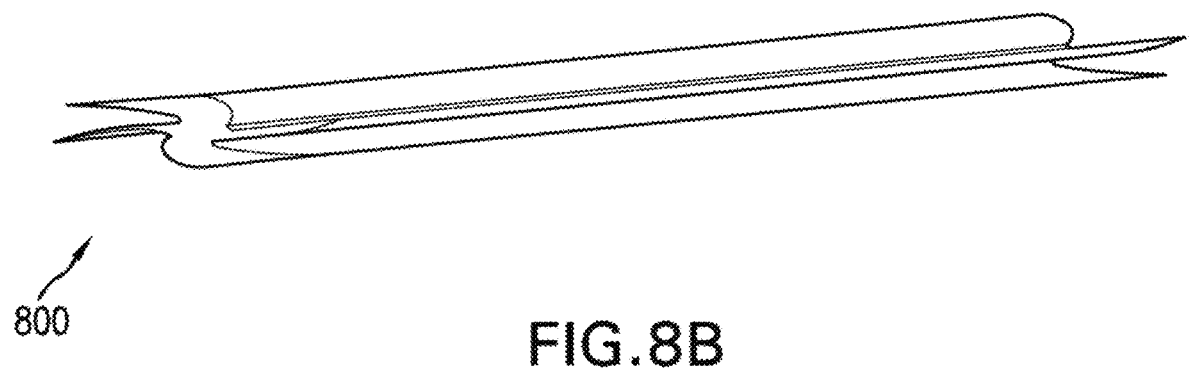

The propeller-like stent 800 may be constructed in such a way to allow unidirectional collapse of the leaflets to facilitate ease of passage through the working channel of an endoscope, bronchoscope, or through some other tubular delivery apparatus or opening by simply rotating the stent in a unidirectional manner and then reversing the technique to open the stent once it is in place. Additionally, the tip of the stent 800 may be shaped to allow for ease of collapse or insertion. FIG. 8B shows a stent 800 in a collapsed configuration.

Figure 8C:
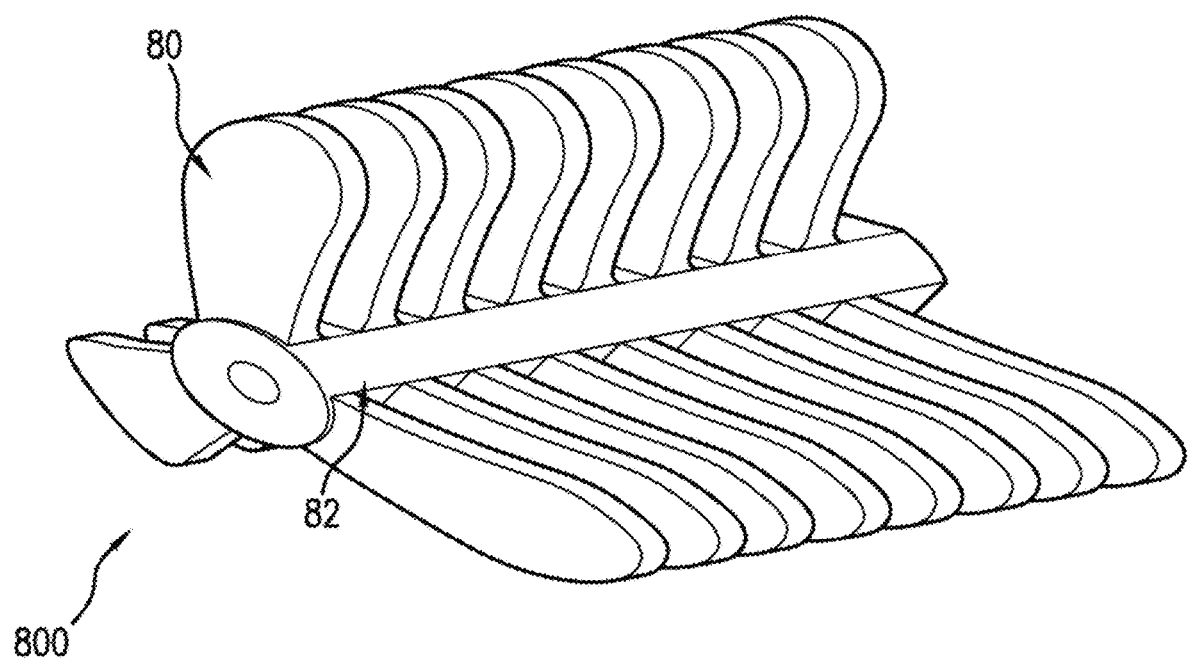
Figure 8D:
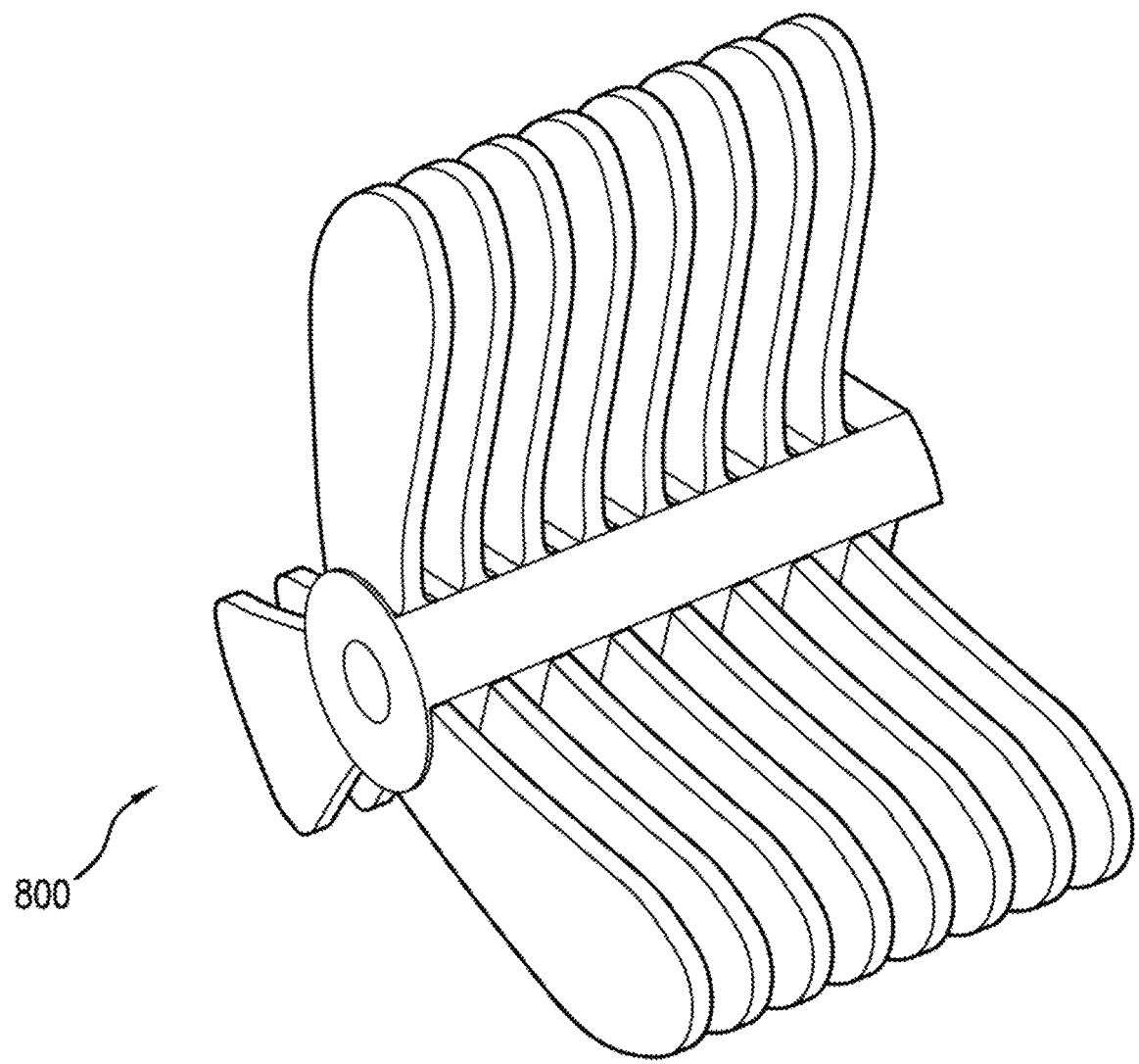

FIG. 8C shows another embodiment of the stent 800. In this embodiment, the leaflets 80 can be folded towards the cam or rod portion 82 of the stent body, in a manner similar to that of an umbrella. The leaflets 80 can be in any shape, such as round, oval, triangle etc. and will have a change in thickness at the base where the leaflets are connected to the cam 82 to allow you to change ease or rigidity of folding the device and passing it through and opening or channel. The unidirectional leaflets allow the device to be pushed through an opening and then pulled back to secure it in place. In another embodiment, the leaflets can be folded towards the cam or rod portion of the stent body, in a manner similar to that of an umbrella, a collapsing tree, or unidirectional or multidirectional folding leaflets of consistent or varying shapes. FIG. 8D shows the stent of FIG. 8C in a collapsed configuration.

Figure 8E:
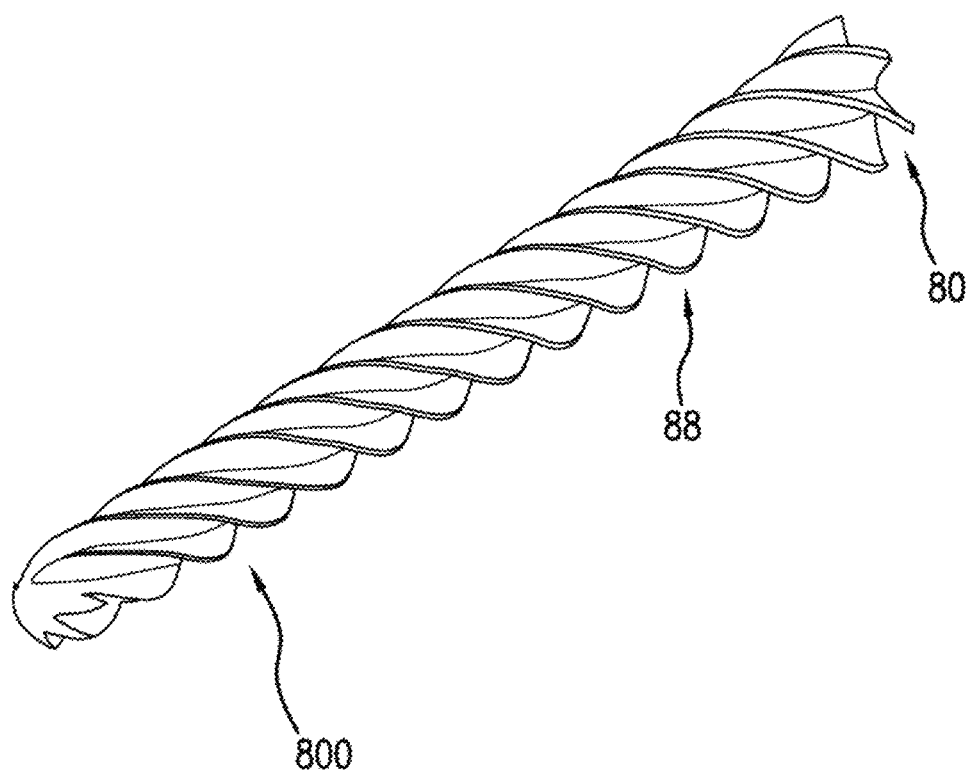
Figure 8F:
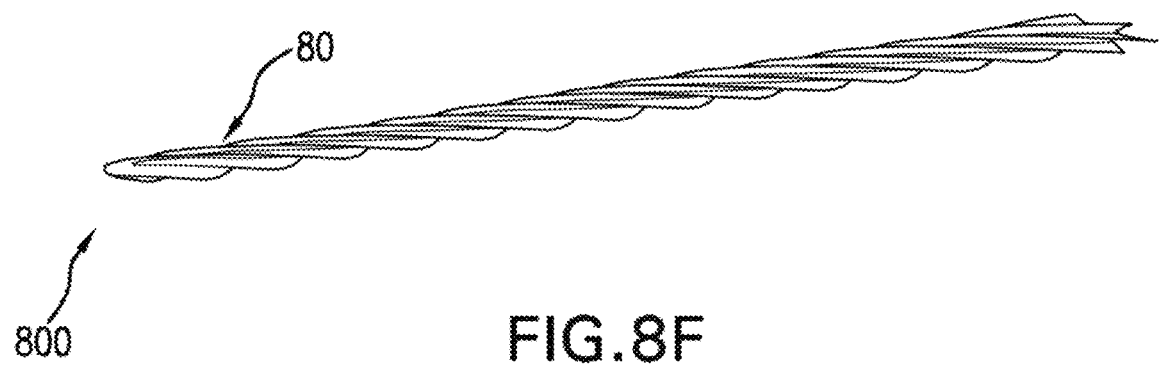

In another embodiment, the leaflets 80 of the stent 800 can be folded together by rotating along a common axis. FIGS. 8E and 8F show a stent 800 in open and folded configurations, respectively. In one embodiment, the stent 800 has a diameter of 1 cm in open configuration and a diameter of 1 mm in folded configuration. Depending on flow requirements, the channel 88 may have raps ranging from 5 to 100 degrees. In certain embodiments, the channel 88 may have raps of about 5-20 degrees, 20-40 degrees, 40-60 degrees, 60-80 degrees or 80-100 degrees. In certain embodiments, the channel has a rap of about 5 degrees, about 10 degrees, about 20 degrees, about 30 degrees, about 40 degrees, about 50 degrees, about 60 degrees, about 70 degrees, about 80 degrees, about 90 degrees, or about 100 degrees.

In another embodiment, a device has a portion of the device and stent and its leaflets collapsible so that some portion of the device (e.g., 1%) would have uni-direction leaflets and the remainder would have the opposite facing leaflets or directions such as seen on the different blades of a saw. In yet another embodiment, the leaflets are alternating in directions so as to prevent migration of the expanded stent.

Figure 9A:
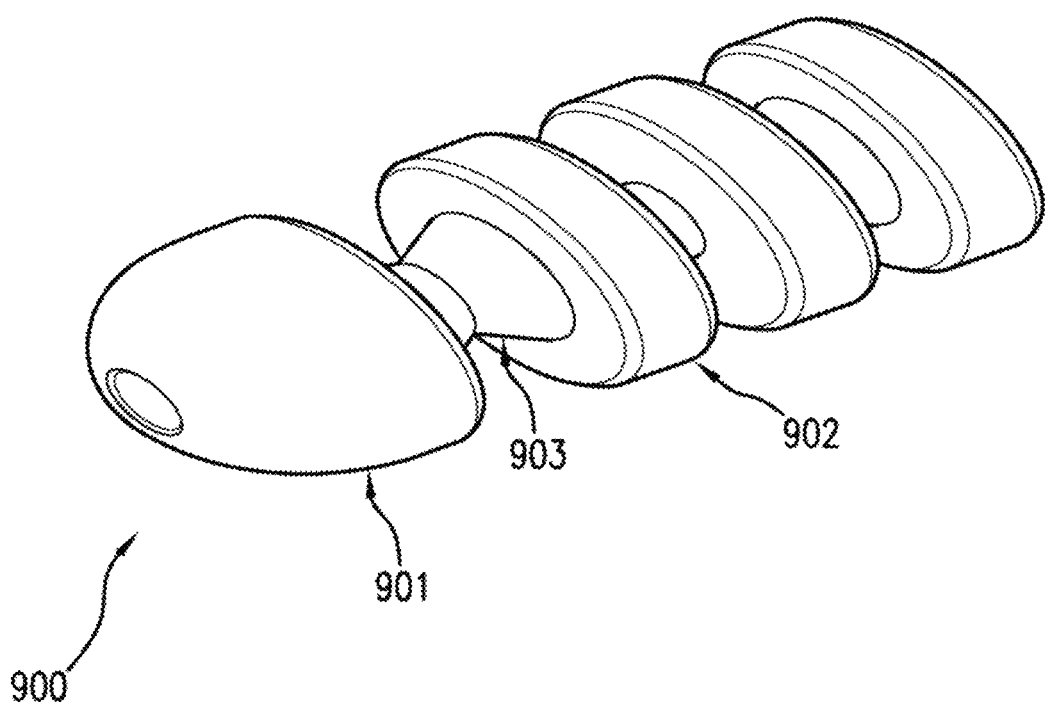
FIGS. 9A-9C show several embodiments of a stent with an outer frame.
Figure 9B:
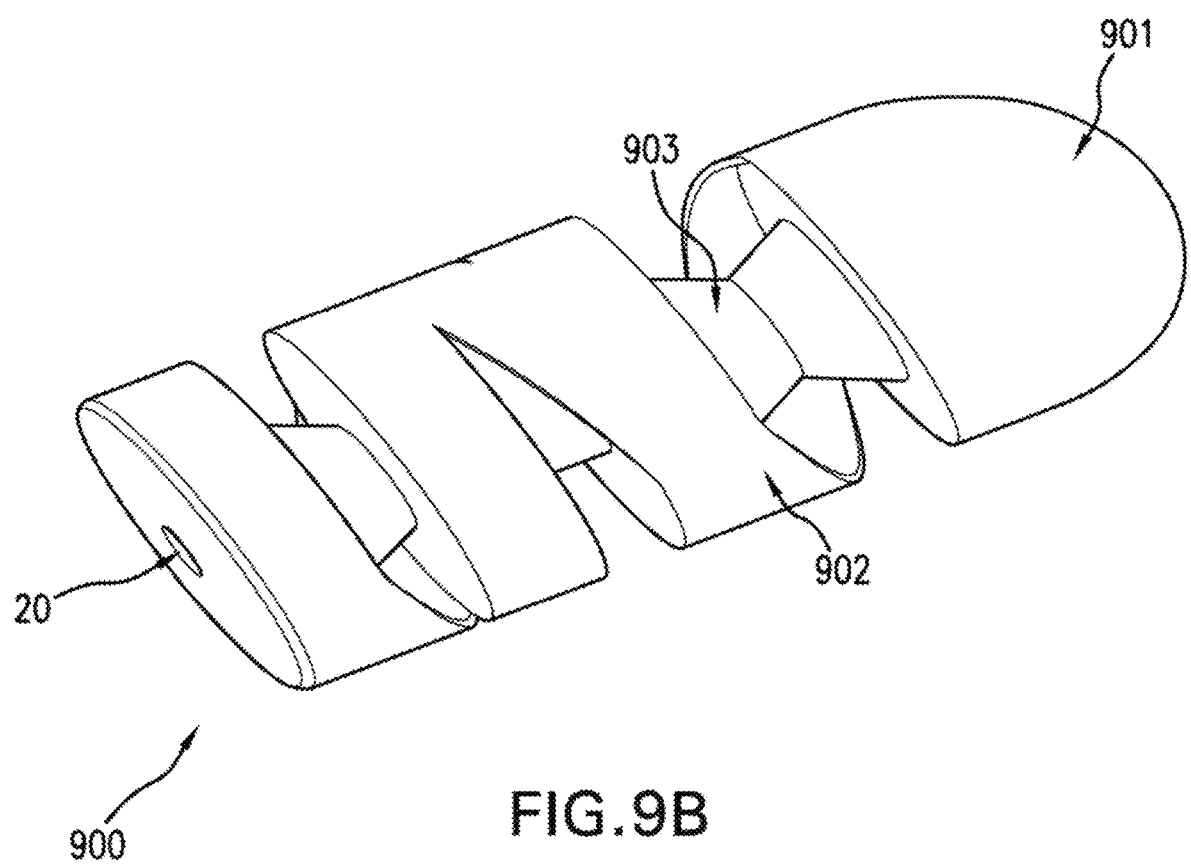
Figure 9C:
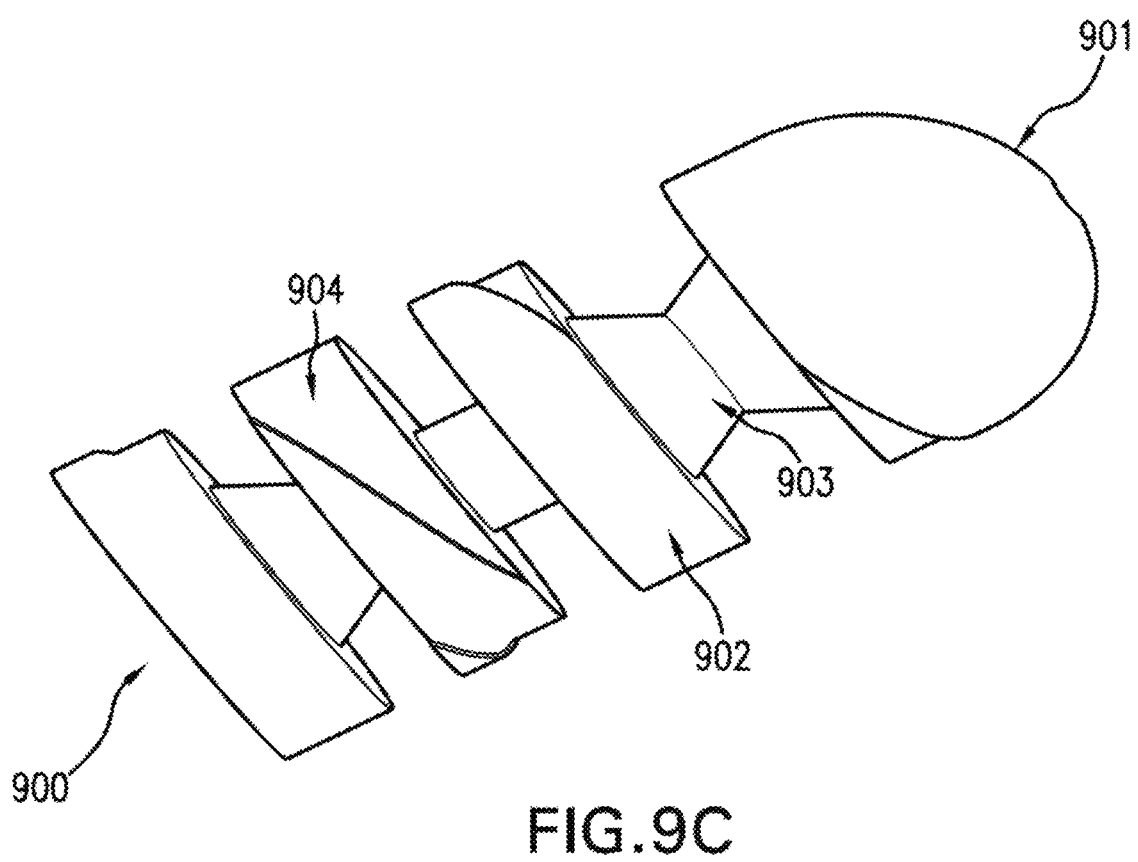

Referring now to FIG. 9A an embodiment of stent 900 has a tapered proximal end 901 to allow ease of passage inside a body lumen, an outer frame 902 with a larger diameter to provide stiffness, and a center core 903 with a smaller diameter to provide flexibility. The outer frame 902 and the center core 903 can be cylindrical or cut with various contours in the surface to change the flexibility or rigidity of the stent. In FIG. 9B, the stent 900 has an outer frame 902 that forms a coil around the core 903. The stent 900 may further include a center lumen 20. In FIG. 9C, the stent 900 has sinusoidal channel 904 formed on the surface of outer frame 902. The channel 904 may have variable depth. The center core 903 may have various shapes and sizes to adjust the flexibility, stability and rigidity of the stent 900.

In one embodiment, the stent 900 is inserted into the canal of a bone having a fracture. In another embodiment, the stent 900 is coated with a hydrogel. The hydrogel expands by absorbing of fluids and improves the connection and support of the inner wall of the bone canal. In another embodiment, the stent 900 is used to attach bone fractures together. In another embodiment, the stent 900 is placed through the bone cortex.

Figure 10:
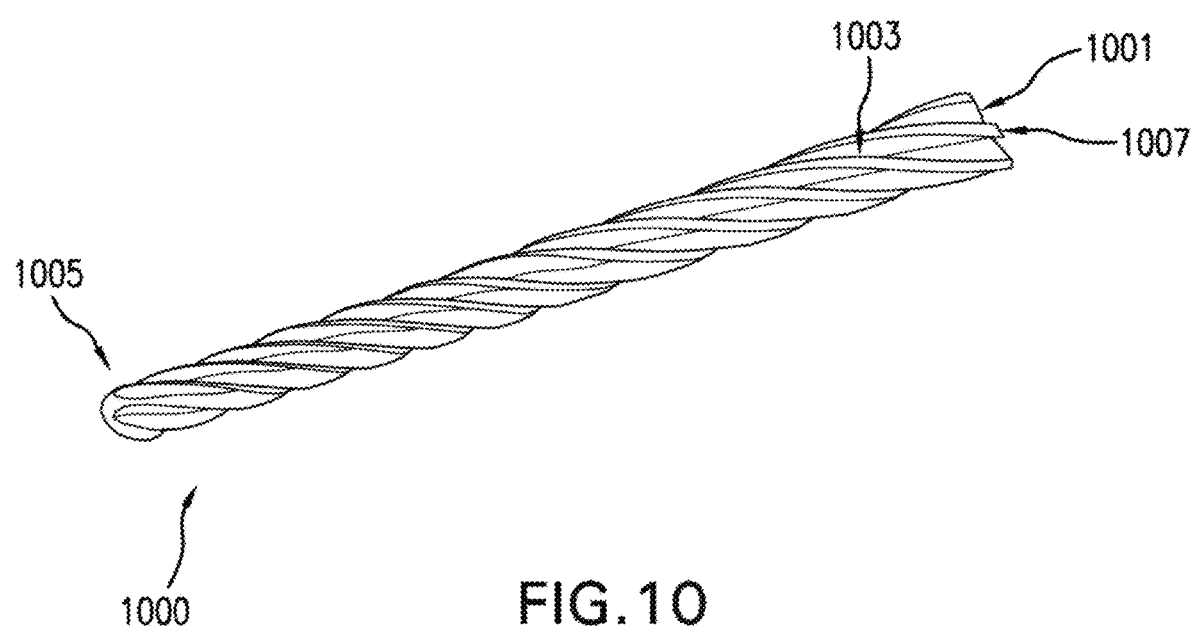
FIG. 10 shows another embodiment of a stent with sinusoidal channels of varying pitches.

Referring now to FIG. 10, another embodiment of a stent 1000 has channels of varying widths and depths on the exterior of the stent body. For example channel 1001 has a width that is greater than the width of channel 1003. The variable width and depth can be used to change the flow of fluids or friction to the lumen it is place in. Similar channels may also be formed on the interior side of a tubular stent. In the embodiment shown in FIG. 10, the stent 1000 has a tapered tip 1005 to facilitate advancement of the stent inside a body lumen. The wide distal flare 1007 prevents migration and increases stability of the stent 900. The stent 1000 may have channels of shorter or longer pitches to enable increases in fluid flow and stability. The stent 1000 may further include a center lumen for a guide wire or fluid flow.

Figure 11A:
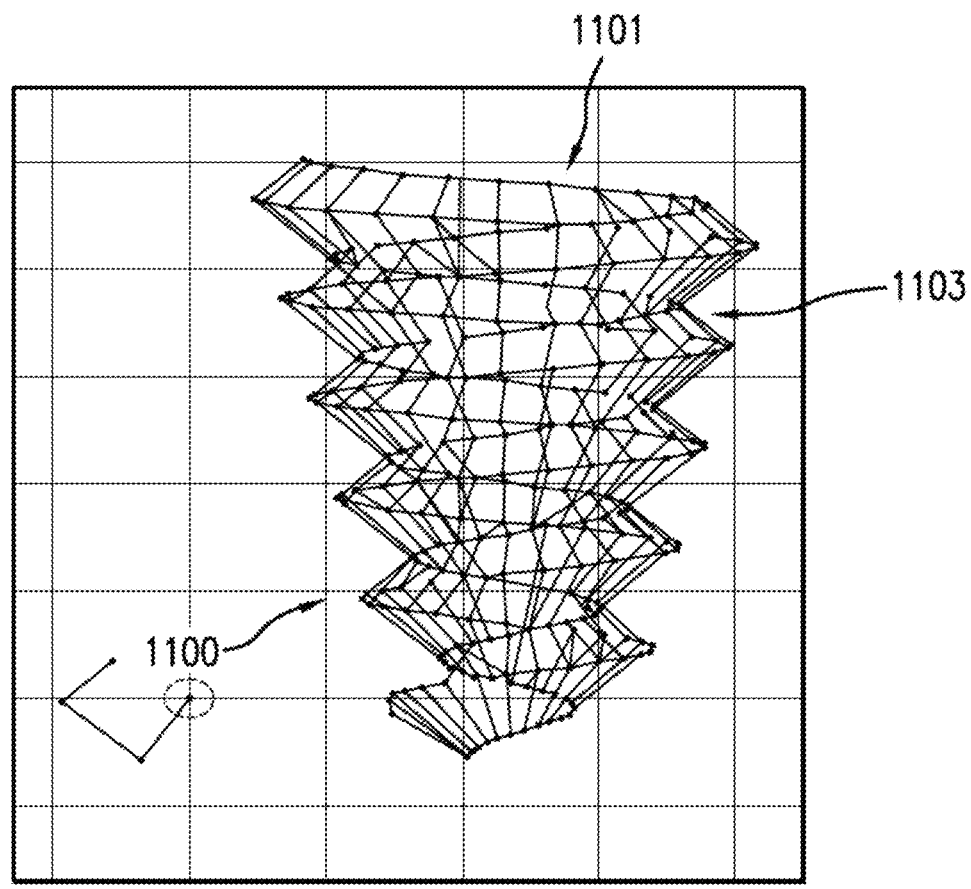
FIGS. 11A-11B shows another embodiment of a stent of the present application.
Figure 11B:
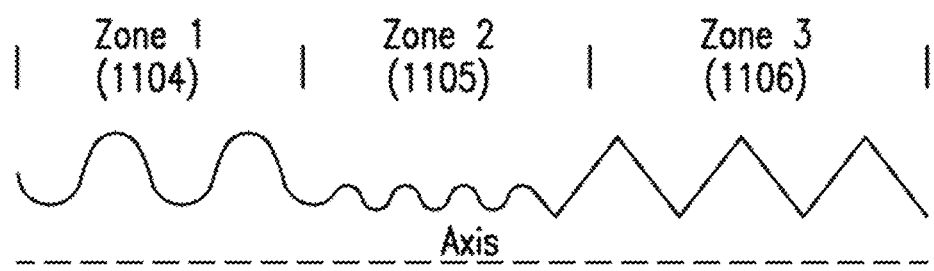

Referring now to FIGS. 11A-11B another embodiment of a stent 1100 has a larger proximal end 1101 with a helical surface channel 1103. The stent 1100 is in the shape of a cone or a cylinder with alternating variation in the diameter of the stent body. The surface channel 1103 may have regions 1104, 1105 and 1106 with different shapes and depth in each region, so as to change the flow rate, flow volume, and/or in each region.

Figure 12:
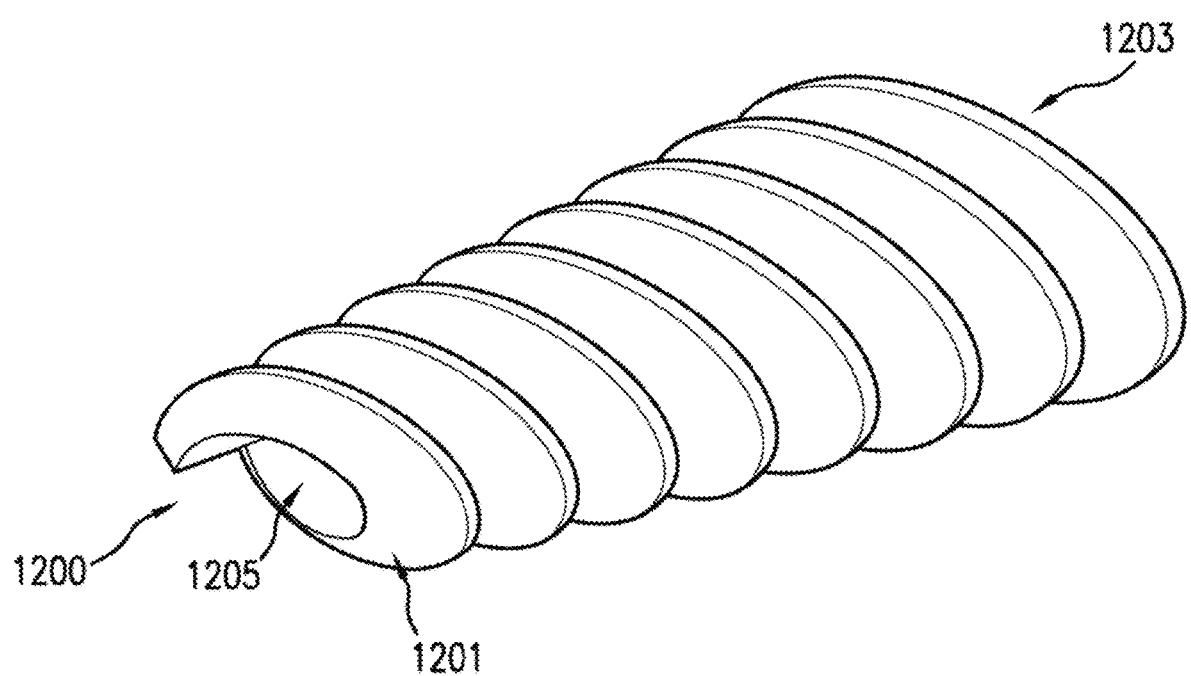
FIG. 12 shows another embodiment of a stent of the present application.

FIG. 12 shows another embodiment of a stent 1200. The pitch of the stent can change in various zones of the stent. The stent has a smaller diameter in the proximal end 1201 and larger diameter in the distal end 1203. The stent 1200 may have an opening 1205 that is big enough to adapt a wire. The stent 1200 may have a gradual increasing or decreasing pitch. In another embodiment, the pitch may change in different sections of the stent to better contour to the anatomy.

Other embodiments of stents of the present application are shown in FIGS. 15-18.

Figure 15:
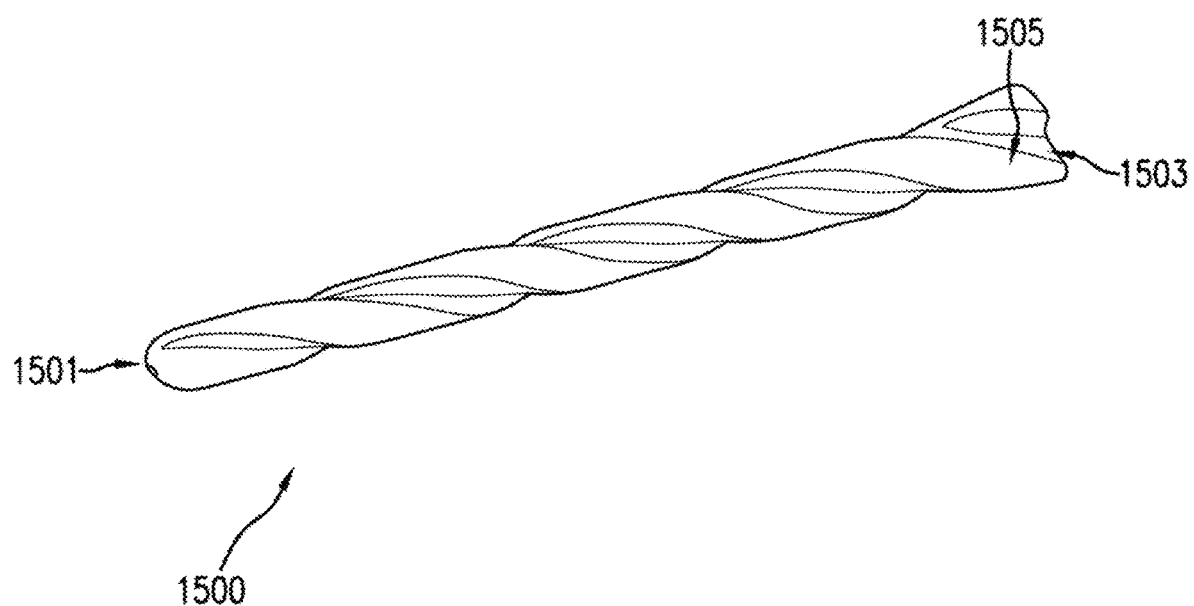
FIG. 15 shows another embodiment of a stent of the present application.

FIG. 15 shows an embodiment of a stent 1500 with a conical tip 1501 to allow for ease of access into the area it will be placed, a flared distal end 1503 for anchoring or prevention of migration into a lumen, out of a lumen, or within a lumen. The flares 1505 can be unidirectional or bi directional.

Figure 16:
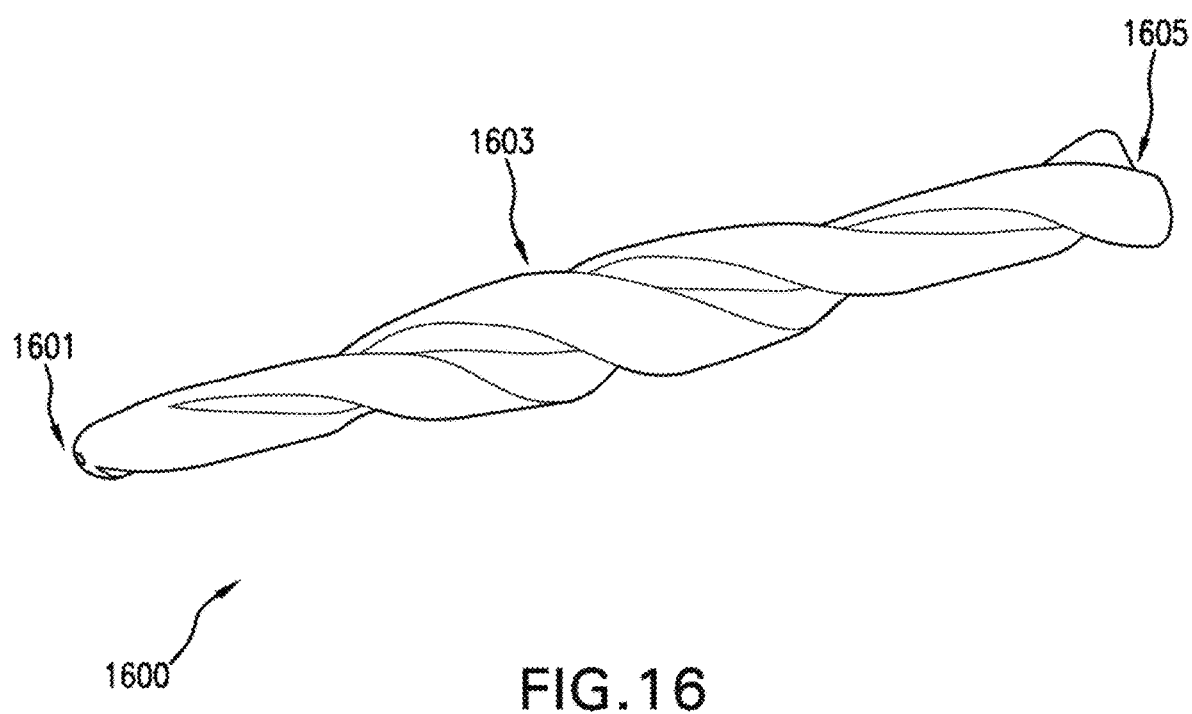
FIG. 16 shows another embodiment of a stent of the present application.

FIG. 16 shows an embodiment of a stent 1600 with a conical end 1601 and a swollen middle section 1603. The stent 1600 may be made from an elastomer. In one embodiment, the elastomer may expands more in a area in the middle, the end, or in multiple locations of the stent body to increase fluid flow by providing larger and deeper channels in the stent. In another embodiment, the end of the stent 1600 has an anti-migration mechanism that will expand to keep the stent in place. Anti-migration device at the distal end 1605 of the stent can be located anywhere along the length of the stent access.

Figure 17:
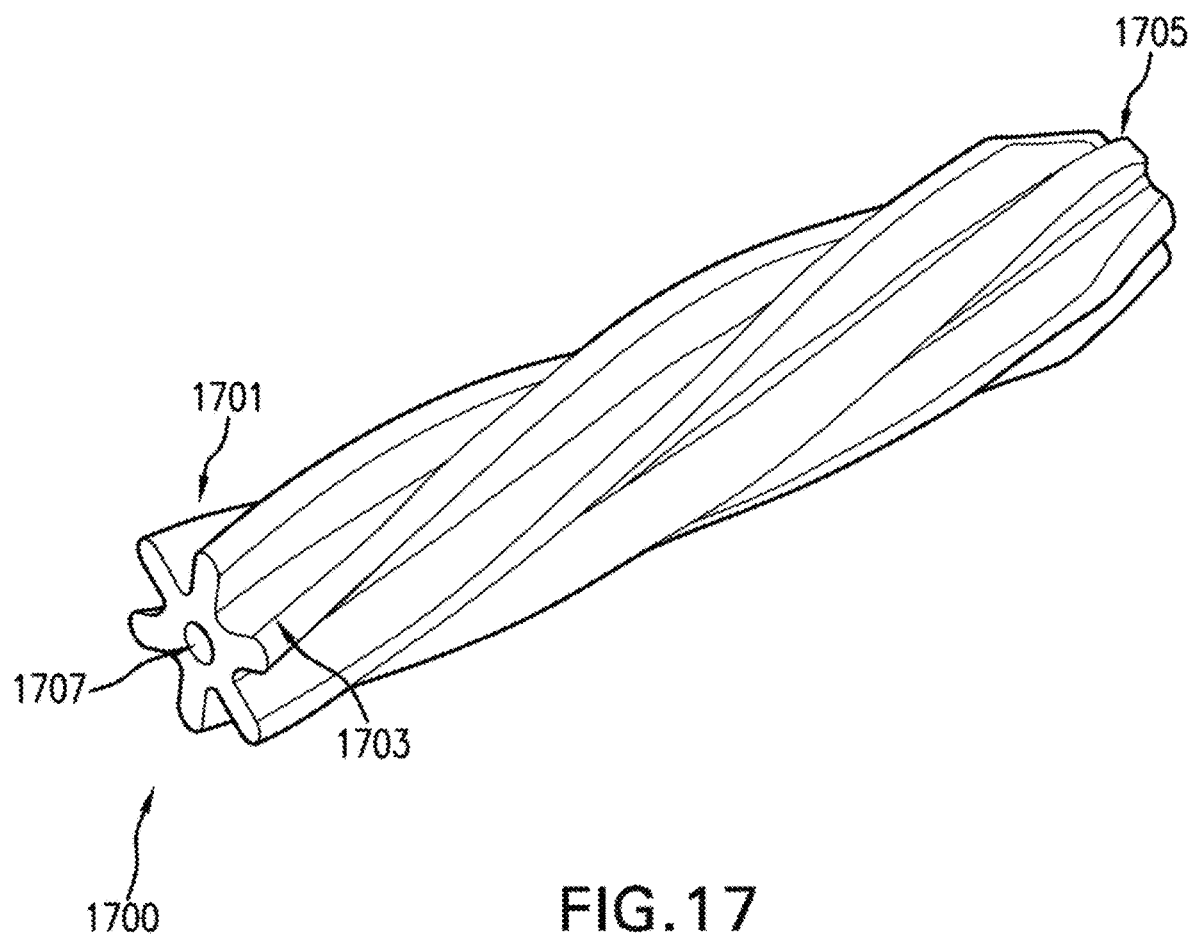
FIG. 17 shows another embodiment of a stent of the present application.

FIG. 17 shows another embodiment of a stent 1700 with leaflets 1701 to form channels 1703. In this embodiment, the stent 1700 has a tapered end 1705 to allow for ease of entry. The rotation of the sinusoidal channels 1703 may be changed to adjust fluid flow, collapse ability, etc. The leaflets attached to the cam 1707 can be folded over to allow the diameter of the stent 1700 to become smaller when being loaded into a deliver device or being place in a deliver tube like an endoscope. The channels walls can be straight, rounded, or a combination thereof depending on the cavity or lumen where the stent is placed.

Figure 18:
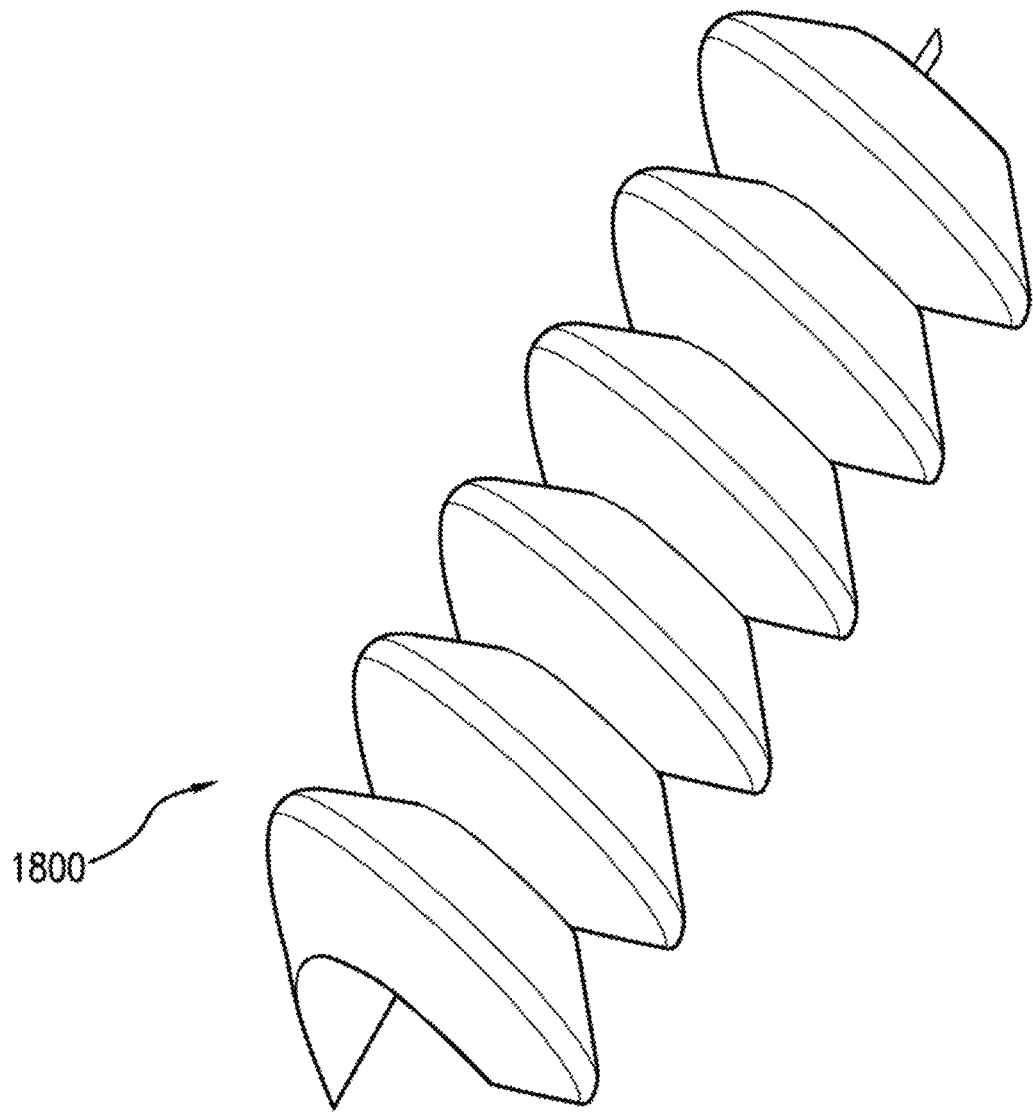
FIG. 18 shows another embodiment of a stent of the present application.

FIG. 18 shows another embodiment of a stent 1800. The stent 1800 is made in a way to allow the sinusoidal channel of the stent occur on the inside of the stent. The outside of the stent conforms to the anatomy the stent is placed in and flexibility is determined by the pitch of the sinusoidal channel. The inside of the stent forms the same sinusoidal as the outside of the stent. In one embodiment, the stent 1800 is made in such a way that it can be inserted in a screw in fashion.

A person or ordinary skill in the art would understand that other folding or interlocking may also be employed. The channel walls or leaflets can also be of varying thicknesses and lengths to provide the stent with desired rigidity, flexibility, pushability, trackability, luminal contact and/or absorption profile. For example, a stent made from bioabsorbable material may have leaflets that are thinner at the tip (where they touch the lumen wall) and thicker at the base (where they are attached to the cam), thus allowing for degradation from the tip to the base. In another embodiment, the cam itself can be cut in various ways to change its diameter at different points to change the pushability and flexibility of the device.

Figure 19A:
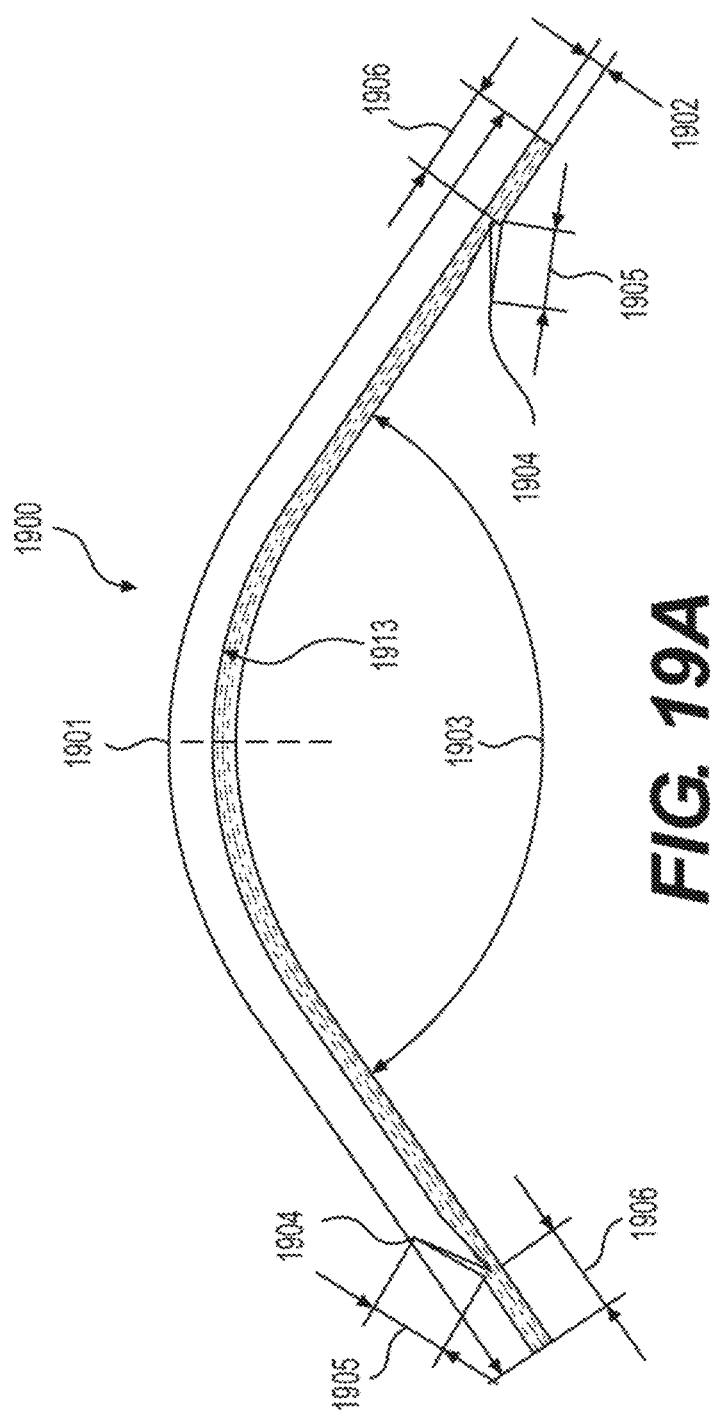
FIGS. 19A-E show another embodiment of a stent of the present application.

FIG. 19A shows the basic design of another embodiment of a stent 1900. In one embodiment, the stent 1900 is made from a polymeric material. In certain embodiments, the polymeric material may be Aquaprene 8020 with Opaciprene, Dioxaprene 100M with Opaciprene, or Lactoprene 7415 with Opaciprene. Appropriate grades of USD, PPD and MDP may also be selected for use in manufacturing the stent. In some embodiments, the stent comprises a fast-absorbing polymer, such as USD5 (Aquaprene 8020: 20% PEG, 80% p-dioxanone). In other embodiments, the stent comprises a medium-absorbing polymer, such as PPD3 (Dioxaprene 100M: Poly(para-diaxanone). In still other embodiments, the stent comprises a slow-absorbing polymer, such as MDP3 (Lactoprene 7415: 74/15/11 copolymer of lactide/trimethylene carbonate/caprolactone). In some embodiments, the lactide is the monomer L-lactide. In some embodiments, the stent is impregnated with a ~1% to ~40% $BaSO_4$ solution in a suitable carrier. In further embodiments, the stent is impregnated with a ~10% to ~30% $BaSO_4$ solution in a suitable carrier. In still further embodiments, the stent is impregnated with a ~12% to ~22% $BaSO_4$ solution in a suitable carrier. In particular embodiments, the stent is impregnated with a ~17% $BaSO_4$ solution in a suitable carrier.

The stent length 1901 is variable, dependent upon the application or location the stent 1900 is to be used in. In some embodiments, the stent length 1091 can be between about 5 mm and about 300 mm. In particular embodiments, the stent length 1091 is about 20, 40, 60, 80, 100, 150 or 225 mm. In some embodiments, the stent 1900 has an outer diameter 1902 of between about 1.8 mm and about 2.2 mm. In other embodiments, the stent 1900 has an outer diameter 1902 of between about 1.9 mm and about 2.1 mm. In particular embodiments, the stent 1900 has an outer diameter 1902 of about 2.0 mm. In some embodiments, the ends of the stent 1900 are tapered to be narrower than the main body of the stent 1900. The "outer diameter" refers to the linear distance between the two farthest points on the device along a straight line that passes through the center of the device in a cross-section.

In some embodiments, the biliary and pancreatic stents of the present application are made for materials that are visible fluoroscopically such that the stent can be monitored under fluoroscopy. In comparison to other stents, the biliary and pancreatic stents of the present application provides better simulated flow rates, better simulated migration resistance and better crush resistance.

The stent 1900 of this embodiment is flexible. In some embodiments, the stent flexes after placement in the target location. In some embodiments, the body of the stent can tolerate a bend 1903 of between about 90° and about 135° without experiencing a degradation of fluid flow rate. In other embodiments, the body of the stent can tolerate a bend 1903 of between about 100° and about 125° without experiencing a degradation of fluid flow rate. In still other embodiments, the body of the stent can tolerate a bend 1903 of about 112° without experiencing a degradation of fluid flow rate.

In some embodiments, the body of the stent 1900 is curved, having a curvature 1913 with a radius of between about 10 mm and about 70 mm. In other embodiments, the body of the stent 1900 has a curvature 1913 with a radius of between about 20 mm and about 60 mm. In still other embodiments, the body of the stent 1900 has a curvature 1913 with a radius of between about 30 mm and about 50 mm. In particular embodiments, the body of the stent 1900 has a curvature 1913 with a radius of about 40 mm.

The stent 1900 comprises two anti-migration devices 1904 that expand outwards from the elongated body of the stent 1900 so as to anchor the stent in position within a bodily lumen. In some embodiments, the anti-migration devices are elongated protrusions that extend from the stent and contact the tissue of the lumen in order to hold the stent in place. It some embodiments, the tip of the anti-migration devices is pointed, so that the tip can embed in the tissue. In some embodiments, the anti-migration devices are held flush with the surface of the stent prior to and during deployment and are allowed to fold out following placement at the target site. The anti-migration devices 1904 are placed in proximity to the ends of the stent, however, one of ordinary skill will understand that the placement of the anti-migration devices 1904 is not limiting on the application. In some embodiments, the anti-migration devices 1904 are between about 1 mm and about 12 mm in length 1905. In further embodiments, the anti-migration devices 1904 are between about 3 mm and about 10 mm in length 1905. In still further embodiments, the anti-migration devices 1904 are between about 5 mm and about 8 mm in length 1905. In a particular embodiment, the anti-migration devices 1904 are about 7 mm in length 1905. Furthermore, in some embodiments, the anti-migration devices 1904 are a distance 1906 of between about 1 mm and about 12 mm from each end of the stent 1900. In further embodiments, the anti-migration devices 1904 are a distance 1906 of between about 3 mm and about 10 mm from each end of the stent 1900. In still further embodiments, the anti-migration devices 1904 are a distance 1906 of between about 5 mm and about 8 mm from each end of the stent 1900. In a particular embodiment, the anti-migration devices 1904 are a distance 1906 of about 7 mm from each end of the stent 1900. In some embodiments, the anti-migration devices 1904 are the same distance 1906 from each end of the stent 1900. In other embodiments, the anti-migration devices 1904 are different distances 1906 from each end of the stent 1900. In some embodiments, the anti-migration devices 1904 are in the form of flaps or tails.

Figure 19B:
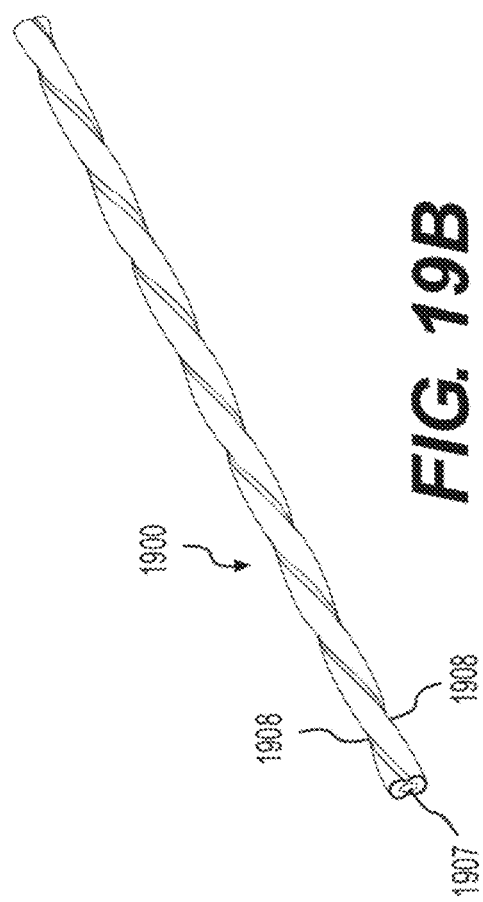

FIG. 19B is a 3-D rendering of the stent 1900. The end of this perspective view shows that the stent has a single central lumen 1907. The longitudinal central lumen 1907 of the stent 1900 is formed within the polymeric material and provides a channel for a guide wire. The narrowing of the stent on either side of the central lumen 1907 creates opposing external channels 1908 for fluid flow on the external surface of the stent 1900. As shown in FIG. 19B, the stent 1900 is twisted, causing the opposing external channels 1908 to spiral around the stent 1900.

Figure 19E:
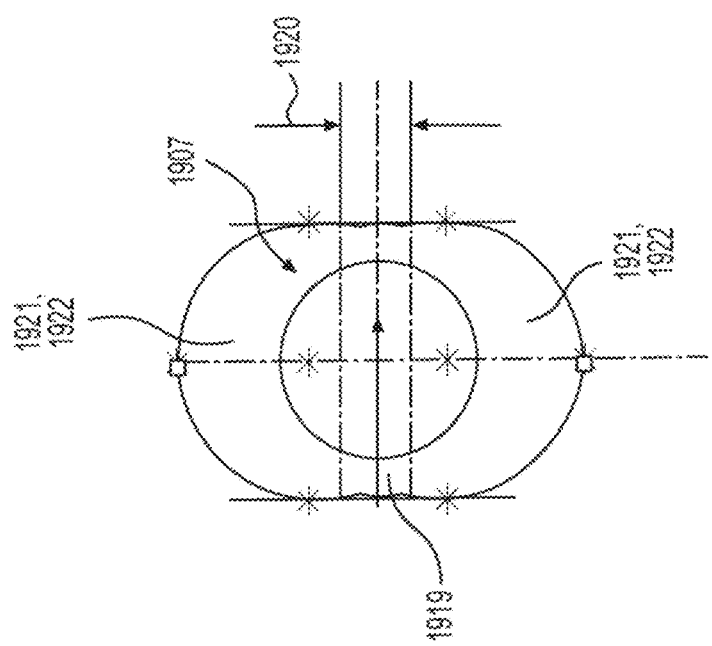
Figure 19C:
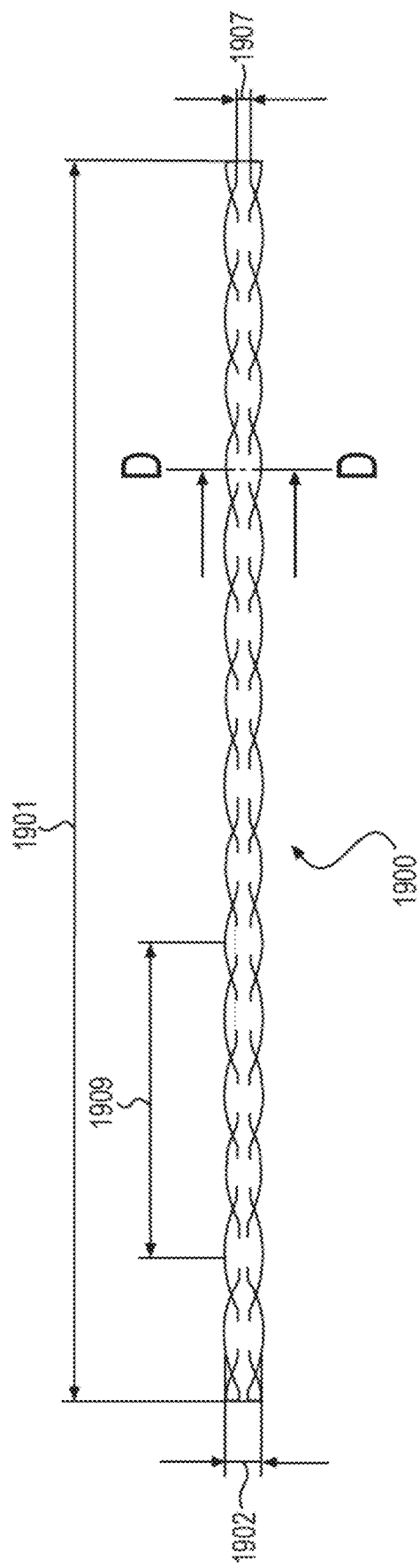

FIG. 19C is a side view of the stent 1900, showing the spiraling of the external channels around the central lumen 1907 (dashed lines). The present inventors have surprisingly found that the fluid flow through the external channels is optimized by controlling the number of twists of the stent per inch (i.e., number of turns per 25.4 mm, shown in FIG. 19C as 1909, wherein one twist is a 360 degree rotation around the central axis of the stent). In addition, the present inventors have found that increasing the number of twists per inch (TPI) increases/improves the flexibility of the stent, as measured by deflection of the stent material with an equivalent amount of force applied. Increasing the TPI (for example, from 1 TPI to 2 TPI or from 2 TPI to 3 TPI) increases the amount of deflection, thereby indicating that higher TPI produces a more flexible stent. In some embodiments, the number of twists is at least, or more than, 1 twist per inch. In other embodiments, the number of twists is at least, or more than, 1.5 twists per inch. In still other embodiments, the number of twists is at least, or more than, 1.75 twists per inch. In yet other embodiments, the number of twists is between about 1.5 and 2.5 twists per inch. In even other embodiments, the number of twists is between about 1.75 and 2.25 twists per inch. In still other embodiments, the number of twists is about 2 twists per inch. In particular embodiments, the number of twists is at least, or more than, 2 twists per inch. In further embodiments, the number of twists equals 2 twists per inch. In other further embodiments, the number of twists is more than 2 twists per inch. The twisting of the stent may be carried out by any means known to one of ordinary skill in the art. In some embodiments, the stent may be formed in a straight, non-twisted, configuration, followed by twisting or machining to the desired number of twists/inch. In other embodiments, the stent 1900 may be formed or molded in the twisted shape. The polymer material from which the stent 1900 is made may be fixed in place in the twisted position by any means known to one of ordinary skill in the art, e.g., a heating process, etc.

Figure 19D:
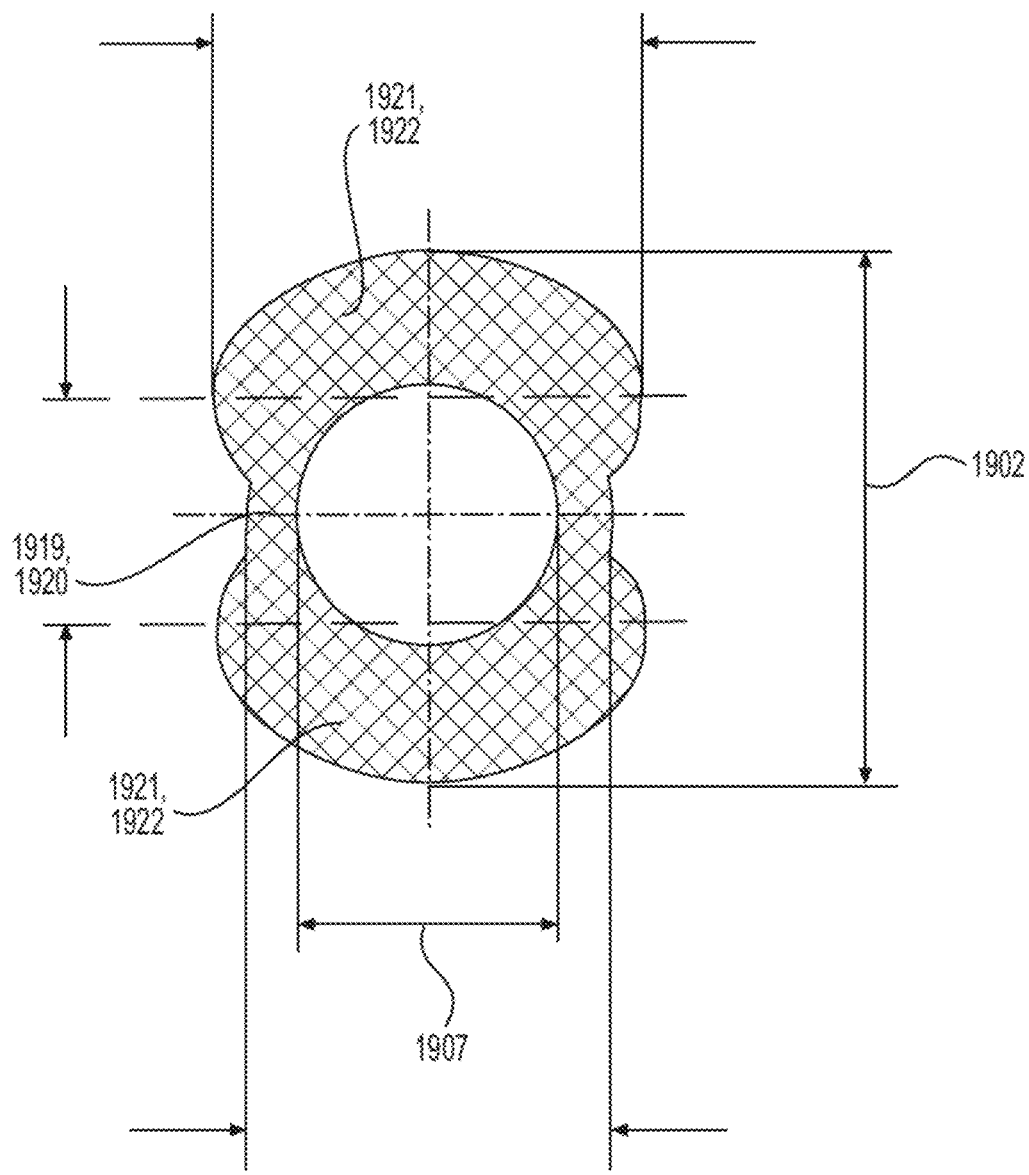

FIG. 19D shows a cross-section view of the stent 1900 at line D-D of FIG. 19C and looking towards one end of the stent 1900. In terms of orientation for describing the cross-section, the directions up, down, upper and lower refer direction lying on the main axis that bisects the cross-section of the stent into the longest mirror-image halves. Sides and side-to-side refer to a cross axis that is perpendicular to the main axis. In some embodiments, the central channel 1907 is between about 0.8 mm and about 1.2 mm in diameter. In other embodiments, the central channel 1907 is between about 0.9 mm and about 1.1 mm in diameter. In still other embodiments, the central channel 1907 is between about 0.95 mm and about 1.05 mm in diameter. In particular embodiments, the central channel 1907 is about 1 mm in diameter. In other particular embodiments, the central channel 1907 is 1 mm+/−0.1 mm in diameter. The "diameter" of the central channel refers to the linear distance between the two farthest points within the lumen of the central channel along a straight line that passes through the center of the central channel in a cross-section.

Still referring to FIG. 19D, the cross-section of the stent comprises a central circle 1919 that surrounds the central channel 1907 and upper and lower bolsters 1921 that overlap the central circle 1919 and, in some embodiments, each other. The sides of the central circle 1919, between the points where the bolsters 1921 intersect with the central circle 1919, form the minor, thinner, walls 1920 of the stent around the central channel 1907. In some embodiments, the thickness of the minor walls 1920 is between about 0.1 mm and about 0.3 mm. In other embodiments, the thickness of the minor walls 1920 is between about 0.15 mm and about 0.25 mm. In particular embodiments, the thickness of the minor walls 1920 is about 0.2 mm+/−0.02 mm. In more particular embodiments, the thickness of the minor walls 1920 is about 0.2 mm+/−0.01 mm.

Still referring to FIG. 19D, the upper and lower bolsters 1921 are generally elliptical, oval or circular in shape. In the case of an oval or elliptical bolster 1921, the longest longitudinal axis of the bolster 1921 may lie oriented perpendicular to the main axis of the cross section of the stent, as shown in FIG. 19D. In some embodiments, the longest longitudinal axis of an oval or elliptical bolster 1921 may lie oriented along the main axis of the cross section of the stent. The bolsters 1921 form the major, thicker, walls of the stent.

In some embodiments, the thickness of the major walls 1922 is between about 0.3 mm and about 0.7 mm at the main axis. In other embodiments, the thickness of the major walls 1922 is between about 0.4 mm and about 0.6 mm at the main axis. In particular embodiments, the thickness of the major walls 1922 is about 0.5 mm+/−0.05 mm at the main axis. In more particular embodiments, the thickness of the major walls 1922 is about 0.5 mm+/−0.025 mm at the main axis.

In some embodiments, the bolsters 1921 have a side-to-side thickness of between about 1.4 mm and about 1.8 mm. In other embodiments, the bolsters 1921 have a side-to-side thickness of between about 1.5 mm and about 1.78 mm. In particular embodiments, the bolsters 1921 have a side-to-side thickness of about 1.61 mm+/−0.16 mm. In more particular embodiments, the bolsters 1921 have a side-to-side thickness of about 1.61 mm+/−0.08 mm.

FIG. 19E shows a cross-sectional view of an alternative embodiment of the stent 1900 at line D-D of FIG. 19C and looking towards one end of the stent 1900 where the bolsters 1921 are of a circular shape. The sides of the central circle 1919, between the points where the bolsters 1921 intersect with the central circle 1919, form the minor, thinner, walls 1920 of the stent around the central channel 1907. In some embodiments, the thickness of the minor walls 1920 is between about 0.1 mm and about 0.3 mm. In other embodiments, the thickness of the minor walls 1920 is between about 0.15 mm and about 0.25 mm. In particular embodiments, the thickness of the minor walls 1920 is about 0.2 mm+/−0.02 mm. In more particular embodiments, the thickness of the minor walls 1920 is about 0.2 mm+/−0.01 mm. In some embodiments, the diameter of the circular bolsters 1921 is the same as the diameter of the central circle 1919. In other embodiments, the diameter of the circular bolsters 1921 is greater than the diameter of the central circle 1919. In some embodiments, the thickness of the major walls 1922 is between about 0.3 mm and about 0.7 mm at the main axis. In other embodiments, the thickness of the major walls 1922 is between about 0.4 mm and about 0.6 mm at the main axis. In particular embodiments, the thickness of the major walls 1922 is about 0.5 mm+/−0.05 mm at the main axis. In more particular embodiments, the thickness of the major walls 1922 is about 0.5 mm+/−0.025 mm at the main axis.

Figure 20A:
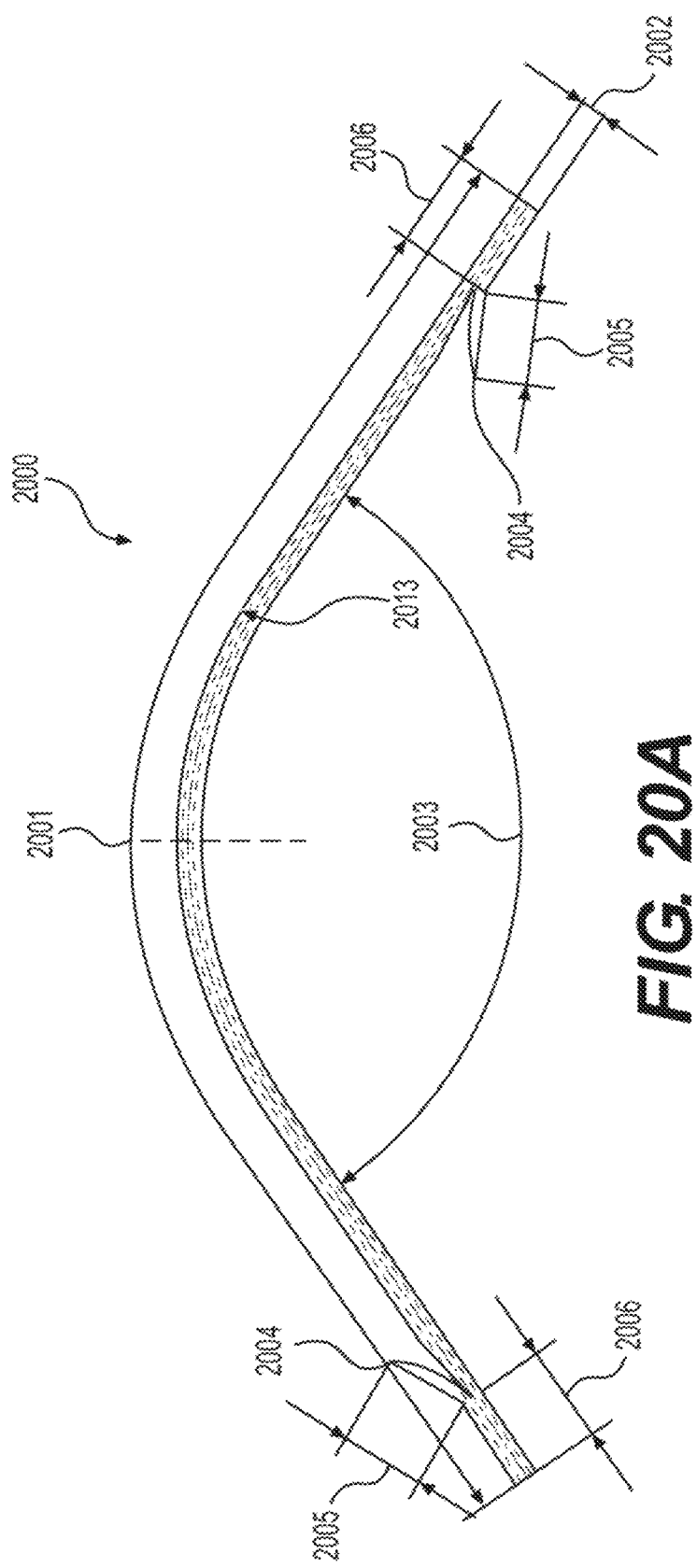

FIG. 20A shows the basic design of another embodiment of a stent 2000. In one embodiment, the stent 2000 is made from a polymeric material. In certain embodiments, the polymeric material may be Aquaprene 8020 with Opaciprene, Dioxaprene 100M with Opaciprene or Lactoprene 7415 with Opaciprene. Appropriate grades of USD, PPD and MDP may also be selected for use in manufacturing the stent. In some embodiments, the stent comprises a fast-absorbing polymer, such as USD5 (Aquaprene 8020: 20% PEG, 80% p-dioxanone). In other embodiments, the stent comprises a medium-absorbing polymer, such as PPD3 (Dioxaprene 100M: Poly(para-diaxanone). In still other embodiments, the stent comprises a slow-absorbing polymer, such as MDP3 (Lactoprene 7415: 74/15/11 copolymer of lactide/trimethylene carbonate/caprolactone). In some embodiments, the stent is impregnated with a ~1% to ~40% $BaSO_4$ solution in a suitable carrier. In further embodiments, the stent is impregnated with a ~10% to ~30% $BaSO_4$ solution in a suitable carrier. In still further embodiments, the stent is impregnated with a ~12% to ~22% $BaSO_4$ solution in a suitable carrier. In particular embodiments, the stent is impregnated with a ~17% $BaSO_4$ solution in a suitable carrier.

The stent length 2001 is variable, dependent upon the application or location the stent 2000 is to be used in. In some embodiments, the stent length 2001 can be between about 20 mm and about 300 mm. In particular embodiments, the stent length 2001 is about 40, 60, 80, 100, 120, 150, 225 or 250 mm. In some embodiments, the stent 2000 has an outer diameter 2002 of between about 2.0 mm and about 3.2 mm. In other embodiments, the stent 2000 has an outer diameter 2002 of between about 2.34 mm and about 2.86 mm. In still other embodiments, the stent 2000 has an outer diameter 2002 of between about 2.5 mm and about 2.7 mm. In particular embodiments, the stent 2000 has an outer diameter 2002 of about 2.6 mm+/−0.26 mm. In more particular embodiments, the stent 2000 has an outer diameter 2002 of about 2.6 mm+/−0.13 mm. In some embodiments, the ends of the stent 2000 are tapered to be narrower than the main body of the stent 2000. The "outer diameter" refers to the linear distance between the two farthest points on the device along a straight line that passes through the center of the device in a cross-section.

The stent 2000 of this embodiment is flexible. In some embodiments, the stent flexes after placement in the target location. In some embodiments, the body of the stent can tolerate a bend 2003 of between about 90° and about 135° without experiencing a degradation of fluid flow rate. In other embodiments, the body of the stent can tolerate a bend 2003 of between about 100° and about 125° without experiencing a degradation of fluid flow rate. In still other embodiments, the body of the stent can tolerate a bend 2003 of about 112° without experiencing a degradation of fluid flow rate.

In some embodiments, the body of the stent 2000 is curved, having a curvature 2013 with a radius of between about 10 mm and about 70 mm. In other embodiments, the body of the stent 2000 has a curvature 2013 with a radius of between about 20 mm and about 60 mm. In still other embodiments, the body of the stent 2000 has a curvature 2013 with a radius of between about 30 mm and about 50 mm. In particular embodiments, the body of the stent 2000 has a curvature 2013 with a radius of about 40 mm.

The stent 2000 comprises two anti-migration devices 2004 that expand outwards from the elongated body of the stent 2000 so as to anchor the stent in position within a bodily lumen. In some embodiments, the anti-migration devices are elongated protrusions that extend from the stent and contact the tissue of the lumen in order to hold the stent in place. It some embodiments, the tip of the anti-migration devices is pointed, so that the tip can embed in the tissue. In some embodiments, the anti-migration devices are held flush with the surface of the stent prior to and during deployment and are allowed to fold out following placement at the target site. The anti-migration devices 2004 are placed in proximity to the ends of the stent, however, one of ordinary skill will understand that the placement of the anti-migration devices 2004 is not limiting on the application. In some embodiments, the anti-migration devices 2004 are between about 1 mm and about 12 mm in length 2005. In further embodiments, the anti-migration devices 2004 are between about 3 mm and about 10 mm in length 2005. In still further embodiments, the anti-migration devices 2004 are between about 5 mm and about 8 mm in length 2005. In a particular embodiment, the anti-migration devices 2004 are about 7 mm in length 2005. Furthermore, in some embodiments, the anti-migration devices 2004 are a distance 2006 of between about 1 mm and about 12 mm from each end of the stent 2000. In further embodiments, the anti-migration devices 2004 are a distance 2006 of between about 3 mm and about 10 mm from each end of the stent 2000. In still further embodiments, the anti-migration devices 2004 are a distance 2006 of between about 5 mm and about 8 mm from each end of the stent 2000. In a particular embodiment, the anti-migration devices 2004 are a distance 2006 of about 7 mm from each end of the stent 2000. In some embodiments, the anti-migration devices 2004 are the same distance 2006 from each end of the stent 2000. In other embodiments, the anti-migration devices 2004 are different distances 2006 from each end of the stent 2000.

Figure 20B:
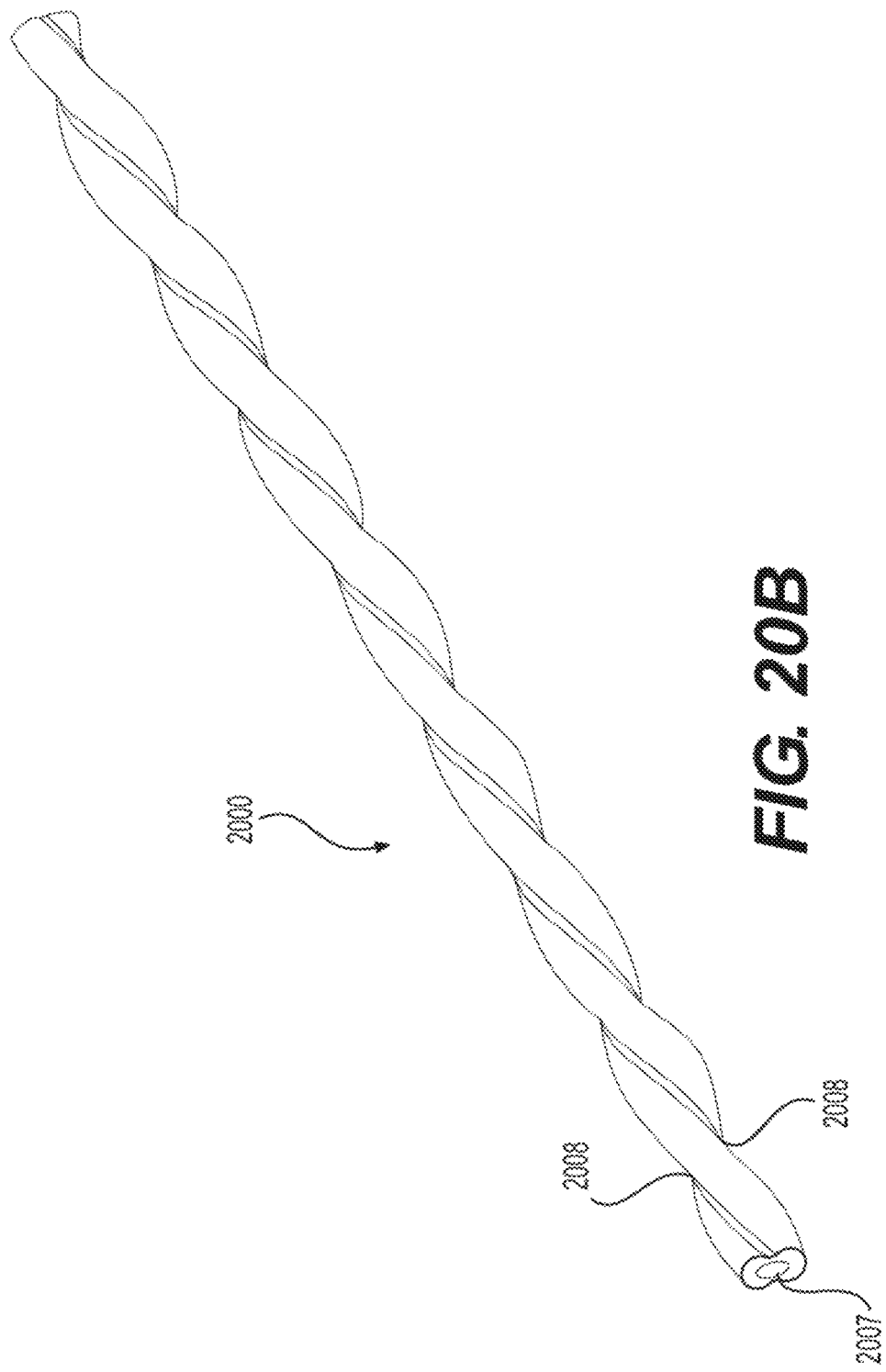
Figure 20C:
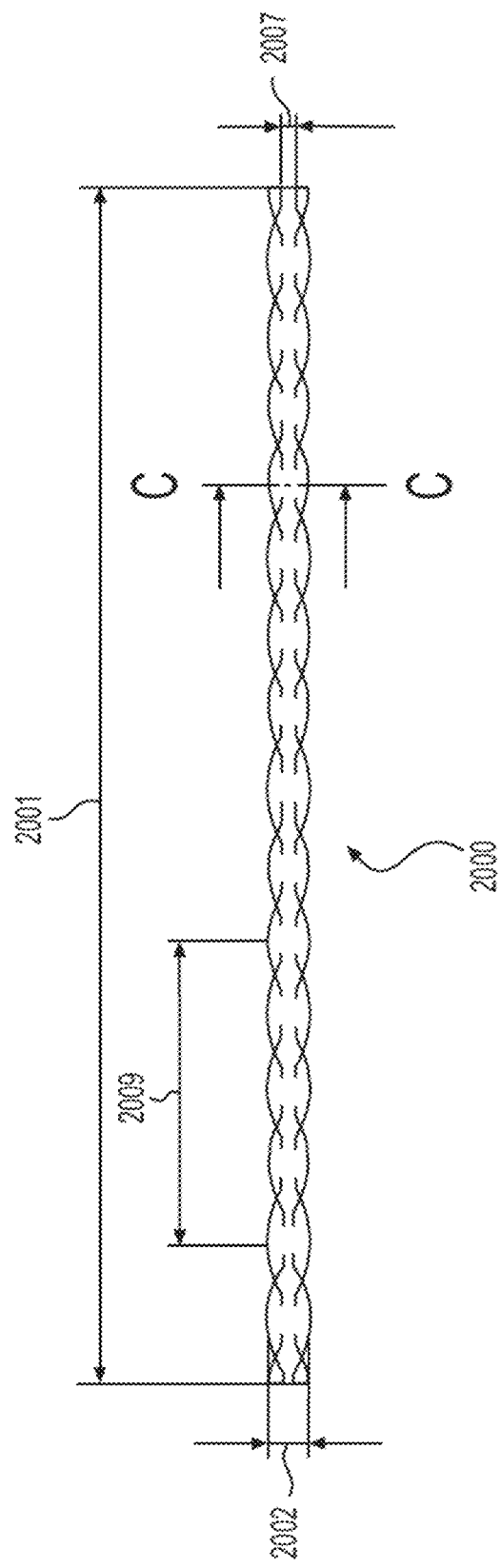

FIG. 20B is a 3-D rendering of the stent 2000. The end of this perspective view shows that the stent has a single central lumen 2007. The longitudinal central lumen 2007 of the stent 2000 is formed within the polymeric material and provides a channel for a guide wire. The narrowing of the stent on either side of the central lumen 2007 creates opposing external channels 2008 for fluid flow on the external surface of the stent 2000. As shown in FIG. 20B, the stent 2000 is twisted, causing the opposing external channels 2008 to spiral around the stent 2000. FIG. 20C is a side view of the stent 2000, showing the spiraling of the external channels around the central lumen 2007 (dashed lines). The inventors have surprisingly found that the fluid flow through the external channels is optimized by controlling the number of twists of the stent per inch (i.e., number of turns per 25.4 mm, shown in FIG. 20C as 2009, wherein one twist is a 360 degree rotation around the central axis of the stent). In addition, the present inventors have found that increasing the number of twists per inch (TPI) increases/improves the flexibility of the stent, as measured by deflection of the stent material with an equivalent amount of force applied. Increasing the TPI (for example, from 1 TPI to 2 TPI or from 2 TPI to 3 TPI) increases the amount of deflection, thereby indicating that higher TPI produces a more flexible stent. In some embodiments, the number of twists is at least, or more than, 1 twist per inch. In other embodiments, the number of twists is at least, or more than, 1.5 twists per inch. In still other embodiments, the number of twists is at least, or more than, 1.75 twists per inch. In yet other embodiments, the number of twists is between about 1.5 and 2.5 twists per inch. In even other embodiments, the number of twists is between about 1.75 and 2.25 twists per inch. In still other embodiments, the number of twists is about 2 twists per inch. In particular embodiments, the number of twists is at least, or more than, 2 twists per inch. In further embodiments, the number of twists equals 2 twists per inch. In other further embodiments, the number of twists is more than 2 twists per inch. The twisting of the stent may be carried out by any means known to one of ordinary skill in the art. In some embodiments, the stent may be formed in a straight, non-twisted, configuration, followed by twisting or machining to the desired number of twists/inch. In other embodiments, the stent 2000 may be formed or molded in the twisted shape. The polymer material from which the stent 2000 is made may be fixed in place in the twisted position by any means known to one of ordinary skill in the art, e.g., a heating process, etc.

FIG. 20D shows a cross-section view of the stent 2000 at line C-C of FIG. 20C and looking towards one end of the stent 2000. In some embodiments, the central channel 2007 is between about 0.8 mm and about 1.2 mm in diameter. In other embodiments, the central channel 2007 is between about 0.9 mm and about 1.1 mm in diameter. In still other embodiments, the central channel 2007 is between about 0.95 mm and about 1.05 mm in diameter. In particular embodiments, the central channel 2007 is about 1 mm+/−0.1 mm in diameter. The "diameter" of the central channel refers to the linear distance between the two farthest points within the lumen of the central channel along a straight line that passes through the center of the central channel in a cross-section.

Still referring to FIG. 20D, the cross-section of the stent comprises a central circle 2019 that surrounds the central channel 2007 and upper and lower bolsters 2021 that overlap the central circle 2019 and, in some embodiments, each other. The sides of the central circle 2019, between the points where the bolsters 2021 intersect with the central circle 2019, form the minor, thinner, walls 2020 of the stent around the central channel 2007. In some embodiments, the thickness of the minor walls 2020 is between about 0.1 mm and about 0.3 mm. In other embodiments, the thickness of the minor walls 2020 is between about 0.15 mm and about 0.25 mm. In particular embodiments, the thickness of the minor walls 2020 is about 0.2 mm+/−0.02 mm. In more particular embodiments, the thickness of the minor walls 2020 is about 0.2 mm+/−0.01 mm.

Still referring to FIG. 20D, the upper and lower bolsters 2021 are generally elliptical, oval or circular in shape. In the case of an oval or elliptical bolster 2021, the longest longitudinal axis of the bolster 2021 may lie oriented along the main axis of the cross section of the stent, as shown in FIG. 20D. In some embodiments, the longest longitudinal axis of an oval or elliptical bolster 2021 may lie oriented perpendicular to the main axis of the cross section of the stent. The bolsters 2021 form the major, thicker, walls of the stent.

In some embodiments, the thickness of the major walls 2022 is between about 0.6 mm and about 1.0 mm at the main axis. In other embodiments, the thickness of the major walls 2022 is between about 0.7 mm and about 0.9 mm at the main axis. In particular embodiments, the thickness of the major walls 2022 is about 0.8 mm+/−0.08 mm at the main axis. In more particular embodiments, the thickness of the major walls 2022 is about 0.8 mm+/−0.04 mm at the main axis.

In some embodiments, the bolsters 2021 have a side-to-side thickness of about 1.4 mm+/−0.14 mm. In more particular embodiments, the bolsters 2021 have a side-to-side thickness of about 1.4 mm+/−0.07 mm.

Figure 21A:
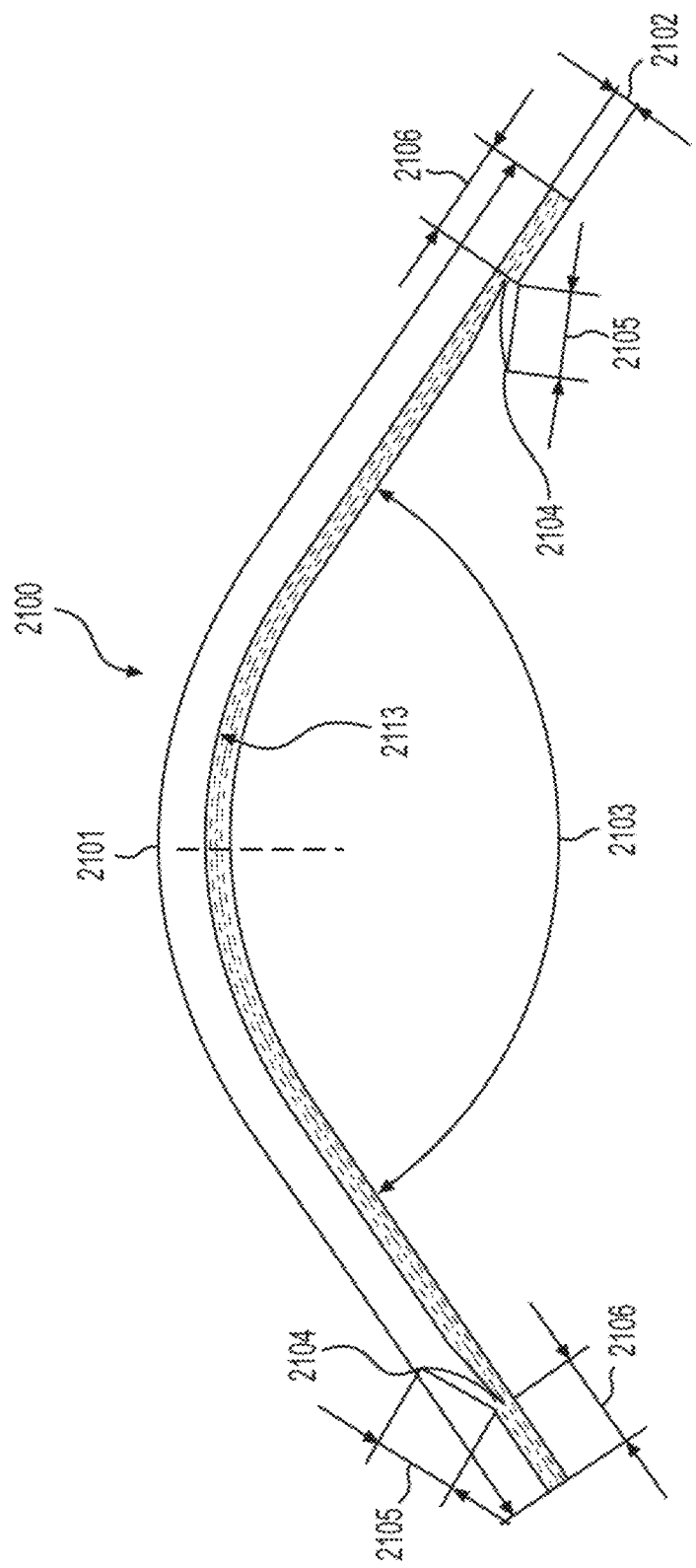

FIG. 21A shows the basic design of another embodiment of a stent 2100. In one embodiment, the stent 2100 is made from a polymeric material. In certain embodiments, the polymeric material may be Aquaprene 8020 with Opaciprene, Dioxaprene 100M with Opaciprene, or Lactoprene 7415 with Opaciprene. Appropriate grades of USD, PPD and MDP may also be selected for use in manufacturing the stent. In some embodiments, the stent comprises a fast-absorbing polymer, such as USD5 (Aquaprene 8020: 20% PEG, 80% p-dioxanone). In other embodiments, the stent comprises a slow-absorbing polymer, such as PPD3 (Dioxaprene 100M: Poly(para-diaxanone). In still other embodiments, the stent comprises a slow-absorbing polymer, such as MDP3 (Lactoprene 7415: 74/15/11 copolymer of lactide/trimethylene carbonate/caprolactone). In some embodiments, the stent is impregnated with a ~1% to ~40% $BaSO_4$ solution in a suitable carrier. In further embodiments, the stent is impregnated with a ~10% to ~30% $BaSO_4$ solution in a suitable carrier. In still further embodiments, the stent is impregnated with a ~12% to ~22% $BaSO_4$ solution in a suitable carrier. In particular embodiments, the stent is impregnated with a ~17% $BaSO_4$ solution in a suitable carrier.

The stent length 2101 is variable, dependent upon the application or location the stent 2100 is to be used in. In some embodiments, the stent length 2101 can be between about 20 mm and about 300 mm. In particular embodiments, the stent length 2101 is about 40, 60, 80, 100, 120, 150, 200 or 225 mm. In some embodiments, the stent 2100 has an outer diameter 2102 of between about 2.5 mm and about 5 mm. In other embodiments, the stent 2100 has an outer diameter 2102 of between about 3.06 mm and about 3.74 mm. In still other embodiments, the stent 2100 has an outer diameter 2102 of between about 3.3 mm and about 3.5 mm. In particular embodiments, the stent 2100 has an outer diameter 2102 of about 3.4+/−0.34 mm. In more particular embodiments, the stent 2100 has an outer diameter 2102 of about 3.4+/−0.17 mm. In some embodiments, the ends of the stent 2100 are tapered to be narrower than the main body of the stent 2100. The "outer diameter" refers to the linear distance between the two farthest points on the device along a straight line that passes through the center of the device in a cross-section.

The stent 2100 of this embodiment is flexible. Upon final placement of the stent 2100, in some embodiments, the body of the stent can tolerate a bend 2103 of between about 90° and about 135° without experiencing a degradation of fluid flow rate. In other embodiments, the body of the stent can tolerate a bend 2103 of between about 100° and about 125° without experiencing a degradation of fluid flow rate. In still other embodiments, the body of the stent can tolerate a bend 2103 of about 112° without experiencing a degradation of fluid flow rate.

In some embodiments, the body of the stent 2100 is curved, having a curvature 2113 with a radius of between about 10 mm and about 70 mm. In other embodiments, the body of the stent 2100 has a curvature 2013 with a radius of between about 20 mm and about 60 mm. In still other embodiments, the body of the stent 2100 has a curvature 2113 with a radius of between about 30 mm and about 50 mm. In particular embodiments, the body of the stent 2100 has a curvature 2113 with a radius of about 40 mm.

The stent 2100 comprises two anti-migration devices 2104 that expand outwards from the elongated body of the stent 2100 so as to anchor the stent in position within a bodily lumen. The anti-migration devices 2104 are placed in proximity to the ends of the stent, however, one of ordinary skill will understand that the placement of the anti-migration devices 2104 is not limiting on the application. In some embodiments, the anti-migration devices 2104 are between about 1 mm and about 12 mm in length 2105. In further embodiments, the anti-migration devices 2104 are between about 3 mm and about 10 mm in length 2105. In still further embodiments, the anti-migration devices 2104 are between about 5 mm and about 8 mm in length 2105. In a particular embodiment, the anti-migration devices 2104 are about 7 mm in length 2105. Furthermore, in some embodiments, the anti-migration devices 2104 are a distance 2106 of between about 1 mm and about 12 mm from each end of the stent 2100. In further embodiments, the anti-migration devices 2104 are a distance 2106 of between about 3 mm and about 10 mm from each end of the stent 2100. In still further embodiments, the anti-migration devices 2104 are a distance 2106 of between about 5 mm and about 8 mm from each end of the stent 2100. In a particular embodiment, the anti-migration devices 2104 are a distance 2106 of about 7 mm from each end of the stent 2100. In some embodiments, the anti-migration devices 2104 are the same distance 2106 from each end of the stent 2100. In other embodiments, the anti-migration devices 2104 are different distances 2106 from each end of the stent 2100.

Figure 21B:
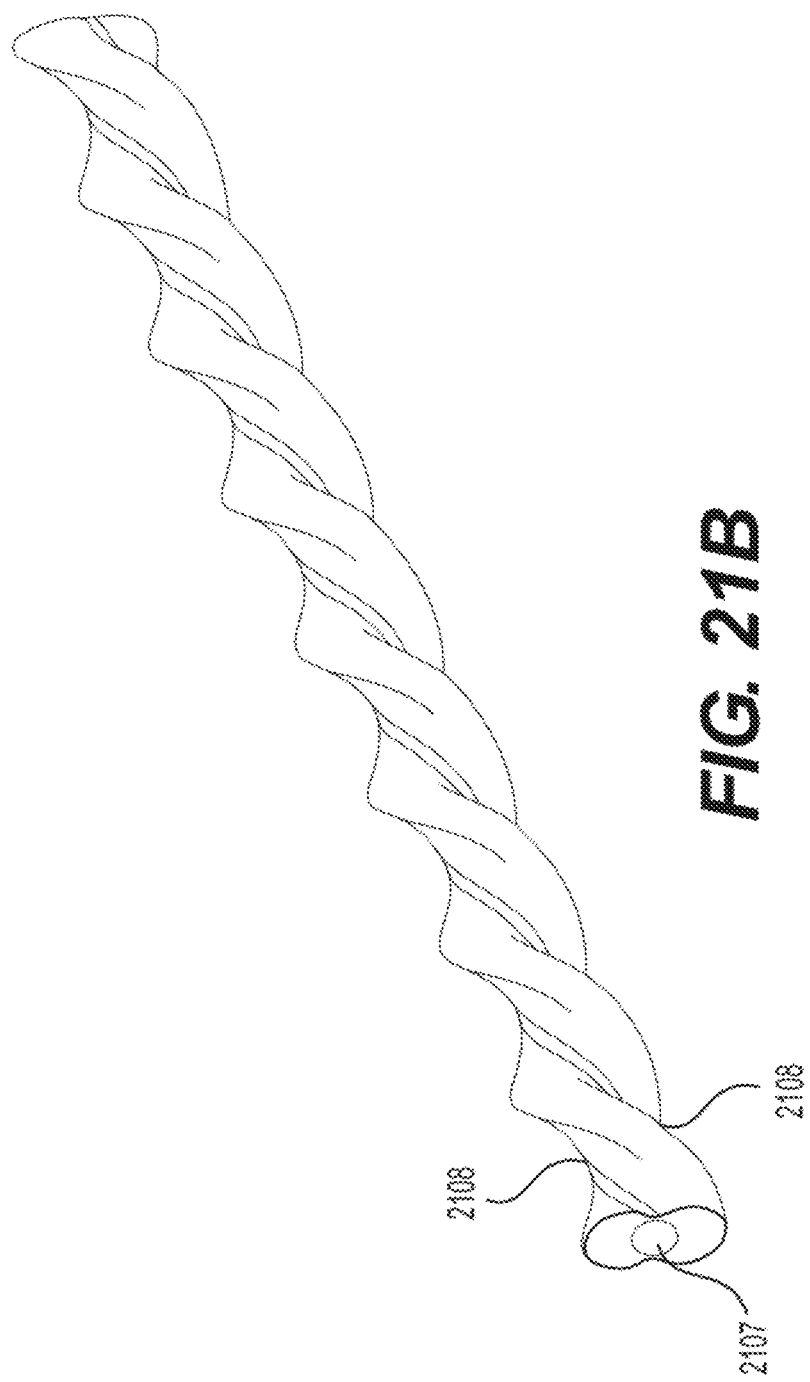

FIG. 21B is a 3-D rendering of the stent 2100. The end of this perspective view shows that the stent has a single central lumen 2107. The longitudinal central lumen 2107 of the stent 2100 is formed within the polymeric material and provides a channel for a guide wire. As shown in FIG. 21B, the stent 2100 is twisted, causing the opposing external channels 2108, created by the narrower side-to-side axis of the stent, to spiral around the stent 2100.

Figure 21C:
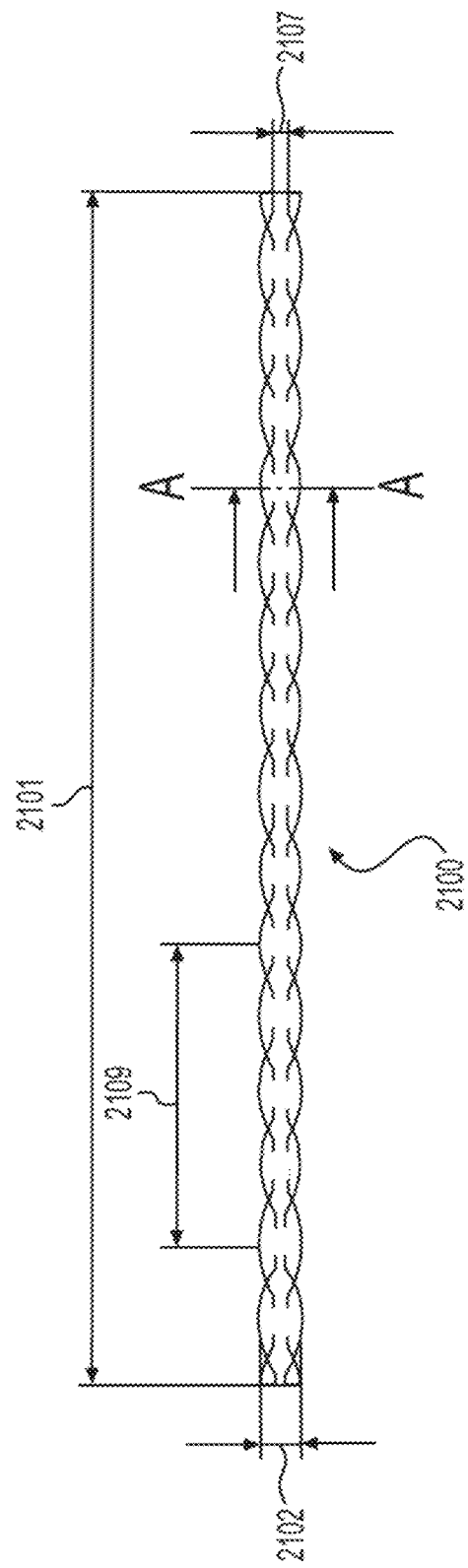

FIG. 21C is a side view of the stent 2100, showing the spiraling of the external channels 2108 around the central lumen 2107 (dashed lines). The inventors have surprisingly found that the fluid flow through the external channels 2108 is optimized by controlling the number of twists of the stent per inch (i.e., number of turns per 25.4 mm, shown in FIG. 21C as 2109, wherein one twist is a 360 degree rotation around the central axis of the stent). In addition, the present inventors have found that increasing the number of twists per inch (TPI) increases/improves the flexibility of the stent, as measured by deflection of the stent material with an equivalent amount of force applied. Increasing the TPI (for example, from 1 TPI to 2 TPI or from 2 TPI to 3 TPI) increases the amount of deflection, thereby indicating that higher TPI produces a more flexible stent. In some embodiments, the number of twists is at least, or more than, 1 twist per inch. In other embodiments, the number of twists is at least, or more than, 1.5 twists per inch. In still other embodiments, the number of twists is at least, or more than, 1.75 twists per inch. In yet other embodiments, the number of twists is between about 1.5 and 2.5 twists per inch. In even other embodiments, the number of twists is between about 1.75 and 2.25 twists per inch. In still other embodiments, the number of twists is about 2 twists per inch. In particular embodiments, the number of twists is at least, or more than, 2 twists per inch. In further embodiments, the number of twists equals 2 twists per inch. In other further embodiments, the number of twists is more than 2 twists per inch. The twisting of the stent may be carried out by any means known to one of ordinary skill in the art. In some embodiments, the stent may be formed in a straight, non-twisted, configuration, followed by twisting or machining to the desired number of twists/inch. In other embodiments, the stent 2100 may be formed or molded in the twisted shape. The polymer material from which the stent 2100 is made may be fixed in place in the twisted position by any means known to one of ordinary skill in the art, e.g., a heating process, etc.

Figure 21D:
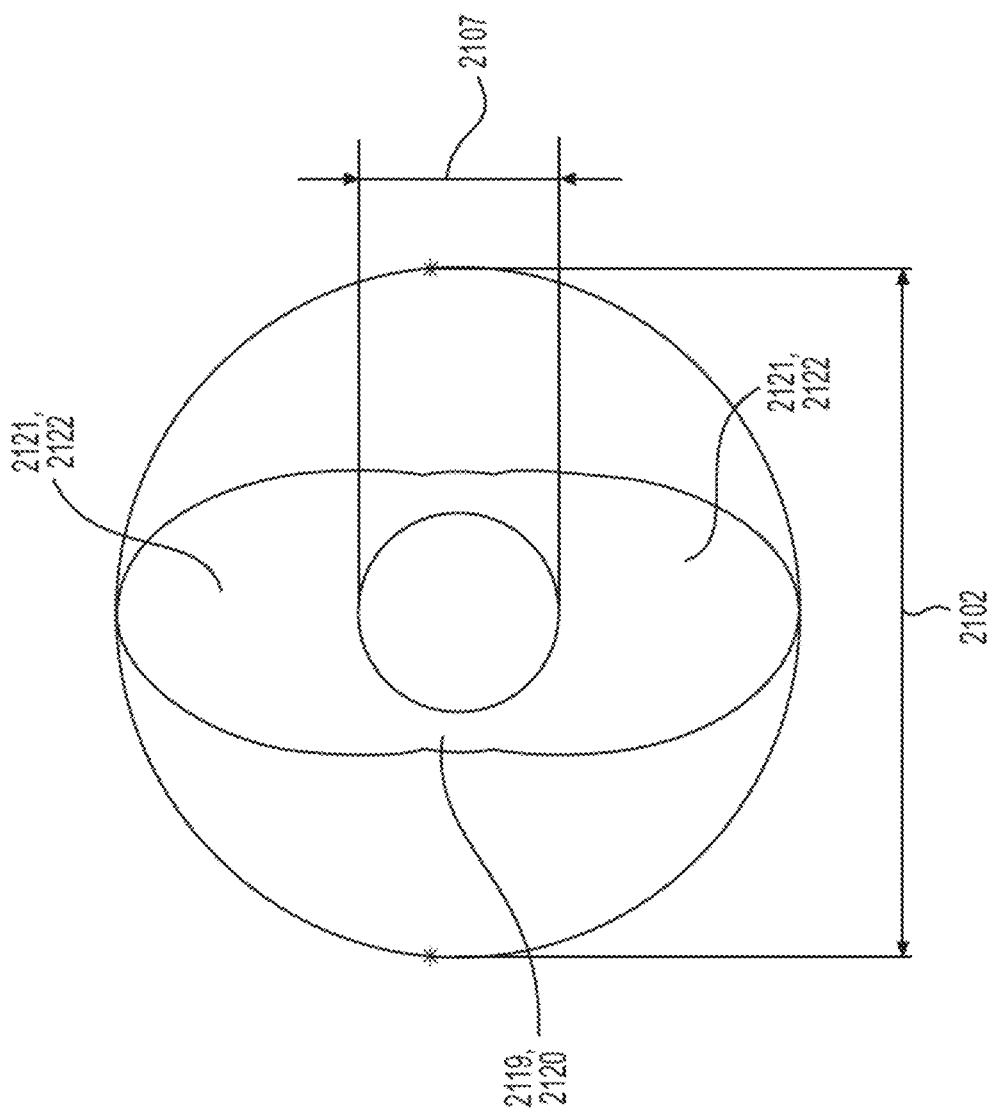

FIG. 21D shows a cross-section view of the stent 2100 at line A-A of FIG. 21C. In terms of orientation for describing the cross-section, the directions up, down, upper and lower refer direction lying on the main axis that bisects the cross-section of the stent into the longest mirror-image halves. Sides and side-to-side refer to a cross axis that is perpendicular to the main axis. In some embodiments, the central channel 2107 is between about 0.8 mm and about 1.2 mm in diameter. In other embodiments, the central channel 2107 is between about 0.9 mm and about 1.1 mm in diameter. In still other embodiments, the central channel 2107 is between about 0.95 mm and about 1.05 mm in diameter. In particular embodiments, the central channel 2107 is about 1 mm in diameter. In other particular embodiments, the central channel 2107 is 1 mm+/−0.1 mm in diameter. In some embodiments, the central channel is circular in cross section, in other embodiments, the central channel is oval or elliptical in cross section. The "diameter" of the central channel refers to the linear distance between the two farthest points within the lumen of the central channel along a straight line that passes through the center of the central channel in a cross-section.

Still referring to FIG. 21D, the cross-section of the stent comprises a central circle 2119 that surrounds the central channel 2107 and upper and lower bolsters 2121 that overlap the central circle 2119 and, in some embodiments, each other. The sides of the central circle 2119, between the points where the bolsters 2121 intersect with the central circle 2119, form the minor, thinner, walls 2120 of the stent around the central channel 2107. In some embodiments, the thickness of the minor walls 2120 is between about 0.1 mm and about 0.3 mm. In other embodiments, the thickness of the minor walls 2120 is between about 0.15 mm and about 0.25 mm. In particular embodiments, the thickness of the minor walls 2120 is about 0.2 mm+/−0.02 mm. In more particular embodiments, the thickness of the minor walls 2120 is about 0.2 mm+/−0.01 mm.

Still referring to FIG. 21D, the upper and lower bolsters 2121 are generally elliptical, oval or circular in shape. In the case of an oval or elliptical bolster 2121, the longest longitudinal axis of the bolster 2121 may lie oriented along the main axis of the cross section of the stent, as shown in FIG. 21D. In some embodiments, the longest longitudinal axis of an oval or elliptical bolster 2121 may lie oriented perpendicular to the main axis of the cross section of the stent. The bolsters 2121 form the major, thicker, walls of the stent.

In some embodiments, the thickness of the major walls 2122 is between about 0.9 mm and about 1.5 mm at the main axis. In other embodiments, the thickness of the major walls 2122 is between about 1.0 mm and about 1.4 mm at the main axis. In still other embodiments, the thickness of the major walls 2122 is between about 1.1 mm and about 1.3 mm at the main axis. In particular embodiments, the thickness of the major walls 2122 is about 1.2 mm+/−0.12 mm at the main axis. In more particular embodiments, the thickness of the major walls 2122 is about 1.2 mm+/−0.06 mm at the main axis.

In some embodiments, the bolsters 2121 have a side-to-side thickness of about 1.4 mm+/−0.14 mm. In more particular embodiments, the bolsters 2121 have a side-to-side thickness of about 1.4 mm+/−0.07 mm.

FIG. 21E shows an alternative cross-section for an embodiment of the stent 2100 and FIG. 21F shows the corresponding 3-D view. In some embodiments, the bolsters 2121 have a side-to-side thickness of between about 1.5 mm and about 1.9 mm. In other embodiments, the bolsters 1921 have a side-to-side thickness of between about 1.6 mm and about 1.8 mm. In particular embodiments, the bolsters 1921 have a side-to-side thickness of about 1.7 mm+/−0.17 mm. In more particular embodiments, the bolsters 1921 have a side-to-side thickness of about 1.7 mm+/−0.085 mm.

Figure 22B:
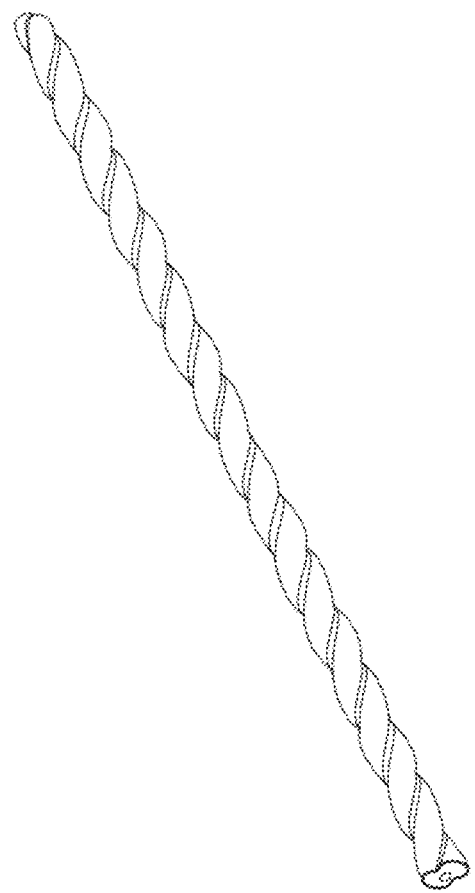
FIGS. 22A-B show an alternative feature for the embodiments of FIGS. 19A-21H.
Figure 22A:
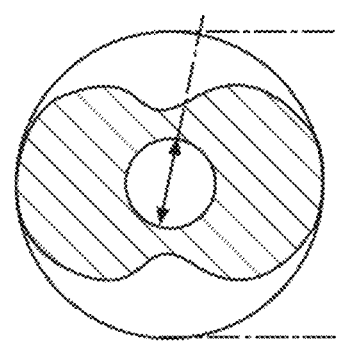

FIG. 21G shows another alternative cross-section for an embodiment of the stent 2100 and FIG. 21H shows the corresponding 3-D view. In some embodiments, the bolsters 2121 have a side-to-side thickness of between about 1.4 mm and about 1.5 mm. In particular embodiments, the bolsters 2121 have a side-to-side thickness of about 1.45 mm+/−0.145 mm. In more particular embodiments, the bolsters 2121 have a side-to-side thickness of about 1.45 mm+/−0.07 mm. FIG. 22A shows an exemplary alternative feature for the stents described in FIGS. 19A through 21H, wherein the junctions between the central circle and the bolsters are tapered or rounded. FIG. 22B is a 3-D rendering of the exemplary stent of FIG. 22A.

A biodegradable stent of the present application is useful for the treatment or palliation of strictures of a lumen in a subject in need thereof. In some embodiments, the lumen is a duct. In some further embodiments, the duct is a bile duct. In some still further embodiments, the bile duct is a hepatic, cystic, common bile or pancreatic duct. In some embodiments, the stricture is caused by, co-occurring with or related to a malignancy or a benign disease or condition of the liver, pancreas, duodenum, gall bladder or biliary tree. A biodegradable stent of the present application provides less complications in a subject, does not require costly removal procedures, has a lower clinical cost because it does not need sequential replacement and reduces loss of work time for the subject in need thereof.

In some embodiments, a biodegradable stent of the present application degrades by hydrolysis. In some embodiments, degradation of the biodegradable stent occurs on the outer surfaces, wherein the outer layer is degraded off and the stent progressively degrades from the outside towards the center.

A stent of the present application is capable of opening the lumen of a duct and allows bile to drain away. The present stent is biocompatible according to ISO 10993. The present stent is capable of withstanding compression without obstructing a duct. The present stent is loadable into a duodenal scope. The flexibility and column strength of the present stent is high enough to push the stent from the scope into a duct and can be deployed in a target location, and is visible, under fluoroscopy. A stent of the present application is insertable into a duct without perforating or otherwise damaging the duct. The ends of the stent minimize tissue granulation and the stent has high friction to prevent migration of the stent from the target location, while being capable of repositioning after deployment. The present stent is removable after implantation without damage to the tissue of the lumen. A stent of the present invention has a shelf life of 1 to 2 years after sterilization.

The present stent is typically made from a polymer material, plastics, metals, or alloys. Notable variations exist within each type. In certain embodiments, the stent is made from a non-polymer material. Examples of such materials include, but are not limited to, stainless steel, cobalt alloys such as cobalt-chromium, titanium alloys, tantalum, niobium, tungsten, molybdenum and nitinol. For example, self-expanding metal stents are generally made from nitinol, while some balloon-expandable metal stents are made from stainless steel. A coating, such as polyurethane coating, may be used to prevent non-polymer stent material from coming into direct contact with its surroundings. The coating slows down the rate of in-growth, allowing the stent to remain in the patient with a lower potential for side effects.

The stent may also be made with a bioabsorbable material. Examples of bioabsorbable materials include, but are not limited to, polylactic acid or polylactide (PLA), polyglycolic acid or polyglycolide (PGA), poly-ε-caprolactone (PCL), polyhydroxybutyrate (PHB), polyethylene glycol (PEG), p-dioxanone, poly-(p-dioxanone) (PPDO), trimethylene carbonate, caprolactate and co-polymers thereof.

In one embodiment, the bioabsorbable material is degraded based on varying levels of pH. For example, the material may be stable at a neutral pH but degrades at a high pH. Examples of such materials include, but are not limited to chitin and chitosan. In another embodiment, the bioabsorbable material is degradable by enzymes, such as lysozymes.

In another embodiment, the polymers include transparent plastic polymers, thermoplastic polyurethane or silicone polymers.

In another embodiment, the elongated body comprises a combination of a polymer and a non-polymer material.

In another related embodiment, the elongated stent body is made of a magnesium and chitin alloy.

In another related embodiment, the elongated stent body is made with a magnesium core coated with a chitin chitosan, N-acylchitosan hydrogel outer layer. The magnesium core may additionally include rare earth materials.

In another related embodiment, the elongated stent body is made of a chitin and chitosan, N-acylchitosan hydrogel and magnesium alloy with raw earth elements.

In another embodiment, the bioabsorbable material may absorb moisture and expand in situ at the treatment site. For example, the stent made of chitin or a variable copolymer of chitin and PLGA or chitin and magnesium and other rare earth minerals would swell once it comes into contact with various body fluids. In one embodiment, the stent has a pre-implantation diameter $D_{pre}$ (i.e., dry diameter) of 2.8 mm and is expandable to a post-implantation diameter $D_{post}$, (i.e., wet diameter) of 3.3 mm after exposure to body liquid in a lumen. As used hereinafter, the "pre-implantation diameter $D_{pre}$" refers to the largest diameter of a stent body before implantation and the "post-implantation diameter $D_{post}$" refers to the largest diameter of the stent body after implantation.

In some embodiments, the stent is made of a fast-absorbing bioabsorbable material that degrades within about two to four weeks. In particular embodiments, the fast-absorbing bioabsorbable material is a mixture or combination of PEG and p-dioxanone. In a further embodiment, PEG comprises about 10-30% and p-dioxanone comprises about 70-90% of the mixture or combination. In a still further embodiment, PEG comprises about 15-25% and p-dioxanone comprises about 75-85% of the mixture or combination. In an even further embodiment, PEG comprises about 12-22% and p-dioxanone comprises about 78-82% of the mixture or combination. In a yet further embodiment, PEG comprises about 20% and p-dioxanone comprises about 80% of the mixture or combination.

In some embodiments, the stent is made of a medium-absorbing bioabsorbable material that degrades within about three to six weeks. In particular embodiments, the medium-absorbing bioabsorbable material is PPDO, or a copolymer thereof.

In some embodiments, the stent is made of a medium-to-slow-absorbing bioabsorbable material that degrades within about six week to four months.

In some embodiments, the stent is made of a slow-absorbing bioabsorbable material that degrades within about four to six months. In particular embodiments, the fast-absorbing bioabsorbable material is a copolymer of lactide, trimethylene carbonate and caprolactate. In particular embodiments, the copolymer comprises a percentage composition of PLA/trimethylene carbonate/caprolactate that is about 70-80/10-20/5-15, respectively. In further embodiments, the copolymer comprises a percentage composition of PLA/trimethylene carbonate/caprolactate that is about 72-76/13-17/9-13, respectively. In still further embodiments, the copolymer comprises a percentage composition of PLA/trimethylene carbonate/caprolactate that is about 74/15/11, respectively.

In some embodiments, the bioabsorbable material is coated or impregnated with a biocompatible radio-opaque substance to aid in visualization of the stent during or after emplacement, for example by fluoroscopy or x-ray. In some embodiments, the radio-opaque substance is a $BaSO_4$ solution. In further embodiments, the solution comprises about 10-25% $BaSO_4$. In still further embodiments, the solution comprises about 12-22% $BaSO_4$. In even further embodiments, the solution comprises about 17% $BaSO_4$. In some embodiments, the radio-opaque substance comprises metal particles. In further embodiments, the particles are nanoparticles. In exemplary non-limiting embodiments, the metal comprises tantalum.

In some embodiments, the stent is a biliary stent with a diameter of 5 F to 12 F and a length of 10-180 mm. In some embodiments, the stent is a pancreatic stent with a diameter of 3 F to 11.5 F and a length of 20-250 mm. In some embodiments, the biliary or pancreatic stent is a self-expanding metal stent. In some embodiments, the biliary or pancreatic stent is made of a polymer material. In some embodiments, the biliary or pancreatic stent is constructed to have a minimal strength retention of 12 days, 25 days or 12 weeks, where strength retention is defined by the presence of at least 10% of the initial strength parameter (e.g. the stent remains intact with no breaks, tested in a simulated degradation model). In some embodiments, the biliary or pancreatic stent contains by weight 16.8% PEG, 67.2% p-dioxanone (in the form of a 20%/80% PEG/p-dioxanone coplymer) and 16% BaSO4 (barium sulfate), and has minimal strength retention of 12 days. In some embodiments, the biliary or pancreatic stent contains by weight 84% Poly(para-dioxanone) and 16% BaSO4, and has minimal strength retention of 25 days. In some embodiments, the biliary or pancreatic stent contains by weight 62.16% lactide, 12.6% trimethylene carbonate, 9.24% caprolactone (in the form of a 74%/15%/11% coplymer) and 16% BaSO4, and has a has minimal strength retention of 12 weeks.

In some embodiments, the biliary stent experiences initial surface degradation upon implantation, which allows for bile cleansing. In some embodiments, the biliary stent comprises a double-channel helical twist on the exterior surface to allow bile flow on the outside of the stent. In comparison to other stents, the biliary stent of the present application provides better simulated flow rates, better simulated migration resistance and better crush resistance.

In another embodiment, the bioabsorbable material is embedded with, or configured to carry, various agents or cells. The agents may be coupled to the outer and/or inner surfaces of stent body or integrated into the bioabsorbable material itself. In one embodiment, the bioabsorbable stent has a hollow center lumen so that agents may be placed inside the lumen to increase the dose release. The stent can additionally have multiple reservoirs, one inside the other, so that when the outer layer is absorbed the next reservoir is exposed and a further release of a larger dose of the chosen agents or cells. The chosen agent or cells may also be mixed with the polymer for sustained release.

Examples of agents that can be embedded into or carried by a stent include, but are not limited to, small molecule drugs, biologicals and gene transfer vectors. Examples of small molecule drugs include, but are not limited to, sirolumus, rapamycian, and other antiproliferating agent.

Examples of biologicals include, but are not limited to, antimicrobial agents and chemotherapeutic agents.

The term "antimicrobial agent" as used in the present application means antibiotics, antiseptics, disinfectants and other synthetic moieties, and combinations thereof, that are soluble in organic solvents such as alcohols, ketones, ethers, aldehydes, acetonitrile, acetic acid, formic acid, methylene chloride and chloroform. Classes of antibiotics that can possibly be used include tetracyclines (i.e., minocycline), rifamycins (i.e., rifampin), macrolides (i.e., erythromycin), penicillins (i.e., nafcillin), cephalosporins (i.e., cefazolin), other beta-lactam antibiotics (imipenem, aztreonam), aminoglycosides (i.e., gentamicin), chloramphenicol, sulfonamides (i.e., sulfamethoxazole), glycopeptides (i.e., vancomycin), quinolones (i.e., ciprofloxacin), fusidic acid, trimethoprim, metronidazole, clindamycin, mupirocin, polyenes (i.e., amphotericin B), azoles (i.e., fluconazole) and beta-lactam inhibitors (i.e., sulbactarn).

Examples of specific antibiotics that can be used include minocycline, rifainpin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfiloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole and nystatin. Other examples of antibiotics, such as those listed in U.S. Pat. No. 4,642,104, herein incorporated by reference, will readily suggest themselves to those of ordinary skill in the art. Examples of antiseptics and disinfectants are thymol, a-terpineol, methylisothiazolone, cetylpyridinium, chloroxylenol, hexachlorophene, cationic biguanides (i.e., chlorhexidine, cyclohexidine), methylenechloride, iodine and iodophores (i.e., povidone-iodine), triclosan, firanmedical preparations (i.e., nitrofurantoin, nitrolurazone), methenamine, aldehydes (i.e., glutaraldehyde, formaldehyde) and alcohols. Other examples of antiseptics and disinfectants will readily suggest themselves to those of ordinary skill in the art.

The stent of the present application may also be prepared with antimicrobial agents in other ways customary in the art. For example, the stent may be made in its entirety or in part of an antimicrobial polymer, or at least one surface of the stent may have embedded, by ion beam assisted deposition or co-extrusion techniques, therein with atoms of an antimicrobial polymer. Other suitable examples can be found in the art, for example, U.S. Pat. No. 5,520,664, which is incorporated herein by reference.

Chemotherapeutic agents can be coupled with the stent of the present application in a manner analogous to that of antimicrobial agents. Exemplary chemotherapeutic agents include but are not limited to cis-platinum, paclitaxol, 5-flourouracial, gemcytobine and navelbine. The chemotherapeutic agents are generally grouped as DNA-interactive agents, antimetabolites, tubulin-interactive agents, hormonal agents, hormone-related agents, and others such as asparaginase or hydroxyurea. Each of the groups of chemotherapeutic agents can be further divided by type of activity or compound. The chemotherapeutic agents used in combination with the anti-cancer agents or benzimidazoles of this application include members of all of these groups. For a detailed discussion of the chemotherapeutic agents and their method of administration, see Dorr, et al, Cancer Chemotherapy Handbook, 2d edition, pages 15-34, Appleton & Lange (Connecticut, 1994), herein incorporated by reference.

Examples of DNA-Interactive agents include, but are not limited to, alkylating agents, DNA strand-breakage agents; intercalating and nonintercalating topoisomerase II inhibitors, and DNA minor groove binders. Alkylating agents generally react with a nucleophilic atom in a cellular constituent, such as an amino, carboxyl, phosphate, or sulfhydryl group in nucleic acids, proteins, amino acids, or glutathione. Examples of alkylating agents include, but are not limited to, nitrogen mustards, such as chlorambucil, cyclophosphamide, isofamide, mechlorethainine, Melphalan, uracil mustard; aziridines, such as thiotepa; methanesulfonate esters such as busulfan; nitroso, ureas, such as cannustine, lomustine, streptozocin; platinum complexes, such as cisplatin, carboplatin; bioreductive alkylator, such as mitomycin, and procarbazine, dacarbazine and altretamine. DNA strand breaking agents include, but are not limited to, bleomycin. Intercalating DNA topoisomerase II inhibitors include, but are not limited to, intercalators such as amsacrine, dactinomycin, daunorubicin, doxorubicin, idarubicin, and mitoxantrone.

Nonintercalating DNA topoisomerase II inhibitors include, but are not limited to etoposide and teniposide. DNA minor groove binders include, but are not limited to, plicamycin.

Antimetabolites interfere with the production of nucleic acids by one or the other of two major mechanisms. Some of the drugs inhibit production of the deoxyribonucleoside triphosphates that are immediate precursors for DNA synthesis, thus inhibiting DNA replication. Some of the compounds, for example, purines or pyrimidines, are sufficient to be able to substitute for them in the anabolic nucleotide pathways. These analogs can then be substituted into the DNA and RNA instead of their normal counterparts. The antimetabolites useful herein include: folate antagonists such as methotrexate and trimetrexate pyrimidine antagonists, such as fluorouracil, fluorodeoxyuridine, CB3717, azacytidine, cytarabine, and floxuridine purine antagonists include mercaptopurine, 6-thioguanine, fludarabine, pentostatin; sugar modified analogs include cyctrabine, fludarabine; ribonucleotide reductase inhibitors include hydroxyurea. Tubulin interactive agents act by binding to specific sites on tubulin, a protein that polymerizes to form cellular microtubules. Microtubules are critical cell structure units. When the interactive agents bind on the protein, the cell cannot form microtubules tubulin interactive agents including vincristine and vinblastine, both alkaloids and paclitaxel.

Hormonal agents are also useful in the treatment of cancers and tumors. They are used in hormonally susceptible tumors and are usually derived from natural sources. These include: estrogens, conjugated estrogens and ethinyl estradiol and diethylstilbestrol, chlorotrianisene and idenestrol; progestins such as hydroxyprogesterone caproate, medroxyprogesterone, and megestrol; androgens such as testosterone, testosterone propionate; fluoxymesterone, metbyltestosterone; adrenal corticosteroids are derived from natural adrenal cortisol or hydrocortisone. They are used because of their anti-inflammatory benefits as well as the ability of some to inhibit mitotic divisions and to halt DNA synthesis. These compounds include prednisone, dexamethasone, methylprednisolone, and prednisolone.

Hormone-related agents include, but are not limited to, leutinizing hormone releasing hormone agents, gonadotropin-releasing hormone antagonists and anti-hormonal agents. Gonadotropin-releasing hormone antagonists include leuprolide acetate and goserelin acetate. They prevent the biosynthesis of steroids in the testes and are used primarily for the treatment of prostate cancer.

Antihormonal agents include antiestrogenic agents such as tamosifen, antiandrogen agents such as Flutamide; and antiadrenal agents such as mitotane and aminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor.

Gene transfer vectors are capable of introducing a polynucleotide into a cell. The polynucleotide may contain the coding sequence of a protein or a peptide, or a nucleotide sequence that encodes a iRNA or antisense RNA. Examples of gene transfer vectors include, but are not limited to, non-viral vectors and viral vectors. Non-viral vectors typically include a plasmid having a circular double stranded DNA into which additional DNA segments can be introduced. The non-viral vector may be in the form of naked DNA, polycationic condensed DNA linked or unlinked to inactivated virus, ligand linked DNA, and liposome-DNA conjugates. Viral vectors include, but are not limited to, retrovirus, adenovirus, adeno-associated virus (AAV), herpesvirus, and alphavirus vectors. The viral vectors can also be astrovirus, coronavirus, orthomyxovirus, papovavirus, paramyxovirus, parvovirus, picomavirus, poxvirus, or togavirus vectors.

The non-viral and viral vectors also include one or more regulatory sequences operably linked to the polynucleotide being expressed. A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

In one embodiment, the gene transfer vector encodes a short interfering RNA (siRNA). siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing. In another embodiment, the gene transfer vector encodes an antisense RNA.

Examples of cells include, but are not limited to, stem cells or other harvested cells.

Manufacture of Stent

The stent body and surface channels can be laser cut, water jet cut, extruded, stamped, molded, lathed or formed. In one embodiment, the stent is cut from a single polymer tube that may be extruded. The tube may be hollow or the center may be cored out at varying diameters suitable for the particular indication.

The stent is then etched and is formed on a suitable shaping device to give the stent the desired external geometry. Both the synthetic collar techniques and in vitro valuation techniques show the remarkable ability of stents of the present application to convert acting force into deformation work absorbed by the angled structure, which prevents excessive scaffolding stress, premature material fatigue and accelerated obsolescence.

The stent of the present application may be formed in such a way as to allow fluid flow to change in the pitch of the flow to improve flow dynamics and to speed the flow of fluids throughout the device. From a tight radial design to a more longitudinal design.

In one embodiment spiral surface channels with large cross-section areas are formed to accommodate large volumes of body fluid. In another embodiment, multiple channels with small cross-section area are formed to accommodate large volumes of body fluid. In another embodiment, the stent body contains a large center lumen to allow for fluid flow and a plurality of small cross-section area channels on the surface to stabilize the stent in vivo.

In another embodiment, the lips of the channel walls are taped to increase the surface area for fluid flow and grip. Changes in the depth of the pitch of the channels will also have an impact on fluid flow and stability.

In one embodiment, the stent is formed on a shaping tool that has substantially the desired contour of the external stent dimensions. In the event the stent is to be shaped to the dimensions of a particular lumen, optical photography and/or optical videography of the target lumen may be conducted prior to stent formation. The geometry of corresponding zones and connector regions of the stent then can be etched and formed in accordance with the requirements of that target lumen. In particular, if the topography of the biliary duct of a particular patient is captured optically and the appropriate dimension provided, a patient specific prosthesis can be engineered. These techniques can be adapted to other non-vascular lumens but is very well suited for vascular applications where patient specific topography is a function of a variety of factors such as genetics, lifestyle, etc.

Unlike stents made from shape memory metals, the stents of the present application can take on an infinite number of characteristic combinations as zones and segments within a zone can be modified by changing angles, segment lengths, segment thicknesses, pitch during the etching and forming stages of stent engineering or during post formation processing and polishing steps. Moreover, by modifying the geometry, depth, and diameter of the channels between zones, additional functionality may be achieved, such as flexibility, increased fluid transport, and changes in friction.

Use of Stent

A stent of the present application is used to support a target site in a vessel, duct or lumen and optimize the flow of bodily fluids in a subject in need thereof. Following identification of the target site, an entry portal is established into a vessel, duct or lumen leading to the target site. A guide wire is advanced through the entry portal and vessel, duct or lumen to or through the target site. The stent is then pushed along the guide wire until it reaches the target site and is emplaced there, followed by the withdrawal of the guide wire.

Kit

Another aspect of the present application relates to a kit. The kit comprises at least one stent of the present application. In some embodiments, the kit further comprises a guide wire for emplacing the stent at a target location. In some embodiments, the kit further comprises a pushing catheter for moving the stent along the guide wire. In some embodiments, the kit comprises an introducer sheath or introducer tube. In some embodiments, the kit further comprises a cannula. In some embodiments, the kit further comprises a sphincterotome. In some embodiments, the kit comprises a radio-opaque dye.

EXAMPLES

Example 1: Endoscopic Retrograde Cholangio-Pancreatography (ERCP)

In a subject in need thereof, ECRP is a procedure performed to diagnose and treat diseases of the gallbladder, bile system, pancreas and liver.

An endoscope is passed though the mouth of the subject down through the stomach and into the duodenum, where the location of the entry of the bile duct into the small intestine is identified. The scope has a working channel (WC) through which a cannula (catheter) is fed and a practitioner "cannulates" the bile duct (to introduce the cannula into the bile duct). A guidewire is sent thru the center lumen of the cannula and is passed thru the bile duct and into the liver. The cannula is removed and a sphincterotome is introduced. A practitioner cuts the papilla (the sphincter into bile duct) with the sphincterotome and the sphincterotome is withdrawn. An absorbable polymer stent as described herein is placed over the guide wire and pushed into the bile duct with a pushing catheter, allowing proper drainage through the bile duct. Depending upon the need of the subject, the stent is made of a fast-absorbing polymer, medium-absorbing polymer or slow-absorbing polymer. The pushing catheter and guidewire are withdrawn from the subject.

Example 2: Simulated Flow Test

The setup for the simulated flow test involves a water container that is filled with tap water and connected with 6×9 mm silicone tube. The tube is further connected with a Y connector where one of the openings is connected to a pressure measurement device and another opening is attached to the silicone tube integrated into an endoscope/bile duct model, certified by physicians. The Y connector joint will be secured with cable ties against leakage. At the end of the silicone tube, a one-way stopcock should be attached for controlling water flow (on/off). Following the above setup, every stent is tested individually and inserted into the tube and positioned with help of a pushing catheter. Once the stent is positioned, stricture is made on the silicone tube by tightening cable ties around the stent, creating stricture of similar diameter as that of the stent. A pressure measurement device should set to 0 mbar before starting the test. Once the setup is secured, water should be released carefully from big water container and the flow will be adjusted till pressure measurement device displays 19 mbar. This value is calculated and derived from 20 cm H2O (I). As soon as the value sets to 19 mbar (I), 70 ml (II) of water will be collected in a measuring beaker and time for collecting will be counted with stop watch. The values considered in this protocol such as 70 ml and 19 mbar are understood from following references (these values are considered as worst case scenario): Csendes et al 1988—Common Bile Duct Pressure in Patients With Common Bile Duct Stones With or Without Acute Suppurative Cholangitis states that common duct pressure values above 20 cm $H_2O$ is the maximal values of normal; and Dennison & Farrell 2016—Pass PCCN—6. The G1 System states that Gallbladder stores bile and has a storage capacity of 50 to 70 ml. After every test, a beaker should be cleaned with a cloth to avoid reading errors/irregularities. The above mentioned procedure is followed for every single stent tested.

Figure 23:
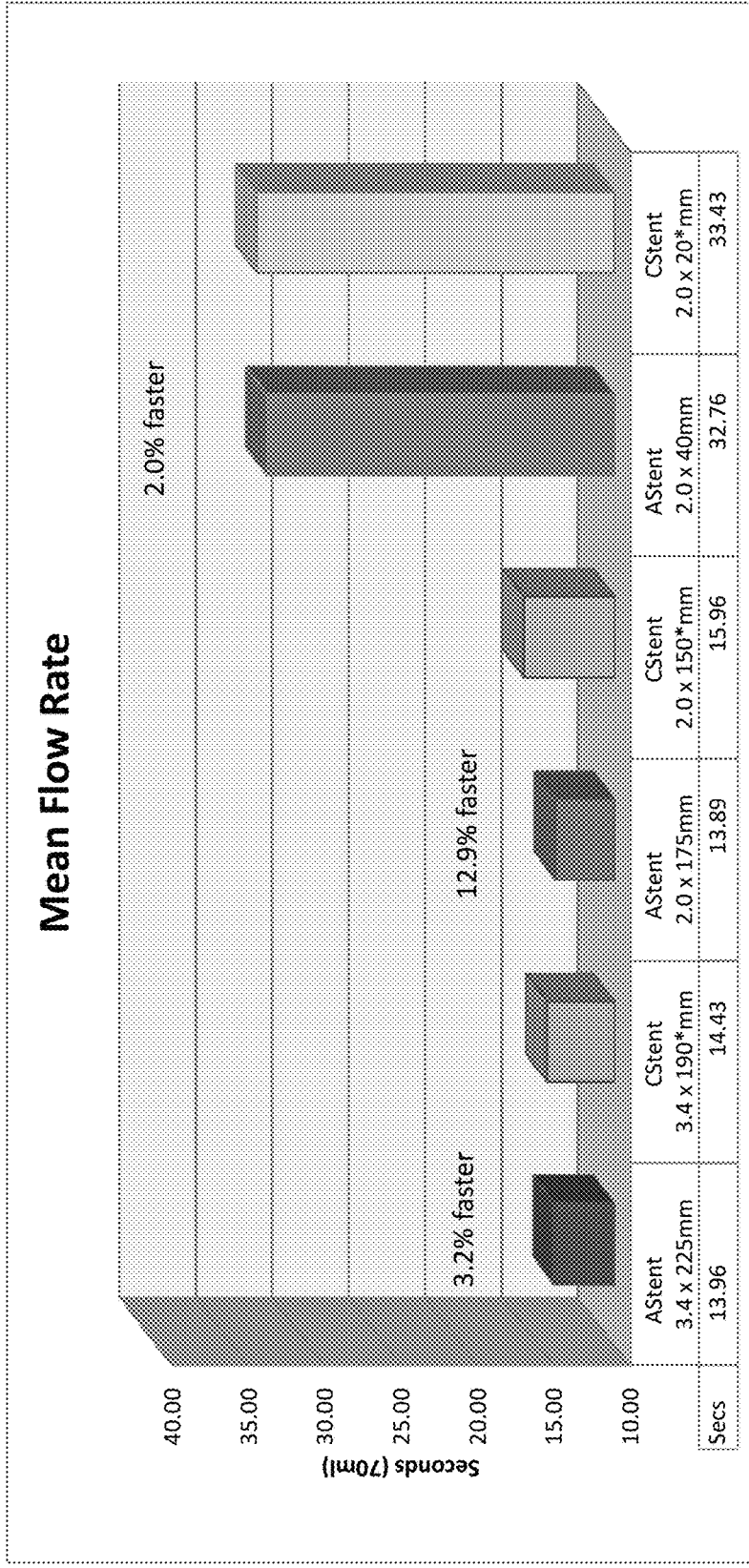
FIG. 23 shows the results of a simulated flow test involving a stent of the present application.

FIG. 23 shows the results of simulated flow model comparing the stent of the present application ("AStent") with some commercially available biliary and pancreatic stent (the control stents or "CStent"). The stent of the present application has a double-channel helical twist on the exterior surface of the stent body. The control stents do not have such a surface feature. In the simulated flow test, the stent of the present application ("AStent" in the figure) has a higher flow rate than the control stents ("CStent" in the figure) for all the comparisons shown (higher flow rate means less time needed to drainage the defined worst-case amount of simulated bile fluid). In particular, the 2.0×175 mm stent of the present application has a 12.9% faster mean flow rate than the comparable control stent, as used herein, the notion 2.0×175 mm, indicates a diameter of 2.0 mm and a length of 175 mm. A total of two test samples were tested for the stent sizes described. Each stent was tested five times for a total of ten data points per stent based on the recommendation in ASTM F2081.

Example 3: Simulated Migration Resistance Test

An endoscope model/biliary model is laid horizontally in a water bath at 37° C. A PTFE tube shall be fitted into model acting as bile duct. The stent is placed at a starting point of the tube and the end point of the tube will face towards a horizontal Zwick machine and load cell. A nylon string is inserted through the inner lumen of the stent and attached to the load cell of machine. The nylon string is fitted with a hook that helps to pull the stent through tube. Once the setup is secured, a protocol is created in the Zwick system, defining all parameters such as speed (200 mm/min) and travel distance (120 mm). After each stent is tested, the anti-migration struts are visually inspected. Any broken or damaged anti-migration struts observed shall be photographed and documented in the report. As the stent is pulled through the model, the load cell measures the friction force and the force values are automatically recorded in the Zwick system. The peak friction forces of each stent tested are documented in the report. Each stent was tested five times for a total of ten data points per stent based on the recommendation in ASTM F2081.

Figure 24:
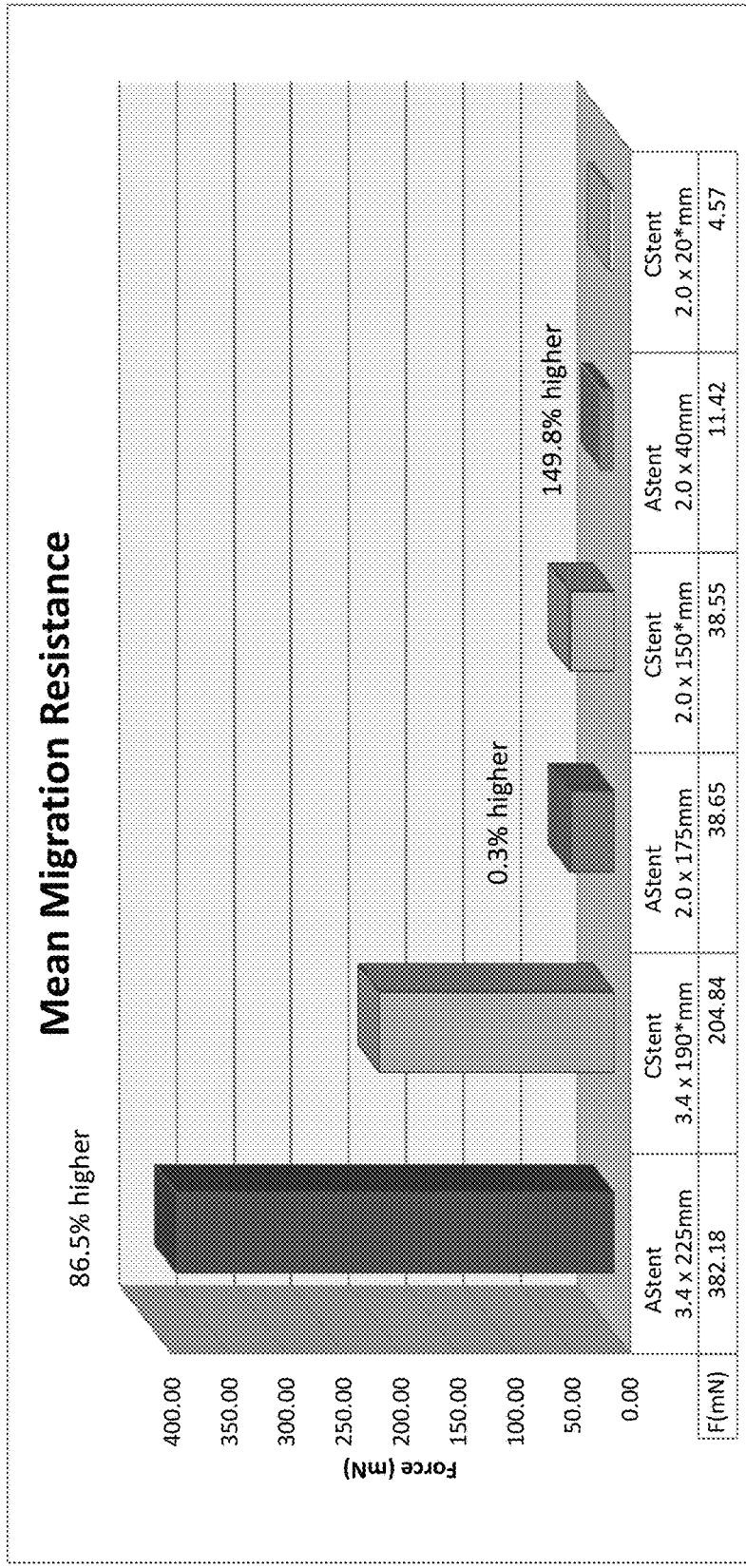
FIG. 24 shows the results of a simulated migration resistance test involving a stent of the present application.

FIG. 24 shows the results of a simulated migration resistance test comparing the stent of the present application to control biliary and pancreatic stents. The stent of the present application has higher mean migration resistance compared to the control stents for all the comparisons shown. In particular, the 2.0×40 mm stent of the present application has 149.8% higher mean migration resistance than the control stent.

Example 4: Crush Resistance Test

Figure 25:
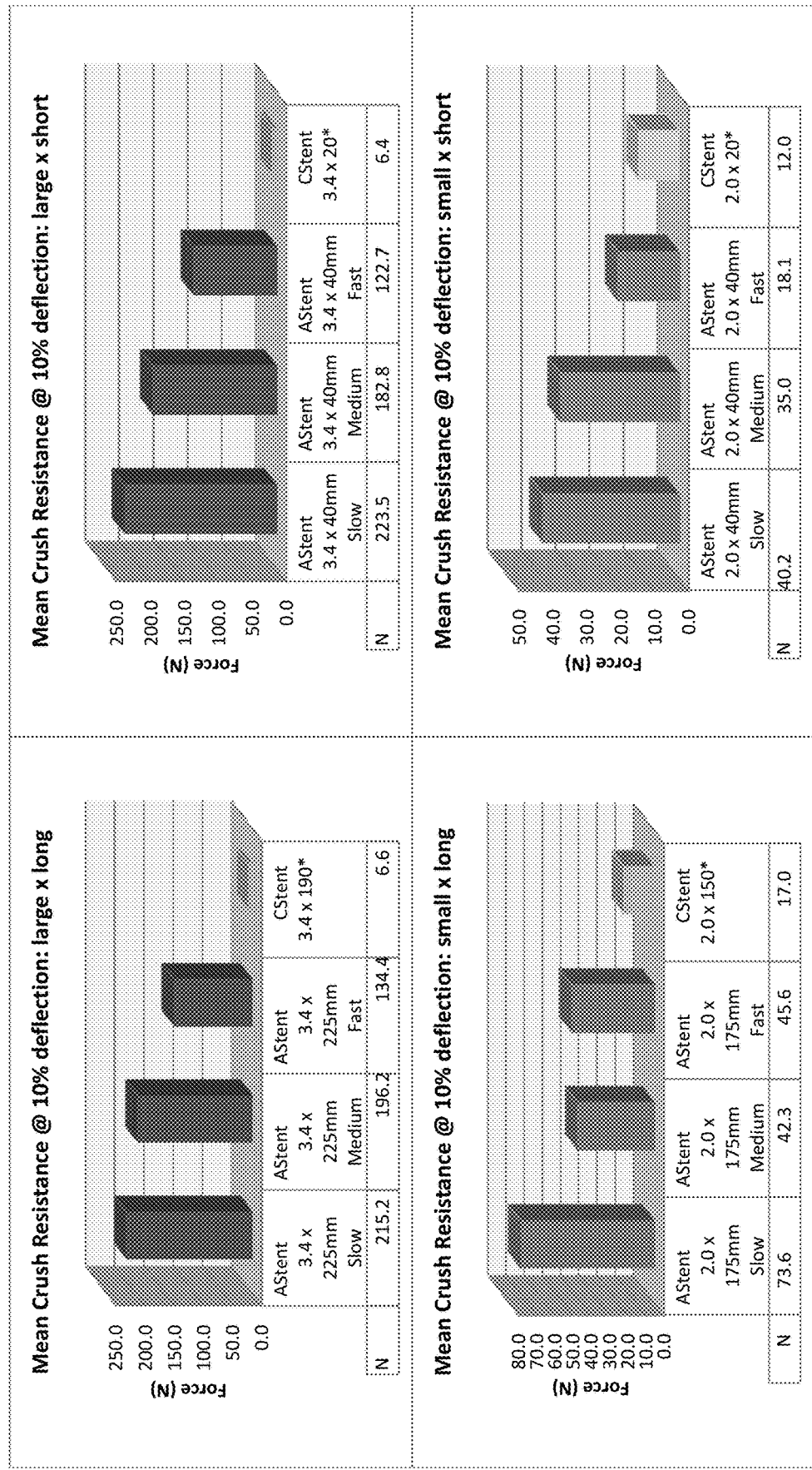
FIG. 25 shows the results of a crush resistance test involving a stent of the present application.

FIG. 25 shows the results of crush resistance tests comparing the stent of the present application to control biliary and pancreatic stents. The tests are carried out using a 6 mm flat probe on a tensile test machine. The stent is laying on a flat plate and the probe comes down on the stent from the top. The stent is compressed 10% of the diameter of the stent and then peak force is measured, e.g., 2.0 mm stent: 10% deflection=0.2 mm deflection; 2.6 mm stent: 10% deflection=0.26 mm deflection; 3.4 mm stent: 10% deflection=0.34 mm deflection.

Stents of the present application with different degradation profiles were tested (shown as "slow", "medium" and "fast" in the figure). In each case, the stent of the present application showed superior mean crush resistance compared to the control stents. In particular, for each comparison shown, the stents of the present application which have a slow degradation profile have a significantly elevated level of crush resistance in comparison to the control stents.

Example 5: Animal Tests

The stents of the present application have been tested successfully in animal studies. A study was designed to evaluate the feasibility of the fully biodegradable plastic biliary stent in a clinically relevant porcine common bile duct model determining deliverability, safety, and the biological reaction of the bile duct.

Two animals were treated with stents in the biliary ducts. Animals were clinically evaluated throughout the study period. After 24 day follow-up angiography and endoscopy, animals were then taken off study and saved for future use. Swine are an established model for physiological monitoring and bile duct studies. The size of porcine bile ducts can approximate that of a human and will accommodate the necessary instrumentation. Animals were fasted 72 hours, received EnerCal for nutritional supplement, prior to Day 0 procedures. On Day 0, animals were given an injection of Telazol for sedation and then transported to the prep room once sufficiently sedate. Animals were administered 5% Isoflurane via nose cone for anesthetic induction then intubated. General anesthesia was maintained with Isoflurane in oxygen, administered via a standard rebreathing system.

An endoscope was introduced orally and then traversed through the esophagus, stomach and into the duodenum. The ampullary region was then identified and the biliary duct was cannulated with a catheter. Angiograms were recorded using non-ionic contrast to help visualize the biliary ducts. Stents were implanted in the bile ducts of each animal by advancing over wire guide to target site. One animal (P272) had 4 stents implanted in the bile ducts with the possibility of one being unsuccessful and falling out and the other animal (P273) had 3 stents implanted in the pancreatic and bile ducts. On second implant animal P273 had 3 stents implanted. Stents were either placed parallel or lined up in a row. The number, order and location of stent implant was at the discretion of operator and was chosen based on accessibility. An angiogram was recorded to verify placement. Following post-stent angiography/fluoroscopy in chronic animals, wire guides and catheters were withdrawn along with the endoscope. The anesthesia was discontinued and the animal allowed to recover in a raised floor pen.

For interim/follow-up procedures, at 72 hours, 6, 14, and 24 days following implantation, animals were prepped in the same manner as for implant (with a 48 hour fasting). On second implant for P273 animal was fasted 24 hours prior to 7, 14, and 17 day follow-ups. Endoscope was advanced to duodenum to visualize the stents. Angiograms of the bile ducts were taken using non-ionic contrast agent. For interim procedures the endoscope was withdrawn. The anesthesia was discontinued and the animal allowed to recover in a raised floor pen. For endpoint procedures (Day 24), anesthesia was discontinued and the animal allowed to recover in a raised floor pen. This study was considered complete as no devices were visible and animals were then used in additional studies (P272) or reimplanted (P273). At the endpoint (Day 17) of second implant, for P273, and completion of additional studies, for P272, animals received a 10000 u IV heparin bolus (P272 only) and were sacrificed and necropsied and bile ducts were sent for histopathology.

Both animals had no significant clinical observations during the in-life period. Recovery after every procedure was uneventful and animal returned to normal within 24 hours. In general, the follow-up procedure consisting of final angiograms to visualize stents in bile ducts. No abnormal findings were observed during the follow-up procedure in P272 or P273. After the final images were captured, animals were taken off anesthesia and allowed to recover. They were then used to test other devices at a later date (P272) or reimplanted (P273). Once those studies were complete a 10,000 unit bolus of Heparin was administered and allowed to circulate (P272 only) then the animals were euthanized with 40 mEq of Potassium chloride IV while under a deep plane of anesthesia. Death was verified by a lack of vital signs. Animals were then transported to necropsy for vessel harvesting procedures. Pancreas and bile ducts were sent for histopathology.

Histopathology involved taking the formalin fixed bile duct from the gall bladder to the duodenum plus surrounding tissues including pancreas for histopathology. The bile duct was sectioned every 1-1.5 cm from the gall bladder to the duodenum including the duodenal papilla. A distinct pancreatic duct was not identified on gross examination. Slides were processed for paraffin histopathology using routine techniques, cut at 5 microns, and stained with hematoxylin and eosin stain. The outcome of the study showed that, after gross examination, the liver, bile duct, and duodenum were normal with no important changes. Microscopically, no lesions were identified in the bile duct at any level. Liver and duodenum were similarly normal. On gross examination, the pancreas was normal. A distinct pancreatic duct was not identified. Loose tissues between the pancreas and duodenum were examined grossly and microscopically for pancreatic ducts, but none were found. The pancreatic duct was found grossly and microscopically within pancreatic lobules. No important changes other than early autolysis were found. Three small (up to 4 mm) areas of chronic inflammation (eosinophilic granulomas) were present in the peri-pancreatic connective tissue near the duodenum. The pancreatic ducts were not identified within the eosinophilic granulomas.

Example 6: Human Tests

The stents of the present application have been placed in a study involving twenty-four patients. The study assessed the safety and efficacy of the plastic biliary stent in patients with benign and malign biliary strictures and who suffer under jaundice and pruritus. Since this device is deemed to drain obstructed biliary or pancreatic ducts the aim is to improve bile flow in patients suffering from benign and malignant biliary strictures. The study had first and second endpoints. The first endpoint concerned safety, which the study defined in terms of complications seen in PEP (Post-Endoscopic Perforation) like bleeding, perforation (bile/duodenum), misplacement, migration, bile occlusion, duct abrasion, duodenal abrasion, cholangitis, severe pain and all-death. The second endpoint concerned efficacy, which the study defined in terms of the following markers of procedural success: stent loadability; trackability over guide wire; pushability with push-catheter; flexibility; force required to implant device; visualization by fluoroscopy; stent reposition when required; deployment accuracy; device deployment time.

The patient cohort consisted of twenty-four patients (average age 54.5 years, female 42%, male 58%); the variety of patient conditions included malignant biliary structure (3), benign biliary structure (21), cholocystitis (2), cholelethiasis (2), choledocholithiasis (11), cholangitis (6), pancreatitis (3), ampullary cancer (1), pancreatic head cancer (2). The study proved successful procedurally for all patients in terms of stent loadability (clinical ratings: 78% excellent, 17% good, 4% poor); stent trackability over guide wire (clinical ratings: 87% excellent, 9% good, 4% fair); stent pushability with push catheter (clinical ratings: 74% excellent, 13% good, 9% fair, 4% poor; force required to implant device (clinical ratings: 57% excellent, 21% good, 13% fair, 9% poor); stent flexibility (clinical ratings: 57% excellent, 4% good, 26% fair, 13% poor); visibility by fluoroscopy (clinical ratings: 88% excellent, 14% fair); stent repositioning when required (clinical ratings: 86% excellent, 14% fair); deployment accuracy (clinical ratings: 84% excellent, 8% good, 8% fair); and device deployment time (clinical ratings: 76% excellent, 11% good, 9% fair, 4% poor). Procedural complications were experienced by five patients who had mild complications during the procedure assessed as bleeding after sphincteroplasty (3), supraventricular tachycardia (1) and hyperamylasemia (1). Throughout the twelve month follow-up period only one event occurred which caused particular treatment (this event emerged at day one after index-procedure and did not prolong the patient's hospital stay). In this instance, the patient developed elevated serum amylase without epigastric pain at day one after procedure, however, this was a very mild case and vanished spontaneously in twenty-four hours.

The stents of the present application have also been successfully tested in a study of prophylactic stenting in an anastomotic site in liver transplants in three patients.

In another study to show equivalence to standard plastic biliary stents, an elderly man in his early to mid to late sixties presented with repeat jaundice due to repeat stone obstruction in the common bile duct. The patient had been treated numerous times in the past for common bile duct obstruction due to stone formation. It was decided to cannulate the patient's common bile duct, perform stone removal using a standard balloon and repeat dilation of the duct and the papilla, and then stent using a fast absorbing biodegradable stent. The benefit of the biodegradable embodiment herein is that the follow up procedure to remove the stent can be eliminated as well as posterior wall irritation can be avoided through degradation. The papilla was distended and dilated and it was initially feared that one stent would dislodge and might not be adequate for the lesions. This fast absorbing device was placed using a standard guide wire (in certain embodiments, a super stiff wire may be advantageous for placing the stent into the duct). A 120 mm long, 3.4 mm diameter stent after duct dilation for stone removal was delivered without incident over the wire while manually manipulating the proximal antimigration as it was pushed into the scope. The stent entered the duct easily and the endoscope was positioned at the entrance of the papilla with limited distance and minor use of the scopes elevator to insure easy access. The stent entered the duct much like a metal stent when used.

On-going studies are being performed. For example, a study in a fifty year old female with a benign biliary structure, in which after pre-dilation a 3.4 mm OD×120 cam long, slow absorbing plastic biliary stent has been implanted. In another example, after thirty days post-procedure, the physician case report indicated the patient was asymptomatic and had no complications (no x-ray or fluoro imaging was required).

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence which is effective to meet the objectives there intended, unless the context specifically indicates the contrary.

What is claimed is:

1. A method of making a stent, comprising:
    forming an elongated body comprising a biodegradable material, wherein the elongated body has a proximal end, a distal end and a central lumen open at the proximal and distal ends of the stent for the passage of a guide wire; and
    twisting the elongated body to form at least one open spiral channels on the exterior surface of said body to provide fluid communication between said proximal end and said distal end; and
    shaping the stent's geometry by optimizing fluid flow rate between said proximal end and said distal end, and optimizing flexibility of the stent, by adjusting a rotation rate of the spiral channels along the stent based on the optimized fluid flow rate, and
    wherein the central lumen is not in fluid communication with the open spiral channels, and wherein said at least one open spiral channel has a rotation rate of at least 1 twist per inch.

2. The method of claim 1, wherein the elongated body is formed by extrusion.

3. The method of claim 1, wherein said at least one open spiral channel has a rotation rate of between about 1.5 and 3.5 twists per inch.

4. The method of claim 1, wherein said at least one open spiral channel has a rotation rate of at least about 2 twists per inch.

5. The method of claim 1, wherein said channels are on opposite sides on the exterior surface of said body.

6. The method of claim 1, further comprising forming an anti-migration device on the elongated body.

7. The method of claim 1, wherein said elongated body further comprises a biological agent.

8. The method of claim 7, wherein said biological agent is selected from the group consisting of chemotherapeutic agents, antimicrobial agents and gene transfer agents.

9. The method of claim 1, wherein said stent has a pre-implantation diameter $D_{pre}$ and is in situ expandable upon absorption of a body fluid to a post-implantation diameter $D_{post}$, wherein $D_{post}$ is greater than $D_{pre}$.

10. The method of claim 1, wherein the elongate body further comprises a radio-opaque substance.

11. The method of claim 1, wherein the biodegradable material comprises bioabsorbable polymer.

12. The method of claim 11, wherein the biodegradable polymer comprises PEG and p-dioxanone.

13. The method of claim 11, wherein the bioabsorbable polymer comprises PPDO.

14. The method of claim 11, wherein the bioabsorbable polymer comprises PLA, trimethylene carbonate and caprolactone.

15. The method of claim 1, further comprising:
    recording a target lumen's shape by optical photography and/or optical videography; and
    shaping the stent's geometry of corresponding zones and connector regions of the stent to the target lumen in accordance with the recorded target lumen's shape.

* * * * *